(12) United States Patent
Kagan

(10) Patent No.: US 11,351,250 B2
(45) Date of Patent: *Jun. 7, 2022

(54) PRO-INFLAMMATORY AND ANTI-CANCER FUNCTIONS OF TOLL-LIKE RECEPTOR 4 ANTAGONISTS

(71) Applicant: Children's Medical Center Corporation, Boston, MA (US)

(72) Inventor: Jonathan C. Kagan, Brookline, MA (US)

(73) Assignee: Children's Medical Center Corporation, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/018,045

(22) Filed: Sep. 11, 2020

(65) Prior Publication Data

US 2020/0405848 A1    Dec. 31, 2020

Related U.S. Application Data

(63) Continuation of application No. 15/543,165, filed as application No. PCT/US2016/012994 on Jan. 12, 2016, now abandoned.

(60) Provisional application No. 62/102,245, filed on Jan. 12, 2015.

(51) Int. Cl.
  *A61K 39/39* (2006.01)
  *A61K 39/00* (2006.01)

(52) U.S. Cl.
  CPC .... *A61K 39/39* (2013.01); *A61K 2039/55511* (2013.01); *A61K 2039/55516* (2013.01); *A61K 2039/55561* (2013.01); *A61K 2039/55566* (2013.01); *A61K 2039/55572* (2013.01); *A61K 2039/57* (2013.01); *A61K 2039/575* (2013.01); *Y02A 50/30* (2018.01)

(58) Field of Classification Search
  None
  See application file for complete search history.

(56) References Cited

U.S. PATENT DOCUMENTS

| | | |
|---|---|---|
| 5,158,939 A | 10/1992 | Takayama et al. |
| 2006/0257359 A1 | 11/2006 | Francois et al. |
| 2008/0311152 A1 | 12/2008 | Palinski et al. |
| 2010/0151000 A1 | 6/2010 | Thomas et al. |
| 2016/0312184 A1 | 10/2016 | Heuer et al. |
| 2017/0246281 A1 | 8/2017 | Doherty et al. |
| 2018/0318414 A1 | 11/2018 | Kagan |
| 2019/0151466 A1 | 5/2019 | Oppenheim et al. |
| 2020/0405847 A1 | 12/2020 | Kagan |

FOREIGN PATENT DOCUMENTS

| | | |
|---|---|---|
| EP | 0659439 | 10/2001 |
| JP | H4503363 A | 6/1992 |
| WO | WO 2000/026384 | 5/2000 |
| WO | WO 2004/006910 | 1/2004 |
| WO | WO 2011/136828 | 11/2011 |
| WO | WO 2012/177624 | 12/2012 |
| WO | WO 2013/088245 | 6/2013 |
| WO | WO 2014/164699 | 10/2014 |
| WO | WO 2018/067302 | 4/2018 |
| WO | WO 2019/213538 | 11/2019 |

OTHER PUBLICATIONS

Oskolkova et al. 2010 (Oxidized Phospholipids are more potent antagonists of lipopolysaccharide than inducers of inflammation; The Journal of Immunology 185: 7706-7712) (Year: 2010).*
Weber et al. 2013 (Blocking Toll-like receptor 2 and 4 signaling during a stressor prevents stress-induced priming of neuroinflammatory responses to a subsequent immune challenge; Brain Behav Immun 32: 1-21) (Year: 2013).*
Knapp et al. 2007 (Oxidized phospholipids inhibit phagocytosis and impair outcome in Gram-Negative Sepsis in Vivo; The Journal of Immunology; 178: 993-1001) (Year: 2007).*
Tan et al. 2014 (Oxidized low-density lipoprotein, OXPAPC, corrects defects in maturation and cytokine secretion of peripheral blood dendritic cells from sepsis patients; Int J Clin Exp Med 7(8):2067-2073) (Year: 2014).*
Hotchkiss 2014 (Parallels between Cancer and Infectious Disease; The New England Journal of Medicine; 371(4): 380-388) (Year: 2014).*
EP Office Action in European Appl. No. 16737709.2, dated Oct. 6, 2020, 8 pages.
Gangloff et al., "Influence of CD14 on ligand interactions between lipopolysaccharide and its receptor complex," The Journal of Immunology, Sep. 15, 2005, 175(6):3940-5.
Aachoui et al., "Caspase-11 protects against bacteria that escape the vacuole," Science, Feb. 22, 2013. 339(6122):975-8.
Aachoui et al., "Inflammasome-mediated pyroptotic and apoptotic cell death, and defense against infection," Current Opinion in Microbiology, Jun. 1, 2013, 16(3):319-26.
Aglietti et al., "GsdmD p30 elicited by caspase-11 during pyroptosis forms pores in membranes," Proceedings of the National Academy of Sciences, Jul. 12, 2016, 113(28):7858-63.
Alvarez et al., "Mechanisms and consequences of dendritic cell migration," Immunity, Sep. 19, 2008, 29(3):325-42.
Aoshi et al., "Innate immunity and next-generation vaccine," J-Stage, Drug Delivery System, Jan. 30, 2012, 27(1):19-27 (with English abstract).
Barnden et al., "Defective TCR expression in transgenic mice constructed using cDNA-based α-and β-chain genes under tire control of heterologous regulatory elements," Immunology and Cell Biology, Feb. 1998, 76(1):34-40.
Bennett et al., "Program death-1 engagement upon TCR activation has distinct effects on costimulation and cytokine-driven proliferation: attenuation of ICOS, IL-4, and IL-21, but not CD28, IL-7, and IL-15 responses." The Journal of Immunology, Jan. 15, 2003, 170(2):711-8.

(Continued)

*Primary Examiner* — Mary Maille Lyons
(74) *Attorney, Agent, or Firm* — Fish & Richardson P.C.

(57) ABSTRACT

The present invention provides methods and compositions for specific activation of inflammatory responses in dendritic cells (DCs). 1-palmitoyl-2-arachidonyl-sn-glycero-3-phosphorylcholine (PAPC) and its oxidized variant (oxPAPC) were identified to promote DC-mediated immunity, and are provided as adjuvants in immunostimulatory compositions, including vaccines.

17 Claims, 61 Drawing Sheets

(56) References Cited

OTHER PUBLICATIONS

Ben-Sasson et al., "IL-1 acts directly on CD4 T cells to enhance their antigen-driven expansion and differentiation," Proceedings of the National Academy of Sciences, Apr. 28, 2009, 106(17):7119-24.
Ben-Sasson et al., "IL-1 enhances expansion, effector function, tissue localization, and memory response of antigen-specific CD8 T cells," Journal of Experimental Medicine, Mar. 11, 2013, 210(3):491-502.
Ben-Sasson et al., "IL-1β strikingly enhances antigen-driven CD4 and CD8 T-cell responses," Cold Spring Harbor Symposia on Quantitative Biology, Jan. 1, 2013, 78, 117-24.
Berliner et al., "A role for oxidized phospholipids in atherosclerosis," New England Journal of Medicine, Jul. 7, 2005. 353(1):9-11.
Blander et al., "Beyond pattern recognition: five immune checkpoints for scaling the microbial threat," Nature Reviews Immunology, Mar. 2012, 12(3):215-25.
Blander et al., "Toll-dependent selection of microbial antigens for presentation by dendritic cells," Nature, Apr. 2006, 440(7085):808-12.
Blander, "A long-awaited merger of the pathways mediating host defence and programmed cell death," Nature Reviews Immunology, Sep. 2014, 14(9):601-18.
Blank et al., "Interaction of PD-L1 on tumor cells with PD-1 on tumor-specific T cells as a mechanism of immune evasion: implications for tumor immunotherapy," Cancer Immunology, Immunotherapy, Apr. 1, 2005, 54(4):307-14.
Bochkov et al., "Protective role of phospholipid oxidation products in endotoxin-induced tissue damage," Nature, Sep. 2002, 419(6902):77-81.
Brewer et al., "Aluminium hydroxide adjuvant initiates strong antigen-specific Th2 responses in the absence of IL-4-or IL-13-mediated signaling," The Journal of Immunology, Dec. 15, 1999, 163(12):6448-54.
Broz et al., "Caspase-11 increases susceptibility to *Salmonella* infection in the absence of caspase-1," Nature, Oct. 2012. 490(7419):288-91.
Broz et al., "Differential requirement for Caspase-1 autoproteolysis in pathogen-induced cell death and cytokine processing," Cell Host & Microbe, Dec. 16, 2010, 8(6):471-83.
Brubaker et al., "Innate immune pattern recognition: a cell biological perspective," Annual Review of Immunology, Mar. 21, 2015, 33:257-90.
Butte et al., "Interaction of human PD-L1 and B7-1. Molecular immunology," Aug. 1, 2008, 45(13):3567-72.
Carter et al., "PD-1: PD-L inhibitory pathway affects both CD4+ and CD8+ T cells and is overcome by IL-2," European Journal of Immunology, Mar. 2002, 32(3):634-43.
Case et al., "Caspase-11 stimulates rapid flagellin-independent pyroptosis in response to Legionella pneumophila," Proceedings of the National Academy of Sciences, Jan. 29, 2013, 110(5):1851-6.
Casson et al., "Caspase-11 activation in response to bacterial secretion systems that access the host cytosol," PLoS Pathog, Jun. 6, 2013, 9(6).
Castle et al., "Exploiting the mutanome for tumor vaccination," Cancer Research, Mar. 1, 2012, 72(5):1081-91.
Ceballos-Olvera et al., "Inflammasome-dependent pyroptosis and IL-18 protect against Burkholderia pseudomallei lung infection while IL-1β is deleterious." PLoS Pathog, Dec. 29, 2011, 7(12), 13 pages.
Chang et al., "Apoptotic cells with oxidation-specific epitopes are immunogenic and proinflammatory," The Journal of Experimental Medicine, Dec. 6, 2004, 200(11):1359-70.
Cliffe et al., "Transcription of the herpes simplex virus latency-associated transcript promotes the formation of facultative heterochromatin on lytic promoters," Journal of Virology, Aug. 15, 2009, 83(16):8182-90.

Coen et al, "Thymidine kinase-negative herpes simplex virus mutants establish latency in mouse trigeminal ganglia but do not reactivate," Proceedings of the National Academy of Sciences, Jun. 1, 1989, 86(12):4736-40.
Delamarre et al., "Differential lysosomal proteolysis in antigen-presenting cells determines antigen fate," Science, Mar. 11, 2005, 307(5715):1630-4.
Didierlaurent et al., "AS04, an aluminum salt-and TLR4 agonist-based adjuvant system, induces a transient localized innate immune response leading to enhanced adaptive immunity," The Journal of Immunology, Nov. 15, 2009, 183(10):6186-97.
Djenidi et al., "CD8+ CD103+ tumor-infiltrating lymphocytes are tumor-specific tissue-resident memory T cells and a prognostic factor for survival in lung cancer patients," The Journal of Immunology, Apr. 1, 2015, 194(7):3475-86.
Dong et al., "Tumor-associated B7-H1 promotes T-cell apoptosis: a potential mechanism of immune evasion," Nature Medicine, Aug. 2002, 8(8):793-800.
Eisenbarth et al., "Crucial role for the Nalp3 inflammasome in the immunostimulatory properties of aluminium adjuvants," Nature, Jun. 2008, 453(7198):1122-6.
EP European Search Report in European Appln. No. 16737709.2, dated Aug. 2, 2018, 11 pages.
Erridge et al., "Oxidized phospholipid inhibition of toll-like receptor (TLR) signaling is restricted to TLR2 and TLR4 roles for cd14, lps-binding protein, and md2 as targets for specificity of inhibition," Journal of Biological Chemistry, Sep. 5, 2008, 283(36):24748-59.
Evavold et al., "The pore-forming protein gasdermin D regulates interleukin-1 secretion from living macrophages," Immunity, Jan. 16, 2018, 48(1):35-44.
Franchi et al., "Nlrp3 inflammasome is critical for aluminium hydroxide-mediated IL-1β secretion but dispensable for adjuvant activity," European Journal of Immunology, Aug. 2008, 38(8):2085-9.
Freeman et al., "Engagement of the PD-1 immunoinhibitory receptor by a novel B7 family member leads to negative regulation of lymphocyte activation," The Journal of Experimental Medicine, Oct. 2, 2000, 192(7):1027-34.
Fruhwirth et al., "Oxidized phospholipids: from molecular properties to disease," Biochimica et Biophysica Acta (BBA)-Molecular Basis of Disease, Jul. 1, 2007, 1772(7):718-36.
Garlanda et al., "The interleukin-1 family: back to the future," Immunity, Dec. 12, 2013, 39(6):1003-18.
Ghiringhelli et al., "Activation of the NLRP3 inflammasome in dendritic cells induces IL-1β-dependent adaptive immunity against tumors," Nature Medicine, Oct. 2009, 15(10):1170-8.
Gimenez et al., "The inflammasome NLRP3 plays a protective role against a viral immunopathological lesion," Journal of Leukocyte Biology, Oct. 29, 2015, 99(5):647-57.
Gundacker et al., "Cytoplasmic proteorne and secretome profiles of differently stimulated human dendritic cells," Journal of Proteome Research, Jun. 5, 2009, 8(6):2799-811.
Hagar et al., "Detection of cytosolic bacteria by inflammatory caspases," Current Opinion in Microbiology, Feb. 1, 2014, 17:61-6.
Hagar et al., "LPS activates caspase-11: implications in TLR4-independent endotoxic shock," Science, Sep. 13, 2013, 341(6151):1250-3.
Han et al., "White adipose tissue is a reservoir for memory T cells and promotes protective memory responses to infection," Immunity, Dec. 19, 2017, 47(6):1154-68.
Hogquist et al., "Carbone FR. T cell receptor antagonist peptides induce positive selection," Cell, Jan. 14, 1994, 76(1):17-27.
Honda et al., "Spatiotemporal regulation of MyD88-IRF-7 signalling for robust type-I interferon induction," Nature, Apr. 2005, 434(7036):1035-40.
Hu et al., "Towards personalized, tumour-specific, therapeutic vaccines for cancer," Nature Reviews Immunology, Mar. 2018, 18(3):168.
Imai et al., "Identification of oxidative stress and Toll-like receptor 4 signaling as a key pathway of acute lung injury," Cell, Apr. 18, 2008, 133(2):235-49.
Inaba et al., "The formation of immunogenic major histocompatibility complex class II-peptide ligands in lysosomal compartments

(56) References Cited

OTHER PUBLICATIONS of dendritic cells is regulated by inflammatory stimuli," The Journal of Experimental Medicine, Mar. 20, 2000, 191(6):927-36.
Iwai et al., "Involvement of PD-L1 on tumor cells in the escape from host immune system and tumor immunotherapy by PD-L1 blockade," Proceedings of the National Academy of Sciences, Sep. 17, 2002, 99(19):12293-7.
Iwasaki et al., "Control of adaptive immunity by the innate immune system," Nature Immunology, Apr. 2015, 16(4):343-53.
Janeway el al., "Innate immune recognition," Annual Review of Immunology, Apr. 2002, 20(1):197-216.
Janeway, "A trip through my life with an immunological theme," Annual Review of Immunology, Apr. 2002, 20(1):1-28.
Janeway, "Approaching the asymptote? Evolution and revolution in immunology," Cold Spring Harbor Symposia on Quantitative Biology, Jan. 1, 1989, 54:1-13.
Joffre et al., "Inflammatory signals in dendritic cell activation and the induction of adaptive immunity," Immunological Reviews, Jan. 2009, 227(1):234-47.
JP Office Action in Japanese Appln. No. 2017-555445, dated Aug. 21, 2020, 10 pages (with English translation).
JP Office Action in Japanese Appln. No. 2017-555445, dated Oct. 10, 2019, 13 pages (with English translation).
Kagan et al., "SMOCs: supramolecular organizing centres that control innate immunity," Nature Reviews Immunology, Dec. 2014, 14(12):821-6.
Kanai et al., "Blockade of B7-H1 suppresses the development of chronic intestinal inflammation," The Journal of Immunology, Oct. 15, 2003, 171(8):4156-63.
Kayagaki et al., "Caspase-11 cleaves gasdermin D for noncanonical inflammasome signalling," Nature, Oct. 2015, 526(7575):666-71.
Kayagaki et al., "Noncanonical inflammasome activation by intracellular LPS independent of TLR4," Science, Sep. 13, 2013, 341(6151):1246-9.
Keskin et al., "Neoantigen vaccine generates intratumoral T cell responses in phase Ib glioblastoma trial," Nature, Jan. 2019, 565(7738):234-9.
Kieser et al., "Multi-receptor detection of individual bacterial products by the innate immune system," Nature Reviews Immunology, Jun. 2017, 17(6):376-390.
Kim et al., "Crystal structure of CD14 and its implications for lipopolysaccharide signaling," Journal of Biological Chemistry, Mar. 25, 2005, 280(12):11347-51.
Kim et al., "Paraoxonase-2 Modulates Stress Response of Endothelial Cells to Oxidized Phospholipids and a Bacterial Quorum-Sensing Molecule," Arteriosclerosis, Thrombosis, and Vascular Biology, Nov. 2011, 31(11):2624-33.
Knapp et al., "Oxidized phospholipids inhibit phagocytosis and impair outcome in gram-negative sepsis in vivo," The Journal of Immunology, Jan. 15, 2007, 178(2):993-1001.
Koebel et al., "Adaptive immunity maintains occult cancer in an equilibrium state," Nature, Dec. 2007, 450(7171):903-7.
Kono et al., "How dying cells alert the immune system to danger," Nature Reviews Immunology, Apr. 2008, 8(4):279-89.
Kool et al., "Alum adjuvant boosts adaptive immunity by inducing uric acid and activating inflammatory dendritic cells," The Journal of Experimental Medicine, Apr. 14, 2008, 205(4):869-82.
Kool et al., "Cutting edge: alum adjuvant stimulates inflammatory dendritic cells through activation of the NALP3 inflammasome," The Journal of Immunology, Sep. 15, 2008, 181(6):3755-9.
Kundi et al., "New hepatitis B vaccine formulated with an improved adjuvant system," Expert Review of Vaccines, Apr. 1, 2007, 6(2):133-40.
Lamkanfi et al., "Mechanisms and functions of inflammasomes," Cell, May 22, 2014, 157(5):1013-22.
Latchman et al., "PD-L2 is a second ligand for PD-1 and inhibits T cell activation," Nature Immunology, Mar. 2001, 2(3):261-8.
Laumont et al., "Noncoding regions are the main source of targetable tumor-specific antigens," Science Translational Medicine, Dec. 5, 2018, 10(470):eaau5516, 12 pages.
Leitinger et al., "Oxidized phospholipids as modulators of inflammation in atherosclerosis," Current Opinion in Lipidology, Oct. 1, 2003, 14(5):421-30.
Li et al., "Aluminum hydroxide adjuvants activate caspase-1 and induce IL-1β and IL-18 release." The Journal of Immunology, Apr. 15, 2007, 178(8):5271-6.
Lin et al., "Helical assembly in the MyD88-IRAK4-IRAK2 complex in TLR/IL-1R signalling," Nature, Jun. 2010, 465(7300):885-90.
Liu et al., "Inflammasome-activated gasdermin D causes pyroptosis by forming membrane pores," Nature, Jul. 2016, 535(7610):453-8.
Lu et al., "Unified polymerization mechanism for the assembly of ASC-dependent inflammasomes," Cell, Mar. 13, 2014, 156(6):1193-206.
Manček-Keber et al., "Toll-like receptor 4 senses oxidative stress mediated by the oxidation of phospholipids in extracellular vesicles," Science Signaling, Jun. 16, 2015, 8(381):ra60, 13 pages.
Marichal et al., "DNA released from dying host cells mediates aluminum adjuvant activity," Nature Medicine, Aug. 2011, 17(8):996, 8 pages.
Marrack et al., "Towards an understanding of the adjuvant action of aluminium," Nature Reviews Immunology, Apr. 2009, 9(4):287-93.
Martinon et al., "The inflammasome: a molecular platform triggering activation of inflammatory caspases and processing of proIL-β," Molecular Cell, Aug. 1, 2002, 10(2):417-26.
Matzinger, "The danger model: a renewed sense of self." Science, Apr. 12, 2002, 296(5566):301-5.
Mellman et al., "Dendritic cells: specialized and regulated antigen processing machines," Cell, Aug. 10, 2001, 106(3):255-8.
Mempel et al., "T-cell priming by dendritic cells in lymph nodes occurs in three distinct phases," Nature, Jan. 2004, 427(6970):154-9.
Mishra et al., "Biomimetic temporal self-assembly via fuel-driven controlled supramolecular polymerization," Nature Communications, Mar. 30, 2018, 9(1):1-9.
Mohsen et al., "Targeting mutated plus germline epitopes confers pre-clinical efficacy of an instantly formulated cancer nanovaccine." Frontiers in Immunology, May 15, 2019, 10:1015.
Mori et al., "The vaccine adjuvant alum inhibits IL-12 by promoting PI 3 kinase signaling while chitosan does not inhibit IL-12 and enhances T h1 and T h17 responses," European Journal of Immunology, Oct. 2012, 42(10):2709-19.
Motshwene et al., "An oligomeric signaling platform formed by the Toll-like receptor signal transducers MyD88 and IRAK-4," Journal of Biological Chemistry, Sep. 11, 2009, 284(37):25404-11.
Nair-Gupta et al., "TLR signals induce phagosomal MHC-I delivery from the endosomal recycling compartment to allow cross-presentation," Cell, Jul. 31, 2014, 158(3):506-21.
Newman et al., "Saponin adjuvant induction of ovalbumin-specific CD8+ cytotoxic T lymphocyte responses," The Journal of Immunology, Apr. 15, 1992, 148(8):2357-62.
Nicolaou et al., "A Rationally Designed Molecule with Extremely Potent and Selective DNA Cleaving Properties and Apoptosis Inducing Activity," Angewandte Chemie International Edition in English, Feb. 1, 1994, 33(2):183-6.
Ohigashi et al., "Clinical significance of programmed death-1 ligand-1 and programmed death-1 ligand-2 expression in human esophageal cancer." Clinical Cancer Research, Apr. 15, 2005, 11(8):2947-53.
Okazaki et al., New regulatory co-receptors: inducible co-stimulator and PD-1. Current opinion in immunology. Dec. 1, 2002;14(6):779-82.
Okazaki et al., "PD-1 and PD-1 ligands: from discovery to clinical application." International Immunology, Jul. 1, 2007, 19(7):813-24.
Oleszycka et al., "The vaccine adjuvant alum promotes IL-10 production that suppresses Th1 responses." European Journal of Immunology, Apr. 2018, 48(4):705-15.
Oskolkova et al., "Oxidized phospholipids are more potent antagonists of lipopolysaccharide than inducers of inflammation," The Journal of Immunology, Dec. 15, 2010, 185(12):7706-12.

(56) References Cited

OTHER PUBLICATIONS

Ott et al., "An immunogenic personal neoantigen vaccine for patients with melanoma." Nature, Jul. 2017, 547(7662):217-21.
Paavonen et al., "Efficacy of human papillomavirus (HPV)-16/18 AS04-adjuvanted vaccine against cervical infection and precancer caused by oncogenic HPV types (PATRICIA): final analysis of a double-blind, randomised study in young women," The Lancet, Jul. 25, 2009, 374(9686):301-14.
Park et al., "Tissue-resident memory CD8+ T cells promote melanoma-immune equilibrium in skin," Nature, Jan. 2019, 565(7739):366-71.
Pasare et al., "Toll-dependent control mechanisms of CD4 T cell activation," Immunity, Nov. 1, 2004, 21(5):733-41.
Paterson et al., "The programmed death-1 ligand 1: B7-1 pathway restrains diabetogenic effector T cells in vivo," The Journal of Immunology, Aug. 1, 2011, 187(3):1097-105.
PCT International Search Report and Written Opinion in international Appln. No. PCT/US2016/012994, dated Jan. 12, 2016—11 pages.
Pétrilli et al., "The inflammasome: a danger sensing complex triggering innate immunity," Current Opinion in Immunology, Dec. 1, 2007, 19(6):615-22.
Pierre et al., "Developmental regulation of MHC class II transport in mouse dendritic cells," Nature, Aug. 1997, 388(6644):787-92.
Poltorak et al., "Defective LPS signaling in C3H/HeJ and C57BL/10ScCr mice: mutations in Tlr4 gene," Science, Dec. 11, 1998, 282(5396):2085-8.
Pradeu et al., "The danger theory: 20 years later," Frontiers in Immunology, Sep. 17, 2012, 3:287, 9 pages.
Rathinam et al., "TRIF licenses caspase-11-dependent NLRP3 inflammasome activation by gram-negative bacteria," Cell, Aug. 3, 2012, 150(3):606-19.
Rühl et al., "ESCRT-dependent membrane repair negatively regulates pyroptosis downstream of GSDMD activation," Science, Nov. 23, 2018, 362(6417):956-60.
Sabado et al., "Dendritic cell-based immunotherapy," Cell Research, Jan. 2017. 27(1):74-95.
Sabroe et al., "Toll-like receptors in health and disease: complex questions remain." The Journal of Immunology, Aug. 15, 2003. 171(4):1630-5.
Schenten et al., "Signaling throush the adaptor molecule MyD88 in CD4+ T cells is required to overcome suppression by regulatory T cells," Immunity, Jan. 16, 2014, 40(1):78-90.
Schmidt et al., "Distinct licensing of IL-18 and IL-1β secretion in response to NLRP3 inflammasome activation." PloS one, Sep. 18, 2012, 7(9):e45186.
Schnare et al., "Toll-like receptors control activation of adaptive immune responses," Nature Immunology, Oct. 2001, 2(10):947-50.
Sheppard et al., "PD-1 inhibits T-cell receptor induced phosphorylation of the ZAP70/CD3ζ signalosome and downstream signaling to PKCθ," FEBS Letters, Sep. 10, 2004, 574(1-3):37-41.
Shi et al., "Cleavage of GSDMD by inflammatory caspases determines pyroptotic cell death," Nature, Oct. 2015, 526(7575):660-5.
Shi et al., "Inflammatory caspases are innate immune receptors for intracellular LPS," Nature, Oct. 2014, 514(7521):187-92.
Shirey et al., "The TLR4 antagonist Eritoran protects mice from lethal influenza infection," Nature, May 2013, 497(7450):498-502.
Sims et al., "The IL-1 family: regulators of immunity," Nature Reviews Immunology, Feb. 2010, 10(2):89-102.
Springstead et al., "Evidence for the importance of OxPAPC interaction with cysteines in regulating endothelial cell function," Journal of Lipid Research, Jul. 1, 2012, 53(7):1304-15.
Stutz et al., "ASC speck formation as a readout for inflammasome activation," Methods in Molecular Biology, Dec. 31, 2012, 1040:91-101.
Tan et al., "Mechanisms of Toll-like receptor 4 endocytosis reveal a common immune-evasion strategy used by pathogenic and commensal bacteria," Immunity, Nov. 17, 2015, 43(5):909-22.
Thompson et al., "Tumor B7-H1 is associated with poor prognosis in renal cell carcinoma patients with long-term follow-up," Cancer Research, Apr. 1, 2006, 66(7):3381-5.
Trombetta et al., "Activation of lysosomal function during dendritic cell maturation." Science, Feb. 28, 2003, 299(5611):1400-3.
Turley et al., "Transport of peptide-MHC class II complexes in developing dendritic cells," Science, Apr. 21, 2000, 288(5465):522-7.
Vance et al., "Patterns of pathogenesis: discrimination of pathogenic and nonpathosenic microbes by the innate immune system," Cell Host & Microbe, Jul. 23, 2009, 6(1):10-21.
Webb et al., "Tumor-infiltrating lymphocytes expressing the tissue resident memory marker CD103 are associated with increased survival in high-grade serous ovarian cancer," Clinical Cancer Research, Jan. 15, 2014, 20(2):434-44.
Weber et al., "Blocking toll-like receptor 2 and 4 signaling during a stressor prevents stress-induced priming of neuroinflammatory responses to a subsequent immune challenge," Brain, Behavior, and Immunity, Aug. 1, 2013, 32:112-21.
Yang et al., "Caspase-11 requires the pannexin-1 channel and the purinergic P2X7 pore to mediate pyroptosis and endotoxic shock," Immunity, Nov. 17, 2015, 43(5):923-32.
Yang et al., "Non-canonical activation of inflammatory caspases by cytosolic LPS in innate immunity," Current Opinion in Immunology, Feb. 1, 2015, 32:78-83.
Ye et al., "NLR, the nucleotide-binding domain leucine-rich repeat containing gene family," Current Opinion in Immunology, Feb. 1, 2008, 20(1):3-9.
Zanoni et al., "An endogenous caspase-11 ligand elicits interleukin-1 release from living dendritic cells," Science, Jun. 3, 2016, 352(6290):1232-6.
Zanoni et al., "By capturing inflammatory lipids released from dying cells, the receptor CD14 induces inflammasome-dependent phagocyte hyperactivation," Immunity, Oct. 2017, 47(4):697-709.
Zanoni et al., "CD14 controls the LPS-induced endocytosis of Toll-like receptor 4," Cell, Nov. 11, 2011, 147(4):868-80.
Zanoni et al., "CD14 regulates the dendritic cell life cycle after LPS exposure through NFAT activation," Nature, Jul. 2009, 460(7252):264-8.
AU Office Action in Australian Appln. No. 2016206965, dated Oct. 19, 2020, 8 pages.
Tan et al., "Oxidized low-density lipoprotein, OXPAPC, corrects defects in maturation and cytokine secretion of peripheral blood dendritic cells from sepsis patients," International Journal of Clinical and Experimental Medicine, Aug. 15, 2014, 7(8):2067-73.
Stenutz et al., "The structures of *Escherichia coli* O-polysaccharide antigens," FEMS Microbiol Rev., 2006, 30(3):382-403.
JP Japanese Office Action in Japanese Appln. No. 2020-213210, dated Nov. 30, 2021, 8 pages (with English translation).
JP Japanese Office Action in Japanese Appln. No. 2020-213211, dated Nov. 30, 2021, 7 pages (with English translation).
Oblak et al., "Toll-like receptor 4 activation in cancer progression and therapy," Clinical and Developmental Immunology, Oct. 2011, vol. 2011, 13 pages.
PCT International Search Report and Written Opinion in International Appln. No. PCT/US2020/061132, dated Feb. 9, 2021, 9 pages.
PCT International Search Report and Written Opinion in International Appln. No. PCT/US2020/061133. dated Mar. 11, 2021, 12 pages.
CA Office Action in Canadian Appl. No. 2,973,585, dated Feb. 17, 2022, 4 pages.

* cited by examiner

Figure 6
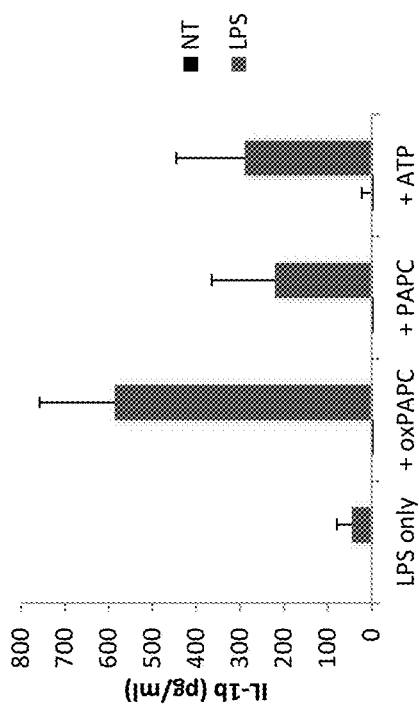
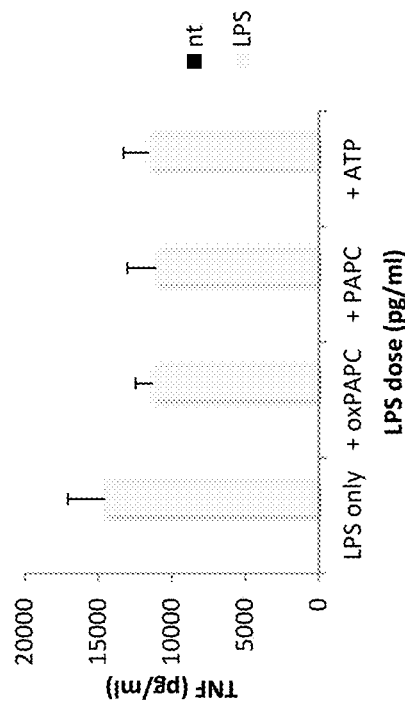
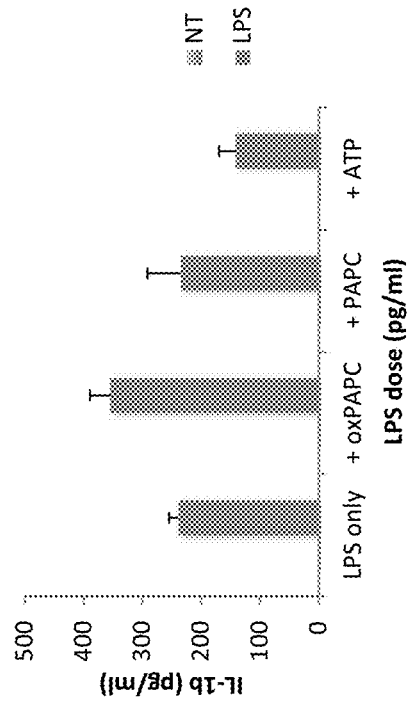

Figure 8
IL-1b secretion in response to PLs was strongly impaired in cd14-/- DCs
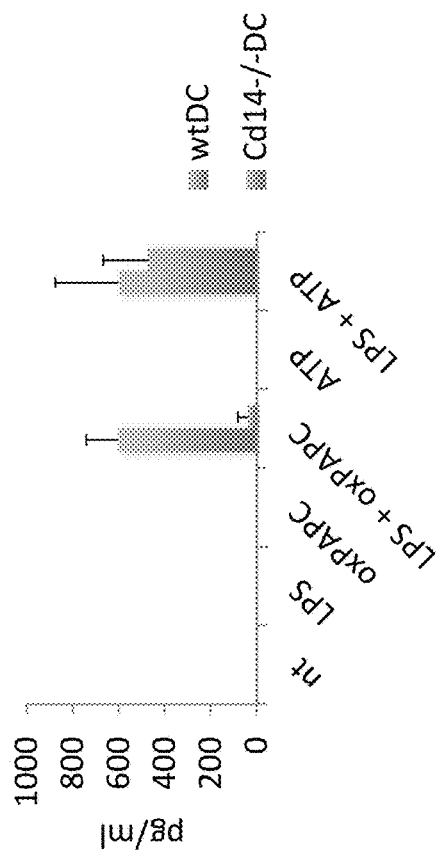
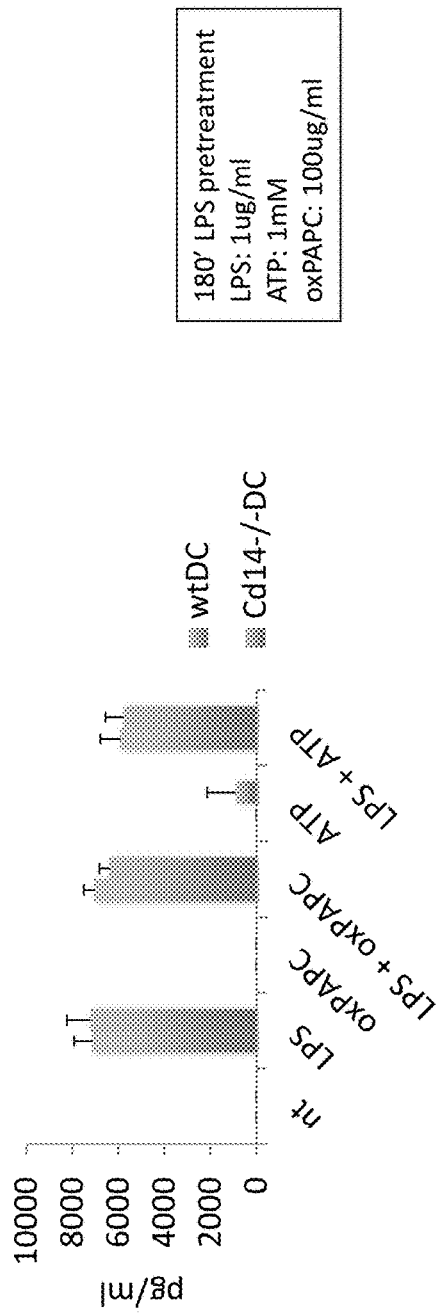
TNF secretion was not altered in cd14-/-DCs compared to wtDCs Co-administration of 100ng/ml LPS O55 and oxPAPC (100 and 40ug/ml)

Co-administration of 100ng/ml LPS O55 and oxPAPC (100 and 40ug/ml)

Co-administration of 100ng/ml LPS O55 and oxPAPC (100 and 40ug/ml)

Figures 43A-D
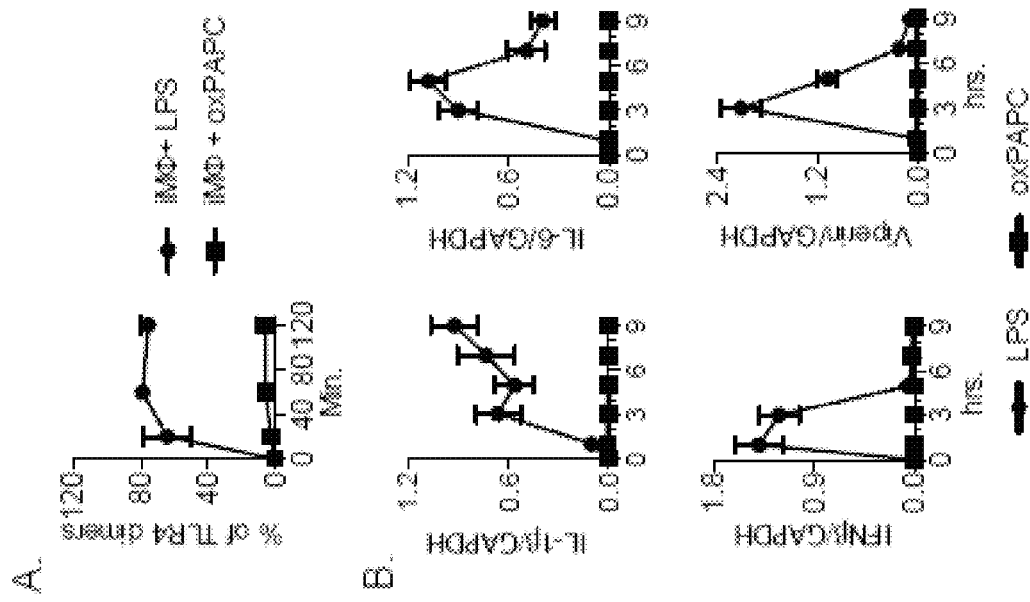

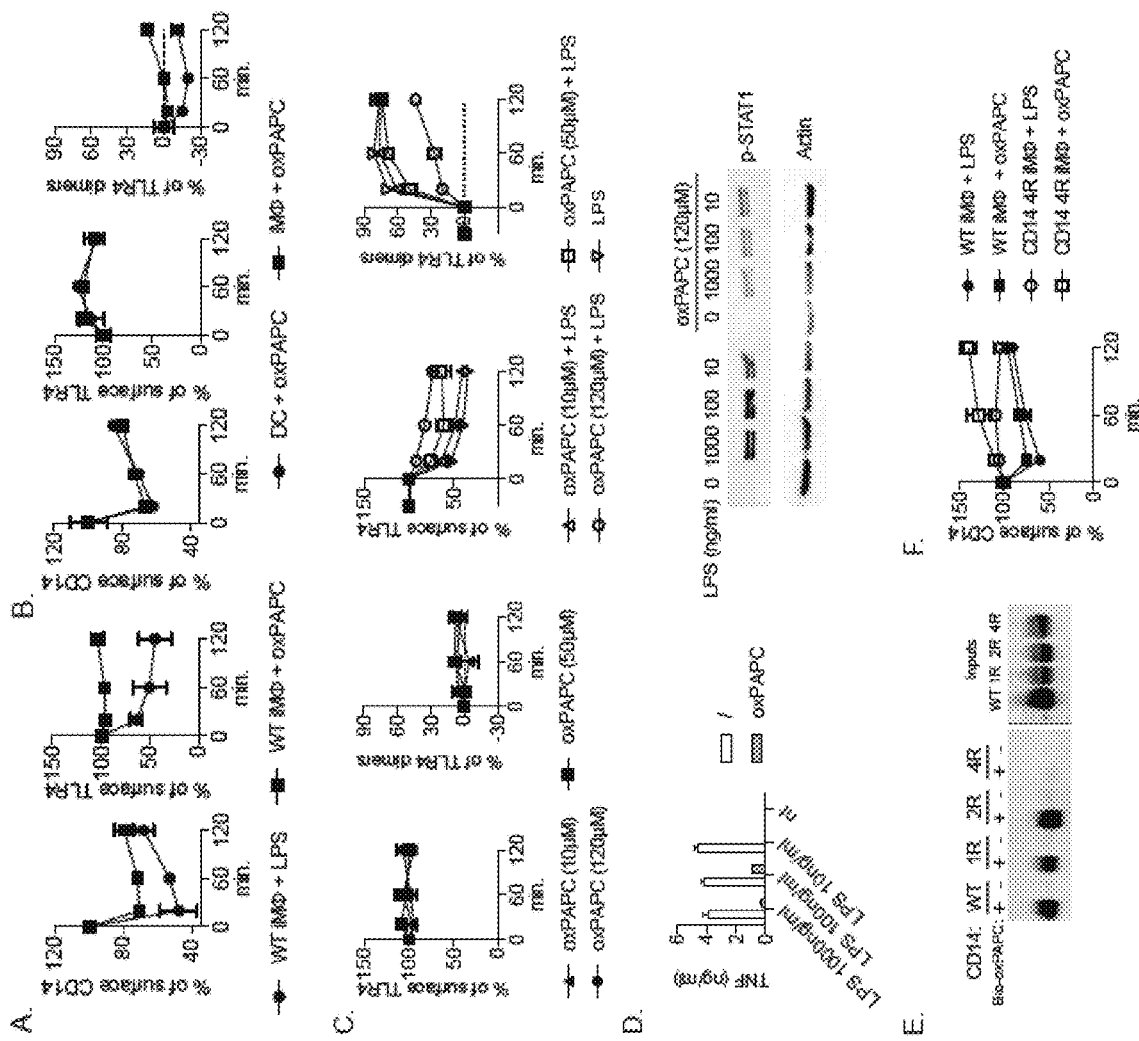
Figures 44A-F

Figures 45A-C
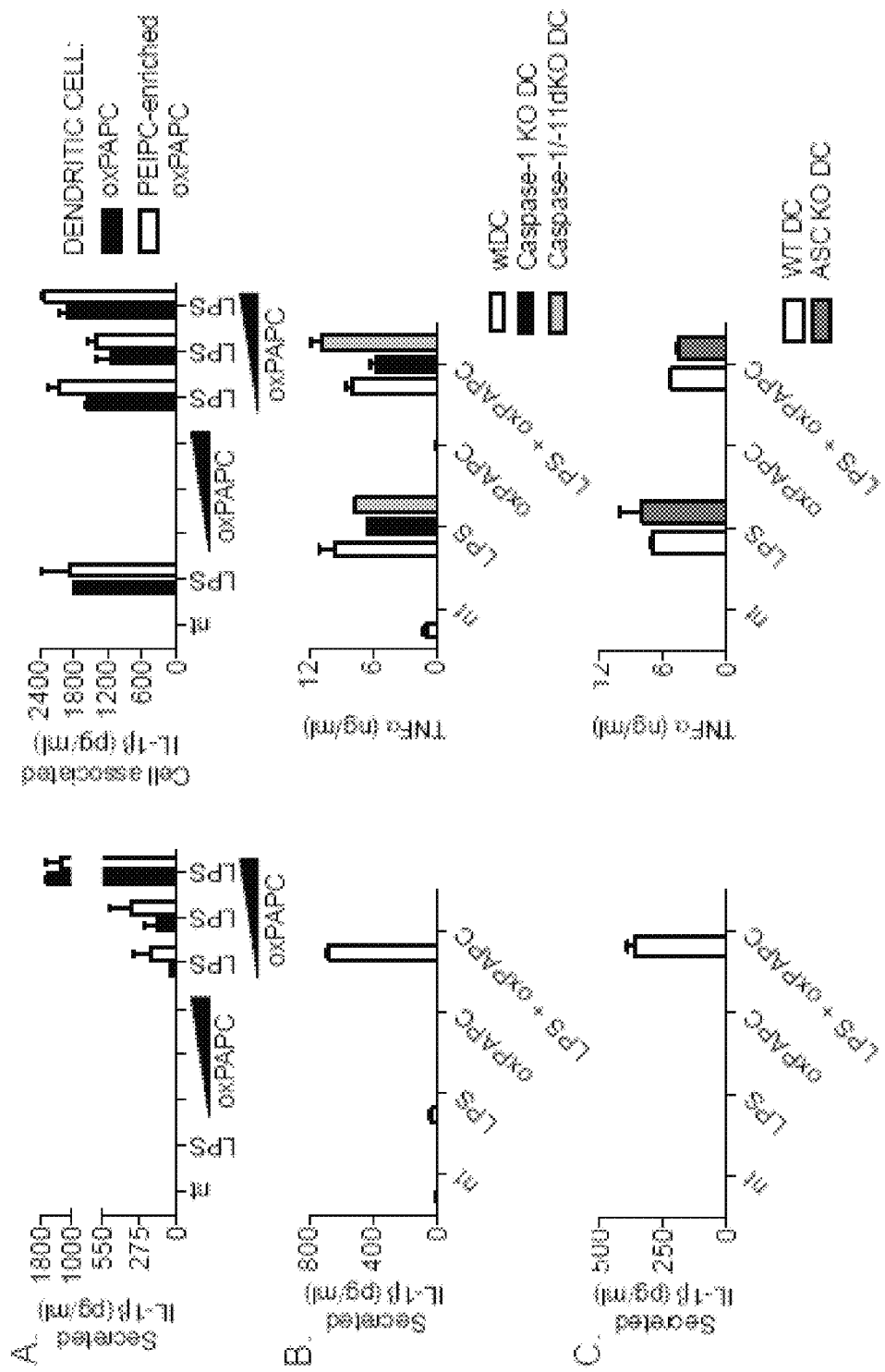

Figures 45D-G
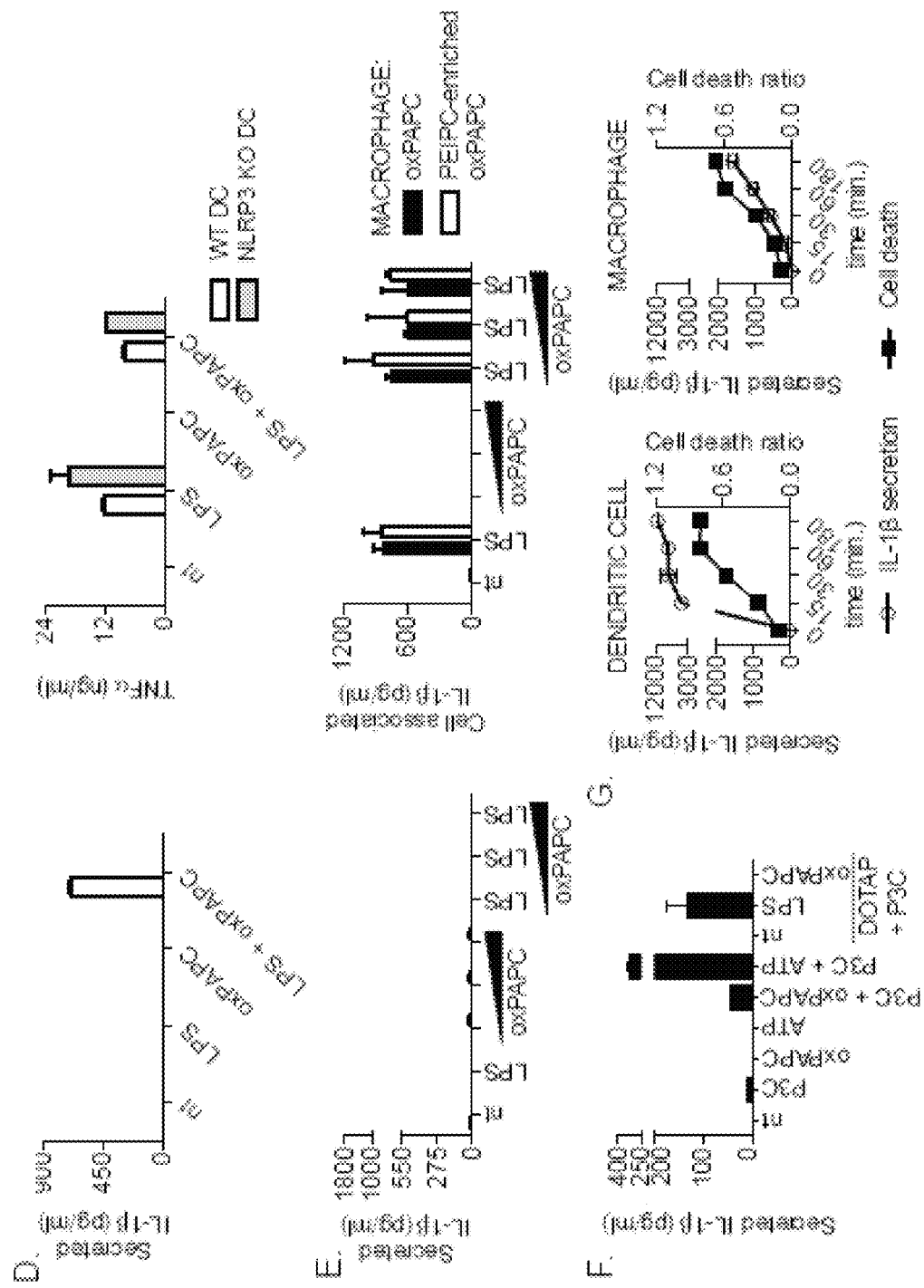

Figures 46A-D
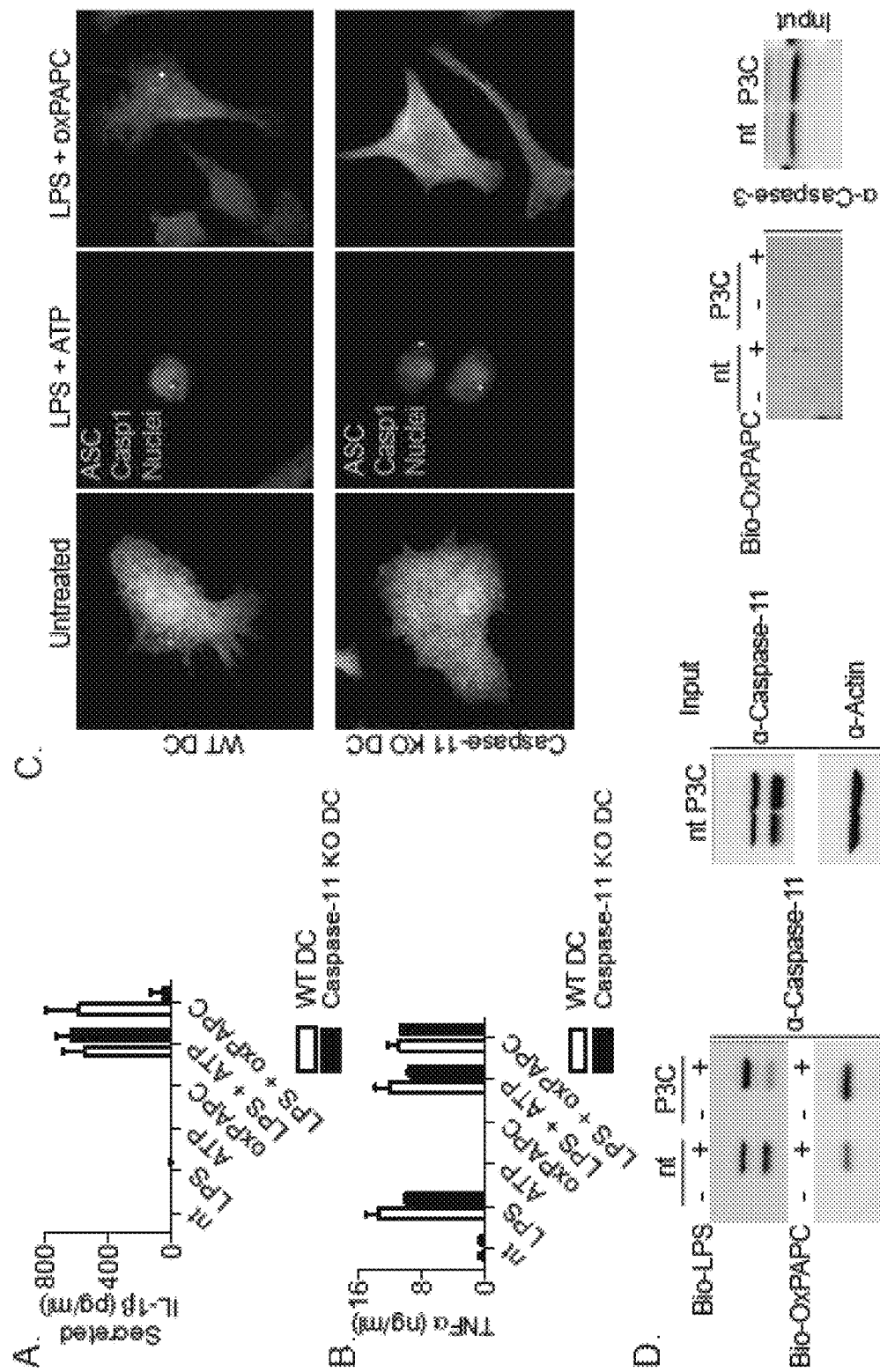

Figures 46E-G
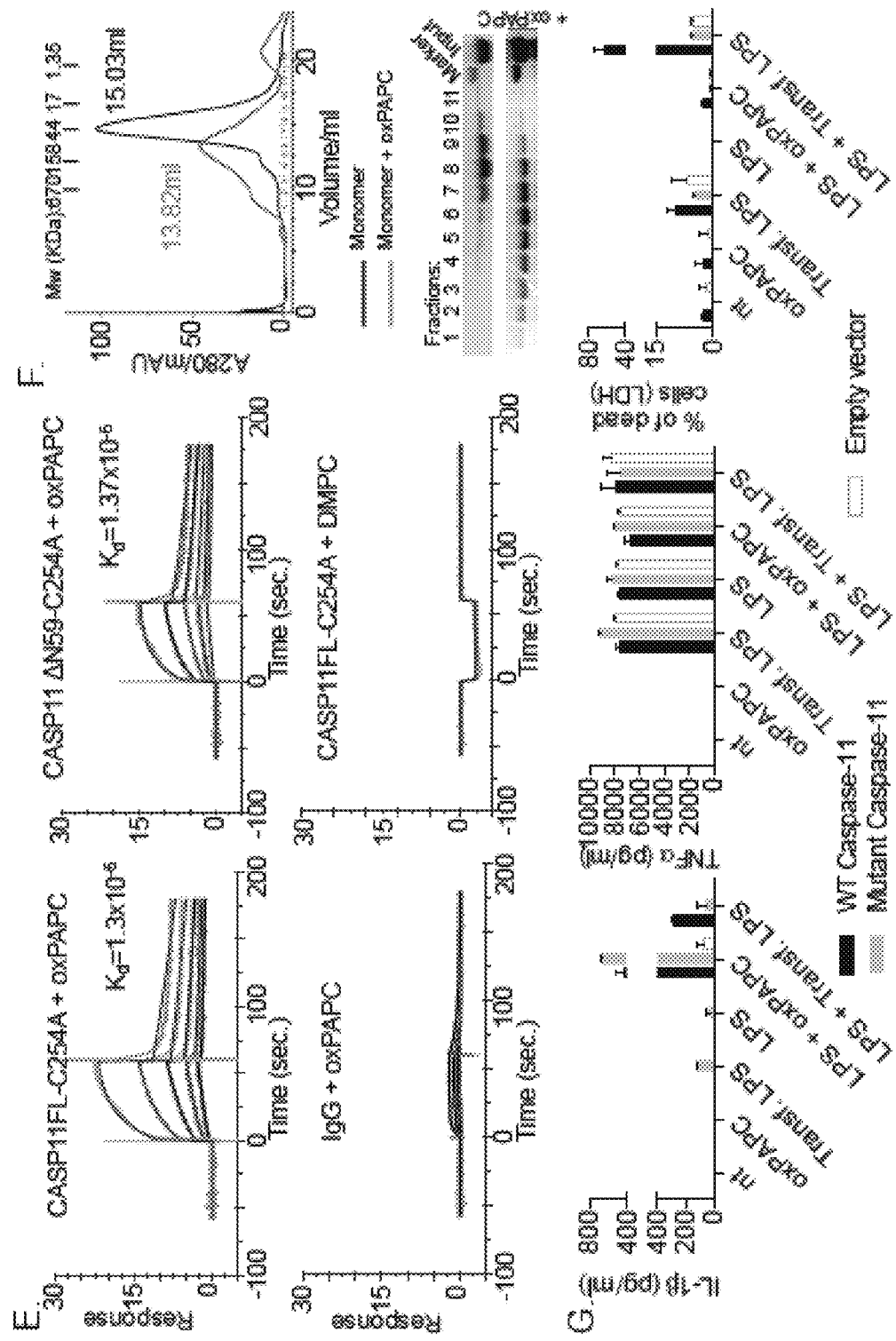

Figures 47A-C
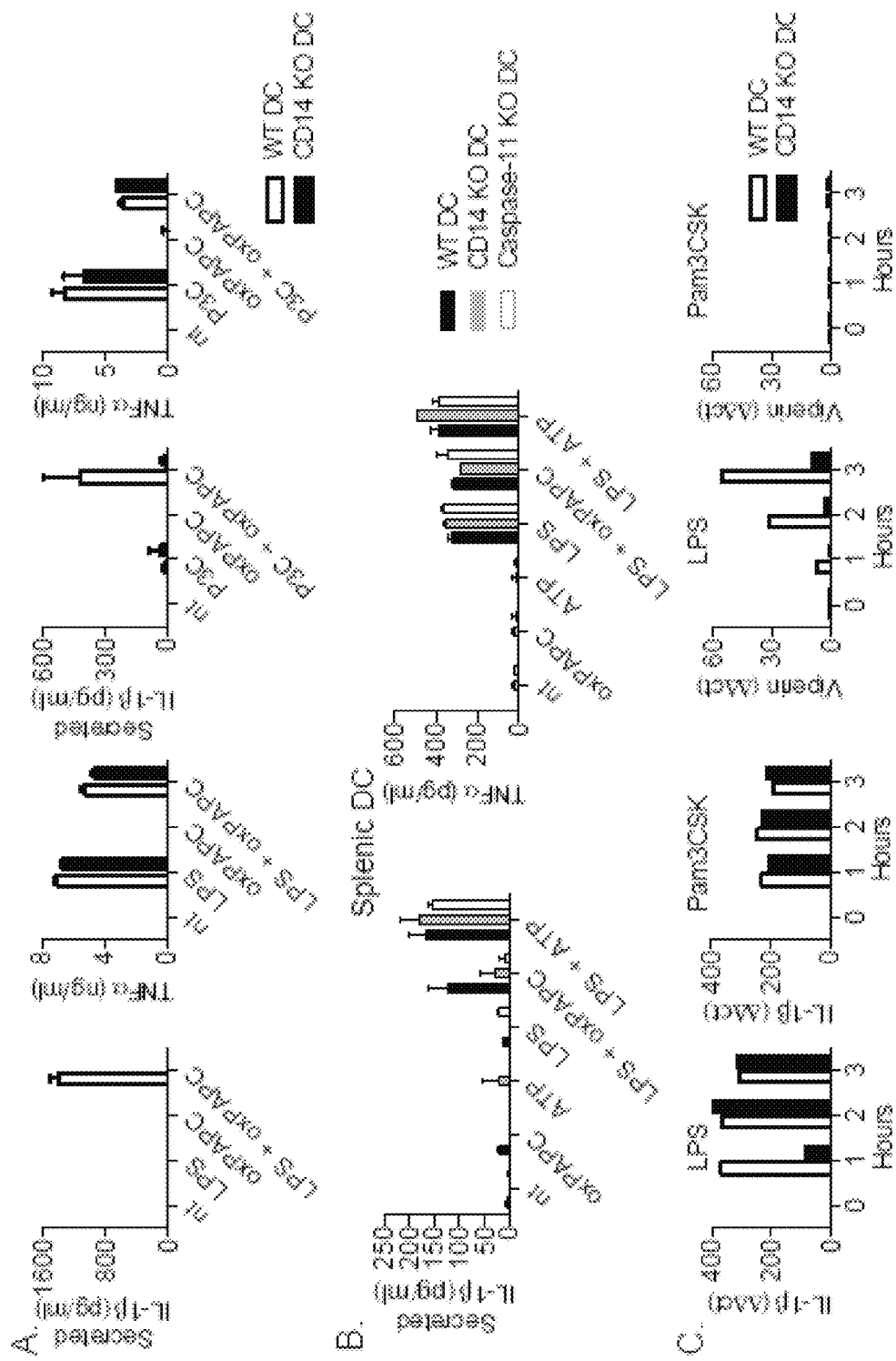

Figures 47D-E
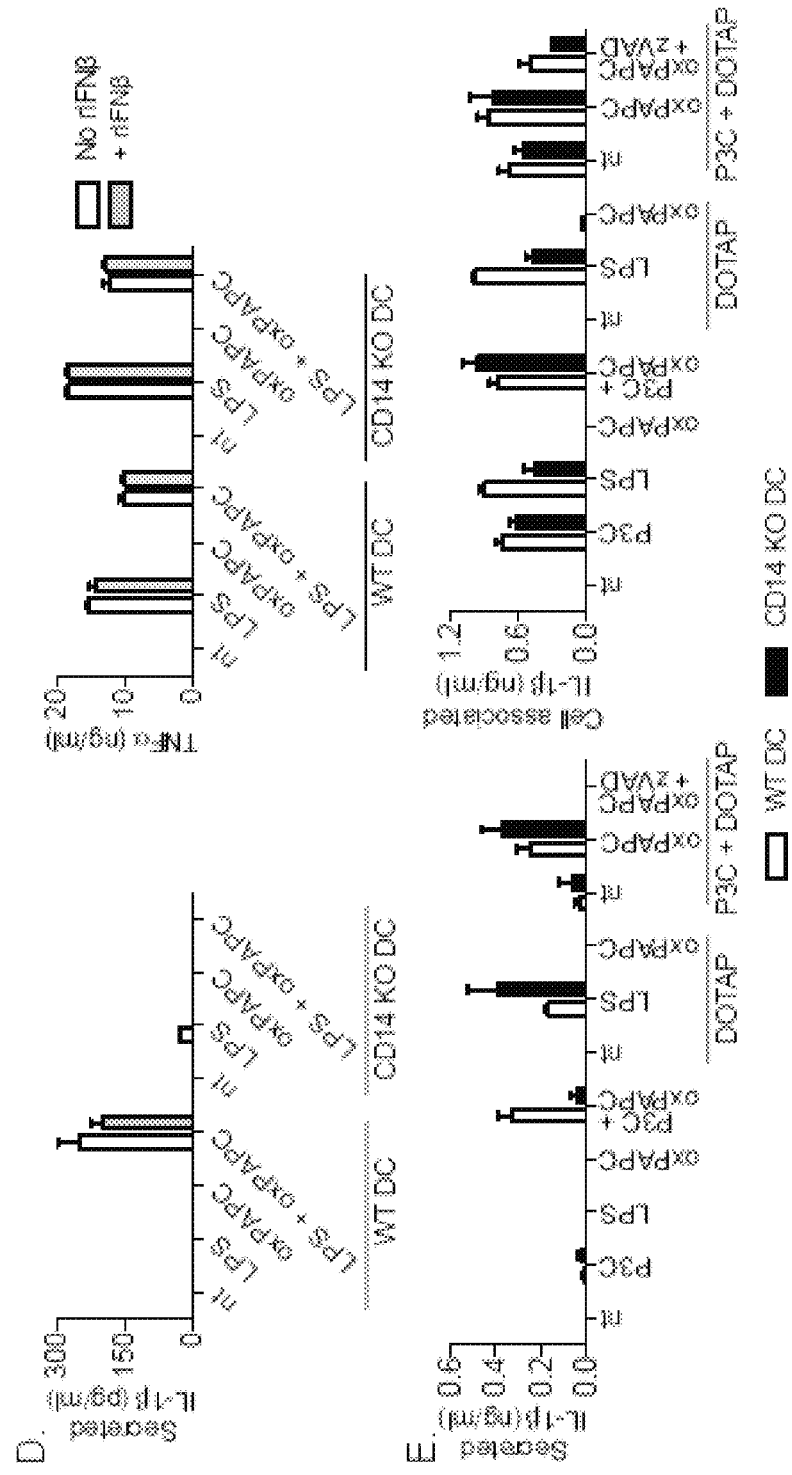

Figures 48A-D
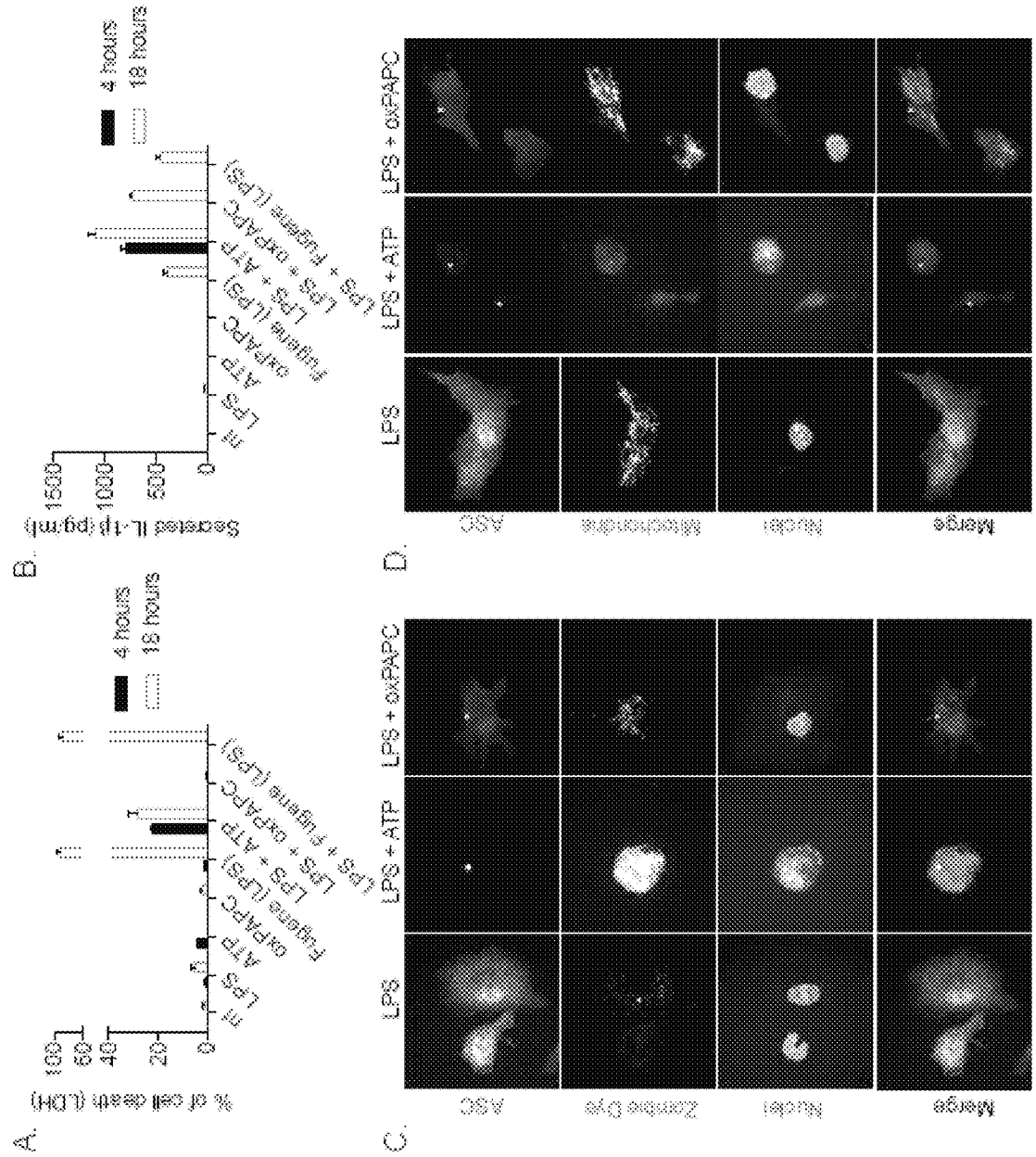

Figures 48E-G
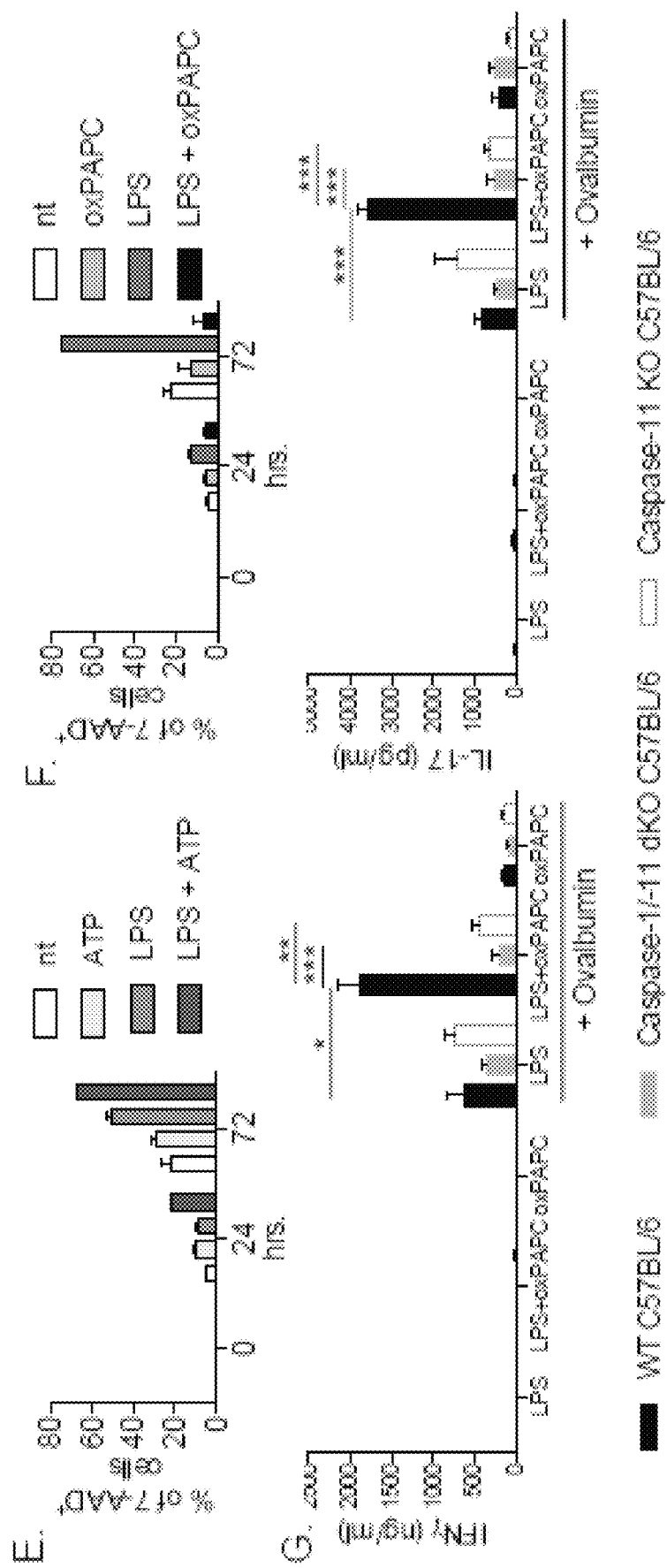

Figures 49A-B
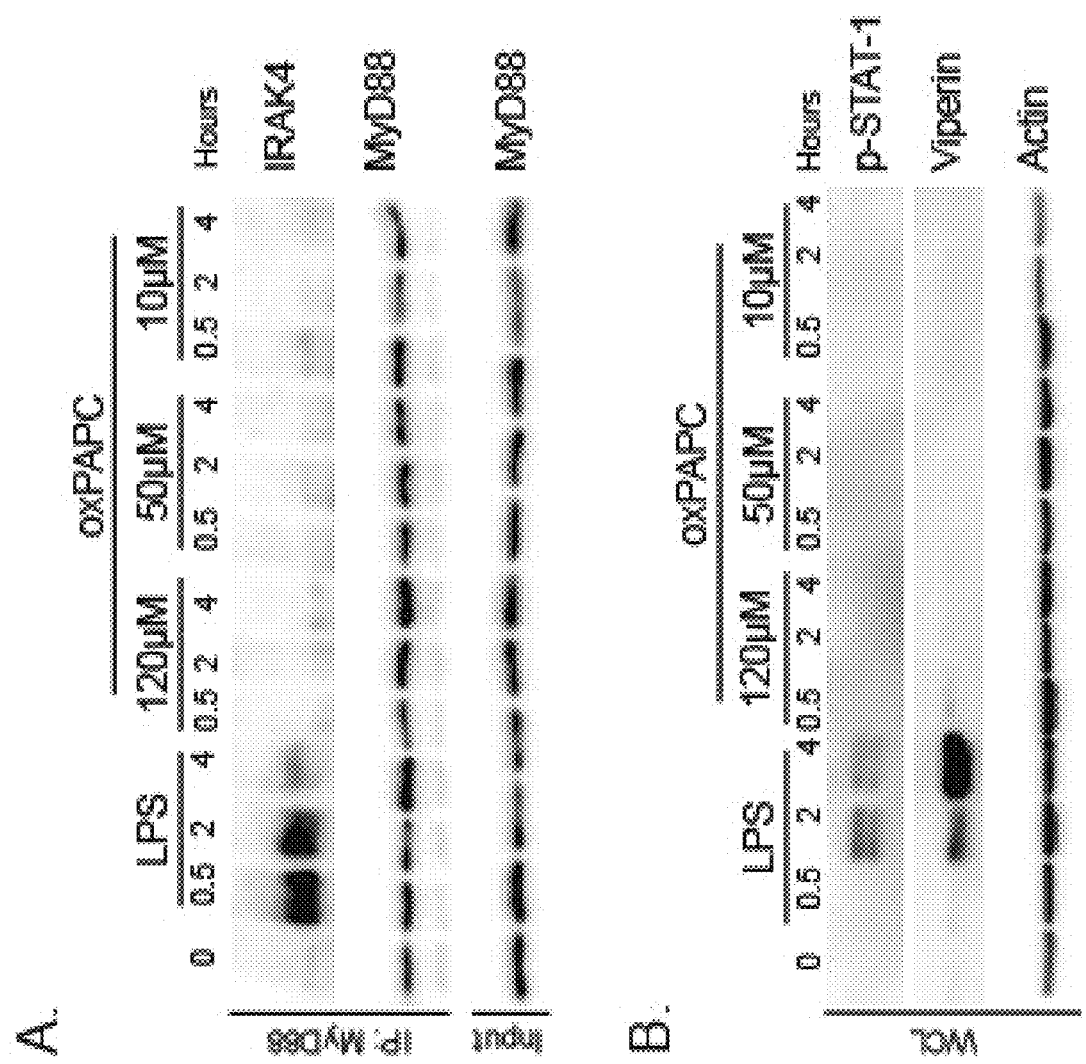

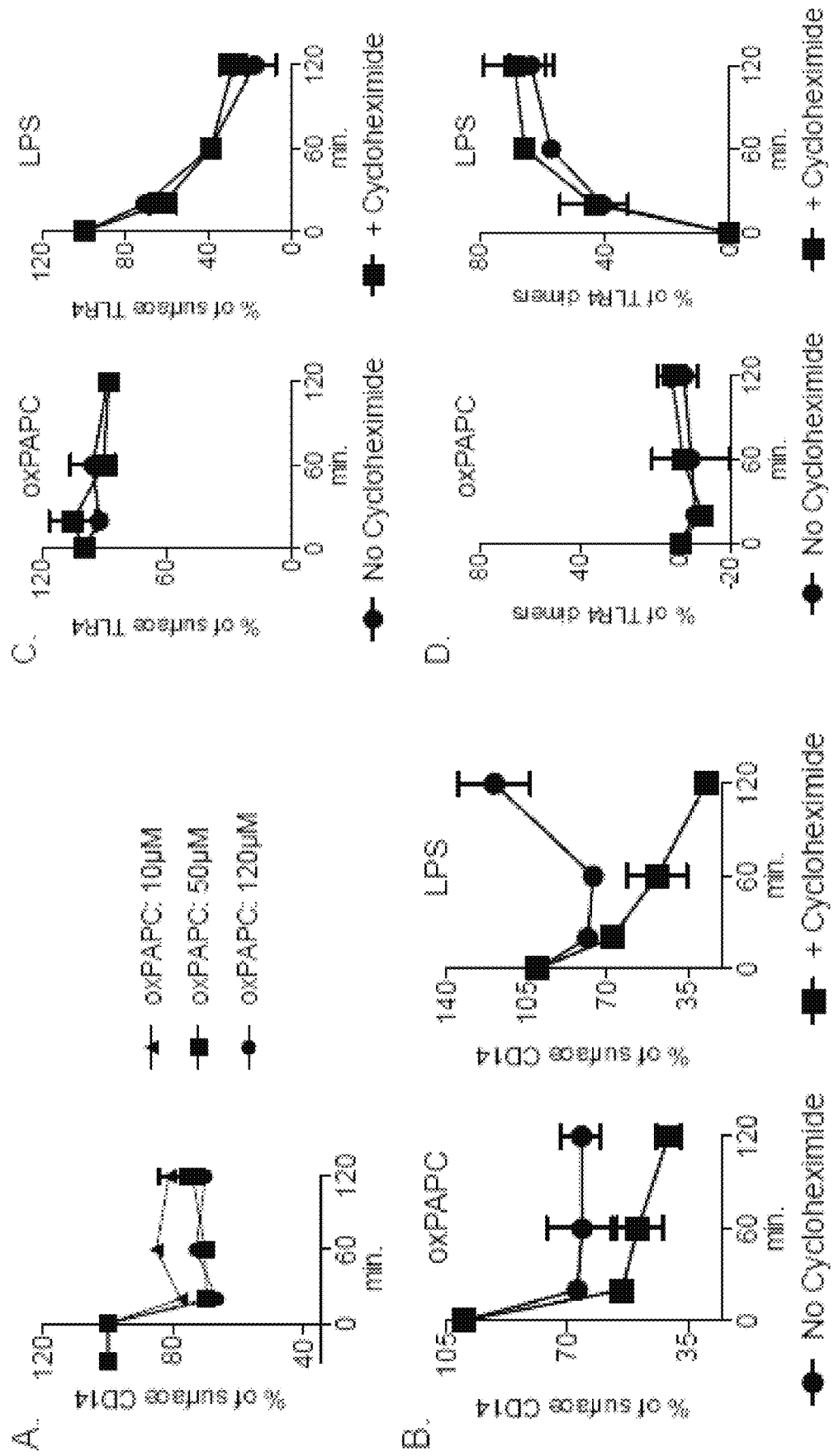
Figures 50A-D

Figures 51A-E
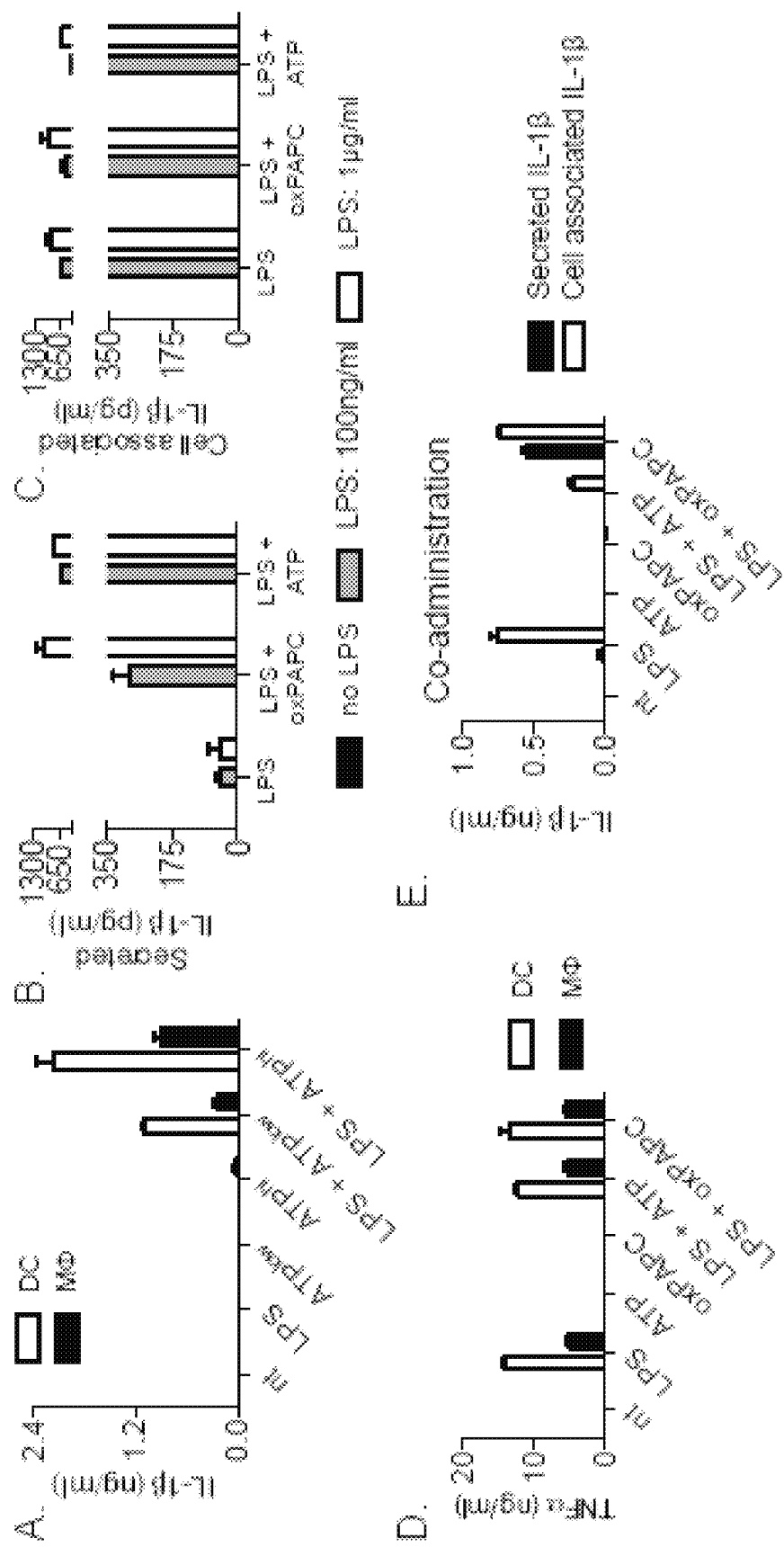

Figures 51F-I
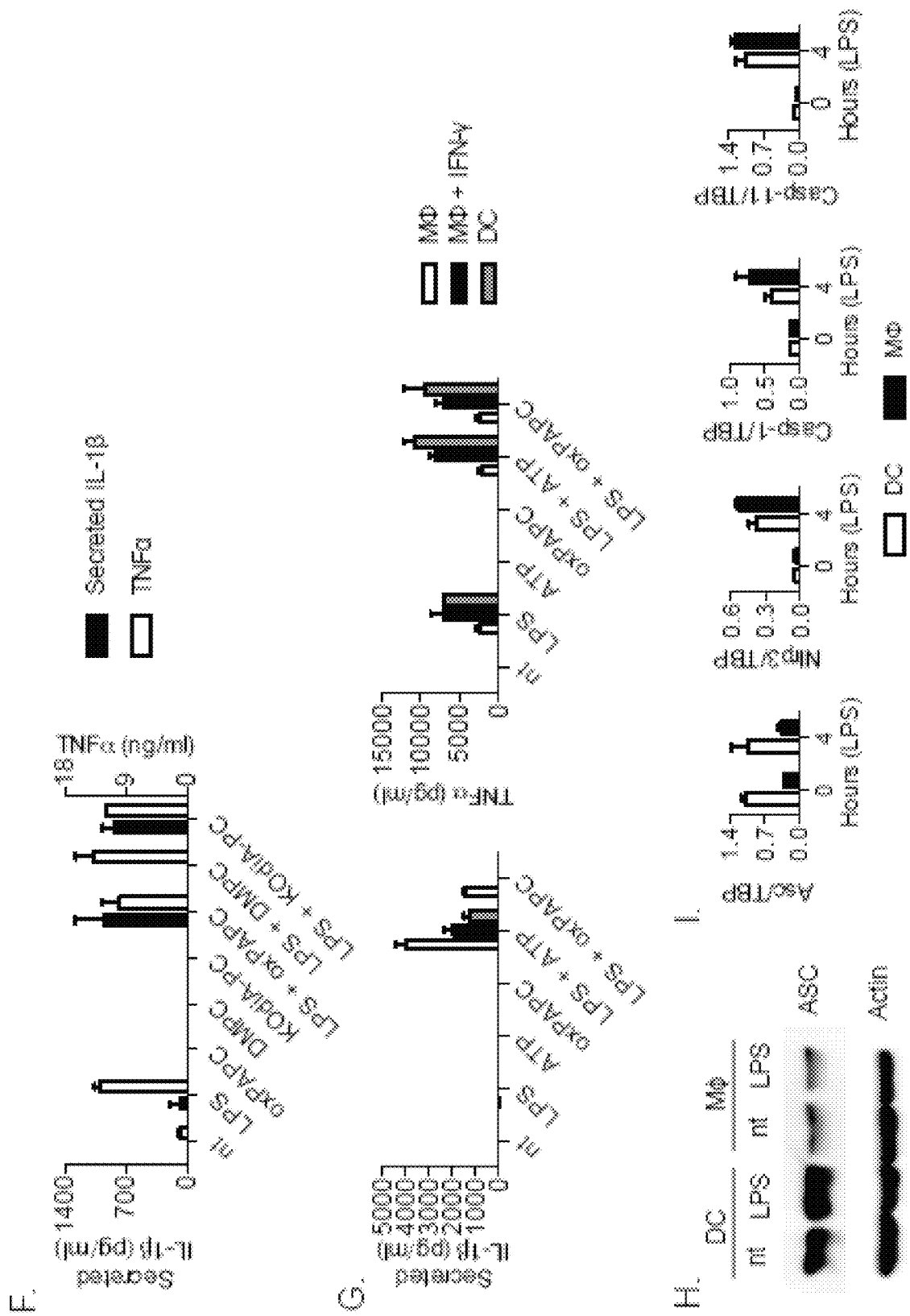

Figures 52A-C
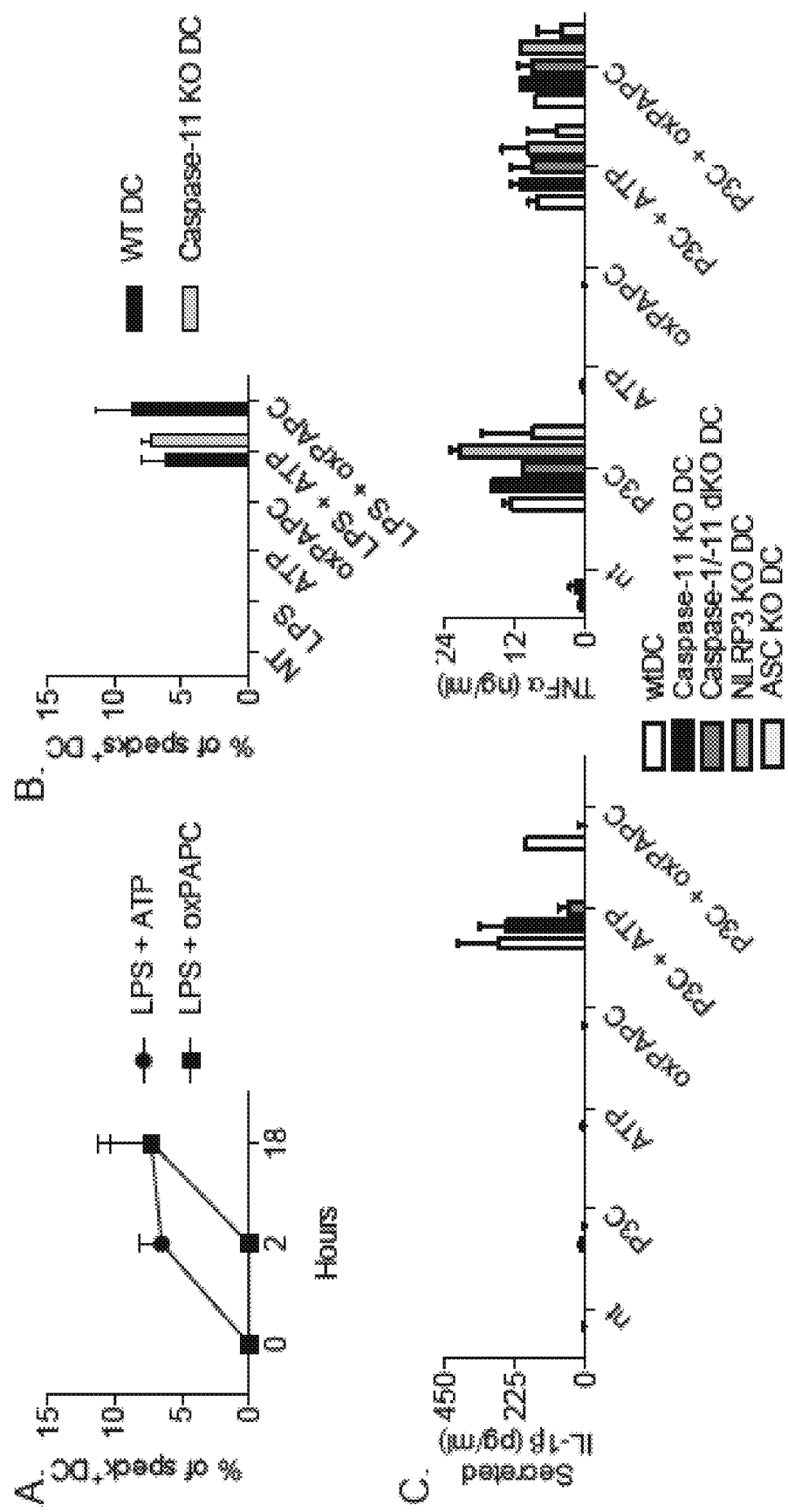

Figures 52D-I
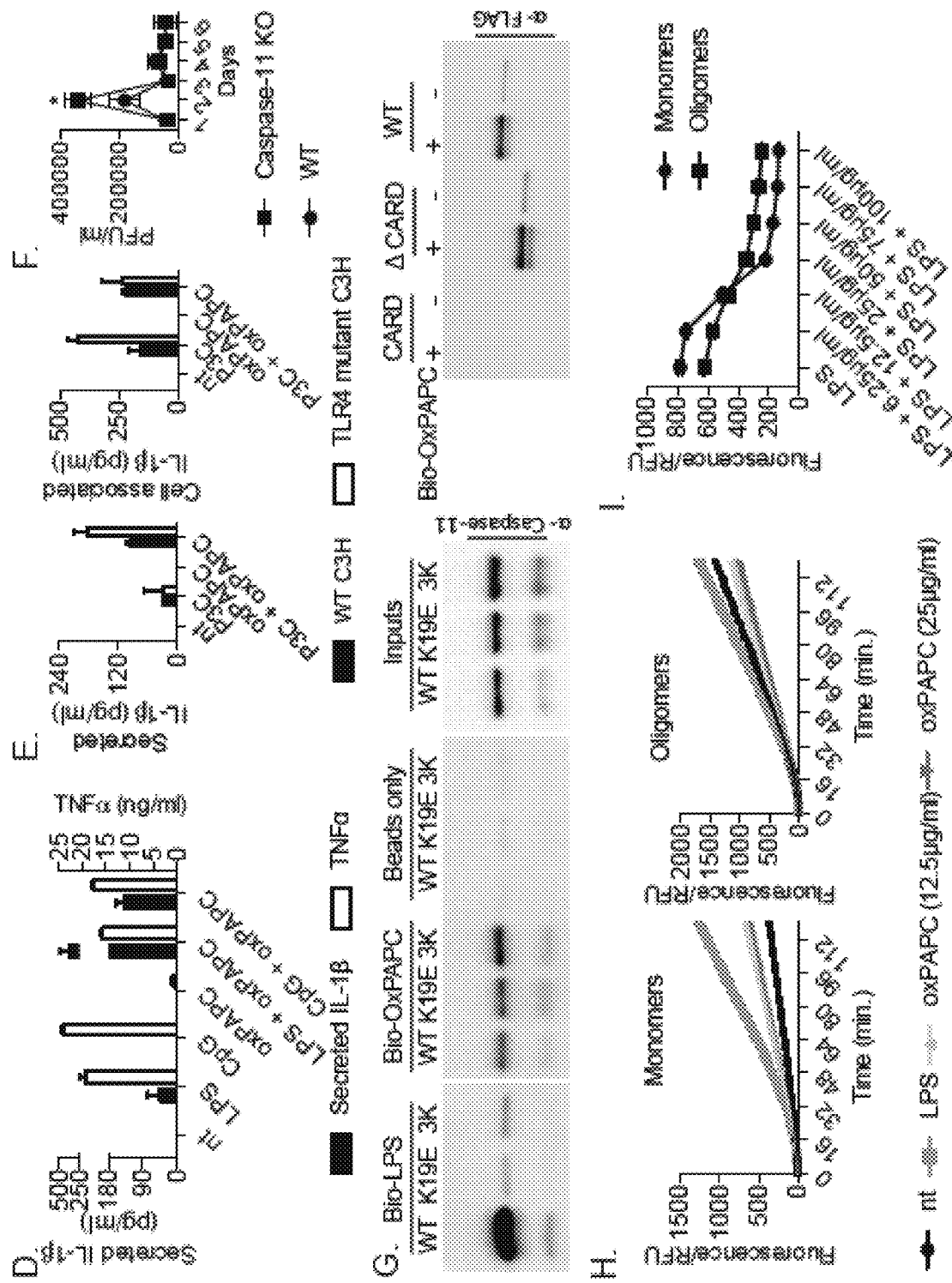

Figures 53A-B
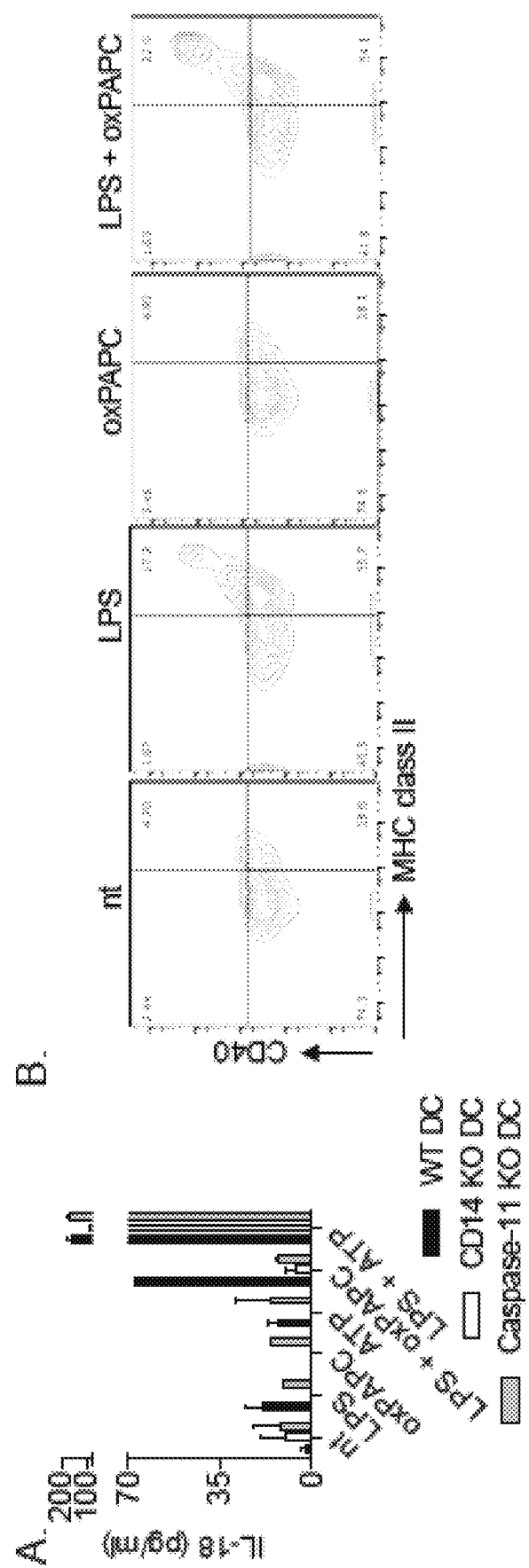

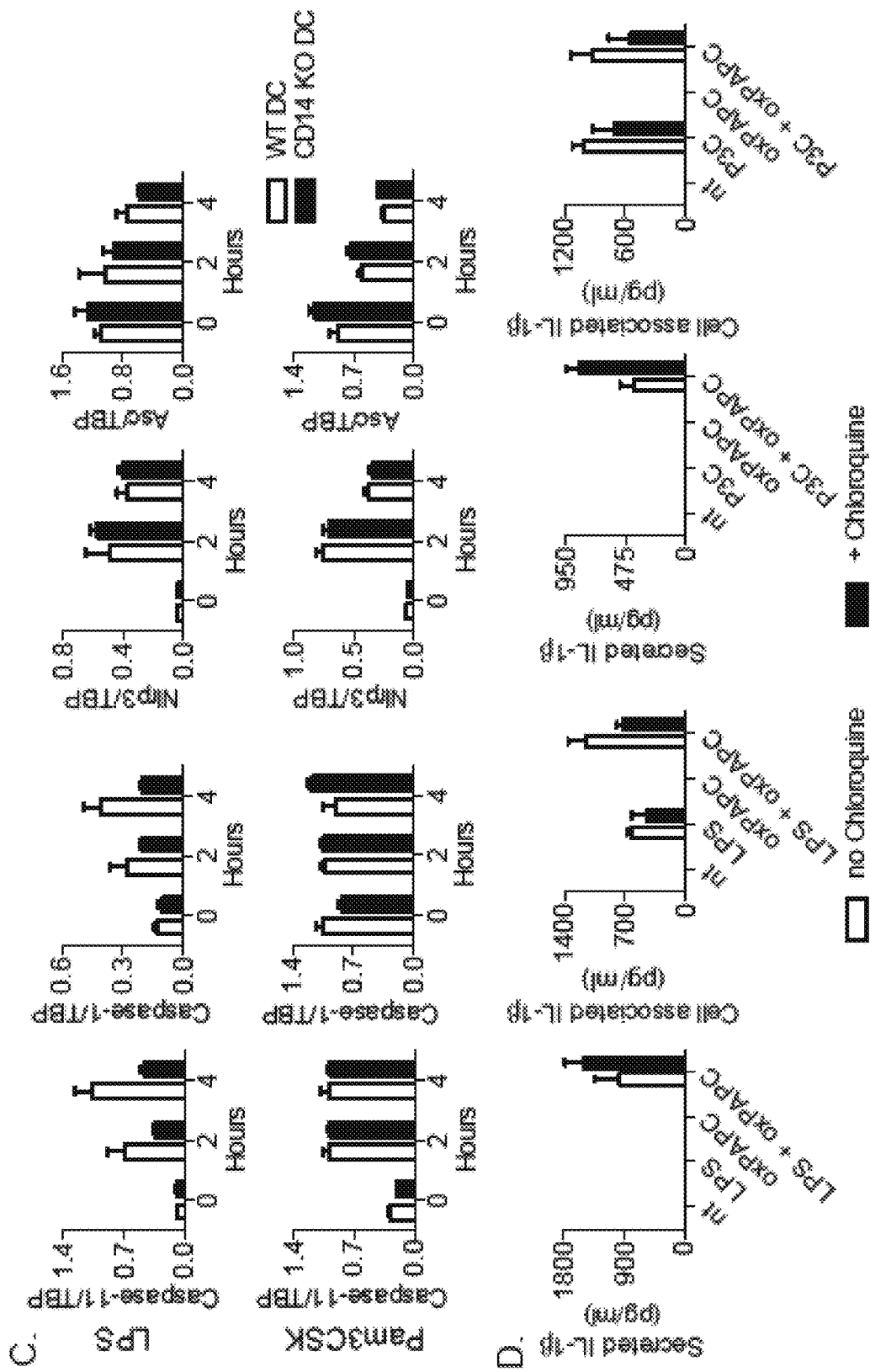
Figures 53C-D

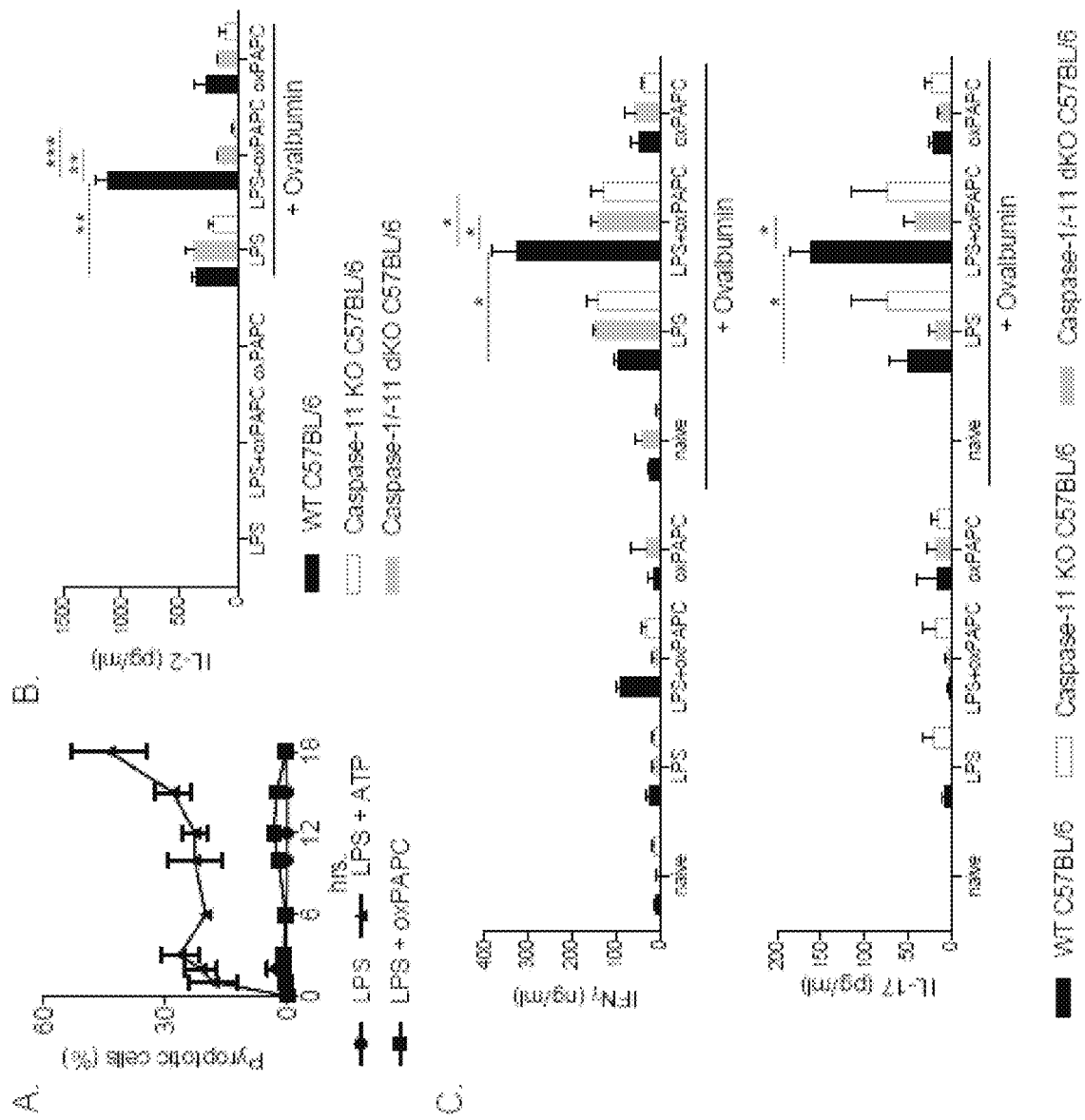
Figures 54A-C

PRO-INFLAMMATORY AND ANTI-CANCER FUNCTIONS OF TOLL-LIKE RECEPTOR 4 ANTAGONISTS

CROSS-REFERENCE TO RELATED APPLICATION

This application is a continuation of U.S. patent application Ser. No. 15/543,165, filed on Jul. 12, 2017, which is a National Phase application filed under 35 U.S.C. § 371 of International Patent Application No. PCT/US2016/012994 with an International Filing Date of Jan. 12, 2016, which claims the benefit of priority under 35 U.S.C. § 119(e) to U.S. Provisional Application No. 62/102,245, filed Jan. 12, 2015 and entitled, "Pro-Inflammatory and Adjuvant Functions of Toll-Like Receptor 4 Antagonists." The entire content of the foregoing are incorporated herein by reference.

STATEMENT OF RIGHTS TO INVENTIONS MADE UNDER FEDERALLY SPONSORED RESEARCH

This invention was made with government support under grant number AI103082-01A1, awarded by the National Institutes of Health. The government has certain rights in the invention.

FIELD OF THE INVENTION

The invention relates generally to the fields of adjuvants, immunostimulation and vaccines.

BACKGROUND OF THE INVENTION

The ability to distinguish self from non-self molecules is a fundamental feature of all forms of life, yet our understanding of this distinction remains incomplete. In mammals, it is commonly believed that the Pattern Recognition Receptors (PRRs) of the innate immune system serve the function of distinguishing self and non-self molecules. This idea, first put forth by Charles Janeway Jr., has been extensively validated through the study of various families of PRRs, such as the Toll-like Receptors (TLRs), RIG-I like Receptors (RLRs), NOD-like Receptors (NLR) and C-type Lectin Receptors (CLRs) (Iwasaki, A., and Medzhitov, R. (2015) Nat Immunol 16, 343-353). PRRs act to either directly or indirectly detect molecules that are common to broad classes of microbes. These molecules are classically referred to as pathogen associated molecular patterns (PAMPs), and include factors such as bacterial lipopolysaccharides (LPS), bacterial flagellin or viral double stranded RNA, among others (Janeway, C. A., Jr. (1989) Spring Harb Symp Quant Biol 54 Pt 1, 1-13). Detection of microbial products activates PRR-dependent cellular responses that are either pro-inflammatory or immuno-regulatory, with the best example of the latter being the activation of antigen-specific T-cells to promote adaptive immunity (Iwasaki, A., and Medzhitov, R. (2015) Nat Immunol 16,343-353). PRR-mediated pro-inflammatory responses can be considered those that occur in numerous types of cells, whereas activities designed to promote T-cell activation often occur uniquely in dendritic cells (DCs). DC-specific activities induced by PRRs include the acidification of endosomes and phagosomes (Delamarre, L. et al., (2005) Science 307, 16301634, and Trombetta, E. S. et al., (2003) Science 299, 1400-1403), delivery of major histocompatibility complex (MHC) molecules to microbe-containing phagosomes (Nair-Gupta, P. et al. (2014) Cell 158, 506521), loading of microbial peptides on MHC, and delivery of MHC molecules to the cell surface (Blander, J. M., and Medzhitov, R. (2006). Nature 440, 808-812; Inaba, K. et al., (2000) J Exp Med 191, 927-936; Pierre, P. et al., (1997) Nature 388, 787-792; Turley, S. J. et al., (2000) Science 288, 522-527). All of these activities promote effective antigen presentation to T-cells and the initiation of adaptive immunity.

Adjuvants are substances that accelerate and/or enhance an antigen specific immune response. The purpose of an adjuvant is to make an antigen visible to the eyes (macrophages/dendritic cells) of the immune system. Recognition of antigens by antigen presenting cells (APCs) such as macrophages and dendritic cells essentially initiates the critical cascade of events leading to localized inflammation, which recruits APCs and ultimately leads to initiation of a productive cell mediated and/or antibody mediated immune response. Currently, the majority of human vaccines contain aluminum salts as an adjuvant and pharmaceutical companies are developing oil-based adjuvants to be incorporated into vaccines. For development of improved immunostimulatory compositions (e.g., vaccines), identification and inclusion of adjuvants that selectively activate dendritic cells (DC) while minimally activating macrophages would be beneficial in reducing adverse side effects of administering such compositions, such as malaise and inflammation. Currently, adjuvants which act as agonists to TLR-2, TLR-5, TLR7/8, and TLR-9 are being studied, and one TLR-4 agonist, monophosphoryl lipid A, is FDA approved.

SUMMARY OF THE INVENTION

The invention is based, at least in part, upon the discovery that endogenous oxidized phospholipids, which are Toll-like Receptor (TLR) antagonists that are found at sites of tissue damage, created a dendritic cell state that was hyper-inflammatory. It was specifically demonstrated that, in a context-dependent manner, oxPAPC induced several responses within DCs that promoted their ability to activate antigen specific T-cells. These findings indicated that phospholipids such as oxPAPC (and related phospholipids capable of activating non-canonical inflammasomes, as well as, e.g., Rhodo LPS, which was also found to activate non-canonical inflammasomes) could function as an enhanced class of adjuvants for use in prophylactic and therapeutic immunostimulatory compositions.

In the presence of diverse TLR ligands, oxPAPC was identified to promote DC survival and trigger the release of the T-cell activating cytokine interleukin 1 beta (IL-1β). Mechanistically, oxPAPC was characterized as engaging the LPS receptor CD14 on the surface of DCs, which allowed its delivery into endosomes and subsequent access to the cytosolic protein caspase-11. Caspase-11 engagement by oxPAPC triggered the inflammasome-mediated release of IL-1β. These oxPAPC-triggered responses did not occur in macrophages, indicating that the actions of this lipid were uniquely designed to promote immuno-regulatory activities of DCs, as opposed to general (macrophage-mediated) inflammatory responses. Consequently, oxPAPC was identified to synergize with microbial products to induce a more robust activation of antigen specific T-cells than could be elicited by PAMPs alone. These molecules, (dubbed vita-DAMPs), were identified as functioning together with PAMPs to hyperactivate DCs and elicit maximal adaptive immune responses.

In one aspect, the invention provides a composition for eliciting an immune response to an immunogen that includes an immunogen and a non-canonical inflammasome-activating lipid.

In one embodiment, the non-canonical inflammasome-activating lipid is oxPAPC. In another embodiment, the non-canonical inflammasome-activating lipid is PAPC. Optionally, the non-canonical inflammasome-activating lipid is one or more species of oxPAPC. In a related embodiment, the non-canonical inflammasome-activating lipid is one or more of HOdiA-PC, KOdiA-PC, HOOA-PC and KOOA-PC. In another embodiment, the non-canonical inflammasome-activating lipid is Rhodo LPS.

In an additional embodiment, the non-canonical inflammasome-activating lipid enhances an immune response to the immunogen when the composition is administered to a subject, as compared to a composition lacking the non-canonical inflammasome-activating lipid.

In one embodiment, the immunogen and lipid are present at a concentration sufficient to induce dendritic cell (DC) activation when the composition is administered to a subject.

Optionally, the composition does not elicit a macrophage inflammatory response when administered to a subject.

In one embodiment, the immunogen includes a human papilloma virus antigen, a herpes virus antigen such as herpes simplex antigen or herpes zoster antigen, a retrovirus antigen such as human immunodeficiency virus 1 antigen or human immunodeficiency virus 2 antigen, a hepatitis virus antigen, an influenza virus antigen, a rhinovirus antigen, respiratory syncytial virus antigen, cytomegalovirus antigen, adenovirus antigen, *Mycoplasma pneumoniae* antigen, an antigen of a bacterium of the genus *Salmonella, Staphylococcus, Streptococcus, Enterococcus, Clostridium, Escherichia, Klebsiella, Vibrio, Mycobacterium*, an amoeba antigen, a malarial parasite antigen and/or a *Trypanosoma cruzi* antigen.

Optionally, the composition is lyophilized.

In another embodiment, the composition consists essentially of the immunogen in combination with the non-canonical inflammasome-activating lipid.

Another aspect of the invention provides a pharmaceutical composition that includes an immunogen-adjuvant composition of the invention and a pharmaceutically acceptable carrier.

In one embodiment, the carrier is an aqueous carrier. In another embodiment, the carrier is a solid carrier.

A further aspect of the invention provides a method for inducing an inflammatory response in a dendritic cell of a subject that includes administering the composition of claim 1 to the subject.

An additional aspect of the invention provides a method for enhancing a protective immune response to an immunogen in a subject, by administering the immunogen and anon-canonical inflammasome-activating lipid to a subject in an amount effective to enhance a protective immune response in the subject, where the non-canonical inflammasome-activating lipid is administered in an adjuvant-effective amount.

In one embodiment, the immunogen and the non-canonical inflammasome-activating lipid are administered concurrently to the subject.

Another aspect of the invention provides a method of inducing an immune response in a subject that includes concurrently administering an immunogen and a non-canonical inflammasome-activating lipid to the subject in an amount effective to produce an immune response in the subject.

In one embodiment, the subject is human.

In another embodiment, the immunogen and the non-canonical inflammasome-activating lipid are administered simultaneously in a common pharmaceutical carrier.

Optionally, the immunogen and the non-canonical inflammasome-activating lipid are administered by parenteral administration.

In one embodiment, the immune response is a prophylactic immune response.

In another embodiment, the immune response is a therapeutic immune response.

In an additional embodiment, the immune response includes a humoral immune response.

Other aspects of the invention are described in, or are obvious from, the following disclosure, and are within the ambit of the invention.

BRIEF DESCRIPTION OF THE DRAWINGS

FIG. 6 shows that PAPCs activated the inflammasome in DCs.

FIG. 8 shows that CD14 regulated inflammasome activation in response to PAPCs.

FIGS. 43A-43D depict images showing that oxPAPC did not bind TLR4 or induce TL4F signaling. FIG. 43A presents a line graph showing the extent of TLR4 dimerization in iMΦs treated with LPS (1 μg/ml) or oxPAPC (50 μM) for the indicated time points. TLR4 dimerization was measured by flow cytometry. The line graph represents means and standard deviations of two independent experiments. FIG. 43B depicts a line graph showing IL-1β, IL-6, IFNβ and Viperin levels in iMΦs treated with LPS (1 μg/ml) or oxPAPC (50 μM). Gene expression relative to GAPDH was analyzed by qPCR at times indicated. Untreated cells were used as a negative control in all experiments. Line graphs represent the average and error bars represent the standard deviation of triplicate readings from one representative experiment of three. FIG. 43C depicts a blot showing myddosome formation in iMΦs at the indicated time points after treatment with LPS (1 μg/ml) or oxPAPC (50 μM) by co-immunoprecipitation (IP) of IRAK4 with MyD88 followed by Western analysis of the proteins indicated. FIG. 43D depicts a blot showing whole cell lysates (WCL) collected and DCs monitored for STAT-1 phosphorylation and viperin expression after treatment with LPS (1 μg/ml) or oxPAPC (50 μM).

FIGS. 44A-44F depict images showing that oxPAPC acted as both a CD14 agonist and a TLR4 antagonist. FIG. 44A depicts a line graph indicating surface levels of CD14 and TLR4 in iMΦ lines treated with LPS (1 g/ml) or oxPAPC (50 μM) for the indicated times. Surface levels of CD14 and TLR4 were measured by flow cytometry. Line graphs represent means and standard deviations of two independent experiments. FIG. 44B depicts a line graph indicating results for primary DCs and MΦs treated with oxPAPC (50 μM) for the indicated times. Surface levels of CD14 and TLR4 and TLR4 dimerization were measured by flow cytometry. Line graphs represent means and standard deviations of two independent experiments. FIG. 44C depicts a line graph indicating results for iMΦs treated with LPS alone (1 μg/ml), oxPAPC alone (at the indicated concentration) or pre-treated with oxPAPC for 30' and then with LPS. Surface levels of TLR4 and TLR4 dimerization were measured by flow cytometry. Line graphs represent means and standard deviations of biological duplicates from one experiment representative of three. FIG. 44D depicts images showing results for iMΦs treated with LPS alone (at the indicated concentrations), oxPAPC alone (120 μM) or pre-treated with oxPAPC for 30' and then with LPS. FIG. 44D (left panel) shows TNFα secretion measured 18 hours after LPS stimulation by ELISA. Line graphs represent the average and error bars represent the standard deviation of triplicate readings from one representative experiment of three. FIG. 44D (right panels) shows STAT-1 phosphorylation measured 4 hours after LPS treatment by Western analysis. FIG. 44E depicts a blot showing the oxPAPC binding capacity of the CD14 mutants was determined by biotinylated oxPAPC pull down assay. Lysates of 293T cells expressing the indicated CD14 mutants were incubated with biotinylated oxPAPC (10 μg). CD14-oxPAPC complex was then captured using neutravidin beads. The amount CD14 retained by oxPAPC was determined by Western analysis. The CD14 mutant with 26DEES29 mutagenized into 26AAAA29 was designated as CD14 1R. The CD14 mutant with 26DEES29 and 37PKPD40 mutagenized into 26AAAA29 and 37AAAA40 was designated as CD14 2R. The CD14 mutant with 26DEES29, 37PKPD40, 52DVE54 and 74DLGQ77 mutagenized into 26AAAA29, 37AAAA40, 52AAA54 and 74AAAA77 was designated as CD14 4R. FIG. 44F presents a graph showing that the 4R CD14 mutant was not internalized in response to oxPAPC or LPS treatments. Indicated iMΦ lines were treated with LPS (1 μg/ml) or oxPAPC (50 μM) for the indicated times. Surface levels of CD14 were measured by flow cytometry. Line graph represents the average and error bars represent the standard deviation of biological duplicates from one representative experiment of three.

FIGS. 45A-45G present images showing that oxPAPC induced the activation of NLRP3 inflammasome in DCs. FIG. 45A depicts bar graphs showing IL-1β secretion results for DCs treated with LPS alone (1 μg/ml), three doses oxPAPC (10, 50, 120 μM) or primed with LPS for 3 hours and then treated with oxPAPC. For this experiment, commercially available oxPAPC and an oxPAPC enriched in PEIPC were used. 18 hours after LPS administration, secreted (left panel) and cell associated (right panel) IL-1β were measured by ELISA. Means and standard deviations of biological duplicates from one experiment representative of two are shown. FIGS. 45B-45D depict bar graphs showing results for WT DC or caspase-1 KO and caspase-1/-11 dKO DCs (FIG. 45B), ASC KO DC (FIG. 45C) and NLRP3 KO DC (FIG. 45D) treated with LPS alone (1 µg/ml), oxPAPC alone (120 µM) or primed with LPS for 3 hours and then treated with oxPAPC. 18 hours after LPS administration, IL-1β (left panel) and TNFα (right panel) secretion was measured by ELISA. Means and standard deviations of two independent experiments are shown. FIG. 45E depicts bar graphs depicting IL-1β secretion results for MΦs treated with LPS alone (1 µg/ml), three different doses oxPAPC (10, 50, 120 µM) or primed with LPS for 3 hours and then treated with oxPAPC. For this experiment, commercially available oxPAPC and an oxPAPC enriched in PEIPC were used. 18 hours after LPS administration, secreted (left panel) and cell associated (right panel) IL-1β were measured by ELISA. Means and standard deviations of biological duplicates from one experiment representative of two are shown. FIG. 45F depicts a bar graph showing IL-1β secretion results for MΦs treated with Pam3CSK (P3C) alone (1 µg/ml), oxPAPC alone (120 µM), ATP alone (5 mM) or primed with Pam3CSK for 3 hours and then treated with oxPAPC, ATP, DOTAP, LPS (5 µg) or oxPAPC encapsulated in DOTAP. 18 hours after P3C administration, IL-1β was measured by ELISA. Means and standard deviations of three replicates of one experiment of two are shown. FIG. 45G depicts bar graphs showing that LPS-primed DCs and MΦs showed intrinsic differences in their response to NLRP3 activation after ATP treatment. DCs (left panel) or MΦs (right panel) were primed with LPS (1 µg/ml) for three hours and treated with ATP (3 mM). At indicated time points, IL-1β was measured by ELISA and cell death was measured by PI permeabilization assay. Means and standard deviations of four replicates of one representative experiment of three are shown.

FIGS. 46A-46G show oxPAPC non-canonical inflammasome activation. FIG. 46A presents a bar graph showing IL-1β secretion results for WT DC and caspase-11 KO DC treated with LPS alone (1 µg/ml), oxPAPC alone (120 µM) or primed with LPS for 3 hours and then treated with oxPAPC. 18 hours after LPS administration, IL-1β secretion was measured by ELISA. Means and standard deviations of two independent experiments are shown. FIG. 46B depicts a bar graph showing TNFα secretion results for WT DC and caspase-11 KO DC treated with LPS alone (1 µg/ml), oxPAPC alone (120 µM) or primed with LPS for 3 hours and then treated with oxPAPC. 18 hours after LPS administration, TNFα secretion was measured by ELISA. Means and standard deviations of two independent experiments are shown. FIG. 46C depicts images showing that LPS-primed DCs formed specks in a caspase-11-dependent manner in response to oxPAPC but not ATP. DCs were left untreated or primed with LPS (1 µg/ml) for three hours and then stimulated with ATP (1 mM) or oxPAPC (120 µM). Specks containing ASC (green) and caspase-1 (Casp1, red) were analyzed 18 hours after LPS stimulation. Nuclei are shown in blue. Panels are representative of four independent experiments. FIG. 46D depicts blots showing that endogenous caspase-11 associated with oxPAPC in vitro. S100 fractions (0.5 mg) of nontreated (nt) or P3C-primed (P3C) MΦs were incubated with biotinylated LPS (Bio-LPS) or biotinylated-oxPAPC (Bio-oxPAPC). Endogenous proteins associated with biotinylated-lipids were captured by streptavidin beads and revealed by Western analysis. Shown is a representative blot out of three independent experiments. FIG. 46E shows graphs of the SPR analysis of the interactions between the proteins and indicated lipids. FIG. 46F depicts a graph showing the gel filtration analysis of the size of caspase-11 complexes before and after exposure to oxPAPC. Complex size was monitored by A280 or Western analysis, as indicated. FIG. 46G depicts bar graphs showing secretion and viability results for bone marrow cells infected with the pMSCV2.2-IRES-GFP vector (empty), the pMSCV2.2-IRES-GFP vector encoding WT caspase-11 (WT caspase-11) or the same vector containing a catalytic mutant caspase-11 (C254A). After seven days of differentiation in GM-CSF containing medium, DCs were primed or not with LPS (1 µg/ml) for three hours and then stimulated with oxPAPC (120 µM), or transfected with LPS-containing FuGENE (LPS, 5 µg). 18 hours after LPS priming, supernatant were collected and IL-1β and TNFα secretion was measured by ELISA. Cell viability was assessed by measuring LDH release.

FIGS. 47A-47E depict bar graphs showing that CD14 promoted caspase-11 mediated IL-1 release from DCs. FIG. 47A depicts bar graphs showing secretion results for WT DCs and CD14KO DCs treated with LPS alone (1 µg/ml), Pam3CSK (P3C) alone (1 g/ml), oxPAPC alone (120 µM) or primed with LPS or with Pam3CSK for 3 hours and then treated with oxPAPC. 18 hours after LPS or P3C administration, IL-1β and TNFα secretion was measured by ELISA. Means and standard deviations of two independent experiments are shown. FIG. 47B depicts bar graphs showing IL-1β and TNFα secretion results for spleen-derived WT DCs, CD14 KO DCs, and caspase-11 KO DCs treated with LPS alone (1 µg/ml), ATP alone (1.5 mM), oxPAPC alone (120 µM) or primed with LPS for 3 hours and then treated with oxPAPC or ATP. 18 hours after LPS administration, IL-1β and TNFα secretion was measured by ELISA. Means and standard deviations of two replicates of one representative experiment of three are shown. FIG. 47C depicts bar graphs showing gene expression results for WT DCs and CD14 KO DCs treated with LPS or Pam3CSK. Gene expression relative to TBP was analyzed by qPCR at times indicated. Results are shown as gene expression compared to untreated cells. Line graphs represent the average of triplicate readings from one representative experiment of three. FIG. 47D depicts bar graphs showing IL-1β and TNFα secretion results for WT DC and CD14 KO DC treated with LPS alone (1 µg/ml), oxPAPC alone (120 µM) or primed with LPS for 3 hours and then treated with oxPAPC in the presence or the absence of rIFNβ (100 U/ml). 18 hours after LPS administration, IL-1β and TNFα secretion was measured by ELISA. Means and standard deviations of two independent experiments are shown. FIG. 47E depicts bar graphs showing IL-1β secretion results for WT DC and CD14 KO DCs treated with LPS alone (1 µg/ml), Pam3CSK (P3C) alone (1 µg/ml), oxPAPC alone (120 µM) or primed with Pam3CSK for 3 hours and then treated with oxPAPC. As indicated, LPS or oxPAPC were complexed with DOTAP before addition to the cell culture. Where indicated, cells where treated with the pan-caspase inhibitor zVAD 30 min before addition of the DOTAP/oxPAPC complex to the culture. 18 hours after stimuli administration, IL-1β secretion was measured by ELISA. Means and standard deviations of two independent experiments are shown.

FIGS. 48A-48G depict images showing that oxPPAC acted like a natural adjuvant, preventing DC death and potentiating adaptive immune responses. FIG. 48A depicts a bar graph showing viability results for DCs treated with LPS alone (1 µg/ml), ATP alone (1 mM), oxPAPC alone (120 µM) or FuGENE complexed LPS (5 µg) (Fugene (LPS)), or primed for three hours with LPS (1 µg/ml) and then treated with the indicated stimuli. 4 and 18 hours after LPS priming, cell death was measured by LDH release. FIG. 48B depicts a bar graph showing IL-1β secretion results for DCs treated with LPS alone (1 μg/ml), ATP alone (1 mM), oxPAPC alone (120 μM) or FuGENE complexed LPS (5 μg) (Fugene (LPS)), or primed for three hours with LPS (1 μg/ml) and then treated with the indicated stimuli. 4 and 18 hours after LPS priming, IL-1β secretion was measured by ELISA. FIGS. 48C-48D depict images showing staining results for DCs pretreated with LPS for 3 hours (1p g/ml) and then activated with ATP (1 mM) or oxPAPC (120 μM). 18 hours later, cells were stained for ASC (green), nuclei (blue) Zombie Dye (red) (FIG. 48C) or active mitochondria (red) (FIG. 48D). Panels are representative of three independent experiments. FIGS. 48E-48F depict bar graphs showing viability results for DCs treated with LPS alone (1 μg/ml), oxPAPC alone (120 μM), ATP alone (1 mM) or primed with LPS for 3 hours and then treated with oxPAPC or ATP. At the indicated time points, cell viability was measured by 7-AAD staining. Means and standard deviations of two independent experiments are shown. FIG. 48G depicts bar graphs showing that oxPAPC potentiated memory T cell responses in vivo. CD4+ T-cells were isolated from the draining lymph nodes 40 days after immunization with OVA+LPS in IFA (LPS), OVA+LPS+oxPAPC in IFA (LPS+oxPAPC) or OVA+oxPAPC in IFA (oxPAPC) of WT, caspase-1/-11 dKO or caspase-11 KO mice. CD4+ T-cells were restimulated or not with OVA in the presence of DCs. IFNγ (left panel) and IL-17 (right panel) secretion was measured 5 days later by ELISA. Bar graphs represent means and standard errors of two experiments with five animals per group.

FIGS. 49A-49B depict blots showing that oxPAPC did not induce myddosome formation or type I IFN signaling (related to FIGS. 43A-43D). FIG. 49A presents a blot showing myddosome formation in iMΦs assessed at the indicated time points after treatment with LPS (1 μg/ml) or different doses of oxPAPC (10, 50, 120 μM) by co-immunoprecipitation of IRAK4 with MyD88 followed by Western analysis for the proteins indicated. FIG. 49B depicts a blot showing whole cell lysates (WCL) collected from DCs and monitored by Western analysis for the proteins indicated after treatment with LPS (1 μg/ml) or different doses of oxPAPC (10, 50, 120 μM).

FIGS. 50A-50D depict graphs showing that oxPAPC was an agonist for CD14 but not for TLR4 (see also FIGS. 44A-44F). FIG. 50A depicts a bar graph showing surface CD14 results for DCs treated with oxPAPC at the indicated concentrations. Surface levels of CD14 were measured by flow cytometry. Line graphs represent means and standard deviations of two independent experiments. FIGS. 50B-50D depict bar graphs showing surface CD14, TLR4 and TLR4 dimerization results for DCs treated with LPS (1 μg/ml) or oxPAPC (120 μM) for the indicated times in the presence or absence of cycloheximide (100 μg/ml). Surface levels of CD14 (FIG. 50B), TLR4 (FIG. 50C) and TLR4 dimerization (FIG. 50D) were measured by flow cytometry. Line graphs represent means and standard deviations of two independent experiments.

FIGS. 51A-51I depict images showing that oxPAPC induced IL-1β release in a cell-type specific manner (see also FIGS. 45A-G). FIG. 51A depicts a bar graph showing that DCs and iMΦs released IL-1β in response to ATP. Freshly derived DCs and MΦs were treated with LPS alone (1 μg/ml), ATP alone (ATPlow: 0.5 mM; ATPhi: 5 mM) or were primed with LPS for 3 hours and then treated with ATP. Supernatants were collected 18 hours after LPS administration and levels of secreted IL-1β were measured by ELISA. Means and standard deviations of two independent experiments are shown. FIGS. 51B-51C depict bar graphs showing secreted and cell-associated IL-1β levels for DCs primed or not primed with different doses of LPS (100 and 1000 ng/ml) and 3 hours later cells were activated with oxPAPC (120 μM) or ATP (0.5 mM). Supernatants were collected 18 hours after LPS administration and levels of secreted IL-1β (FIG. 51B) and cell associated IL-1β (FIG. 51C) were measured by ELISA. Means and standard deviations of biological duplicates from one experiment representative of three are shown. FIG. 51D depicts a bar graph showing TNFα results for DCs or MΦs treated with LPS alone (1 g/ml), ATP alone (0.5 mM), oxPAPC alone (120 μM) or primed with LPS for 3 hours and then treated with ATP or oxPAPC. Supernatants were collected 18 hours after LPS administration and levels of TNFα were measured by ELISA. Means and standard deviations of two independent experiments are shown. FIG. 51E depicts a bar graph showing secreted and cell-associated IL-1β results for DCs treated with LPS alone (1 g/ml), ATP alone (0.5 mM), oxPAPC alone (120 μM) or co-administered with LPS and ATP or LPS and oxPAPC. Secreted and cell-associated IL-1β were measured by ELISA 18 hours later. Means and standard deviations of two independent experiments are shown. FIG. 51F depicts a bar graph showing IL-1β and TNFα secretion results for DCs treated with LPS alone (1 μg/ml), ATP alone (5 mM), the indicated phospholipids alone (120 μM) or primed with LPS for 3 hours and then treated with ATP or the indicated phospholipids. 18 hours after LPS administration, IL-1β and TNFα secretion was measured by ELISA. Means and standard deviations of two independent experiments are shown. FIG. 51G depicts bar graphs showing IL-1β and TNFα secretion results for DCs and MΦs (pre-treated or not with IFNγ) treated with LPS alone (1 μg/ml), ATP alone (1 mM for DCs and 5 mM for MΦs), oxPAPC alone (120 μM) or pretreated with LPS for three hours and then activated with ATP or oxPAPC. Secreted IL-1β and TNFα were measured by ELISA 18 hours later. Means and standard deviations of two replicates of one representative experiment of two are shown. FIG. 51H depicts a blot showing that DCs and MΦs expressed different levels of ASC protein. DCs and MΦs were treated or not with LPS for 4 hours. Total lysates were used to assess the protein abundance of ASC by Western analysis. FIG. 51I depicts bar graphs showing gene expression results for DCs and MΦs treated or not treated with LPS for 4 hours. ASC, Nlrp3, caspase-1 (Casp-1) and caspase-11 (Casp-11) expression was measured by qPCR. Gene expression levels relative to TBP are shown. Line graphs represent the average of triplicate readings from one representative experiment of three.

FIGS. 52A-52I depict images showing that oxPAPC bound to caspsase-11 and regulated inflammasome activation in DCs (see also FIGS. 46A-46G). FIG. 52A depicts a line graph showing ASC and caspase-1 containing speck formation for DCs primed with LPS (1p g/ml) and then activated with ATP (1 mM) or oxPAPC (120 μM). At the indicated times, ASC and caspase-1 containing speck formation was assessed. Data represent means and standard deviations of three fields containing around 50 cells obtained in three independent experiments. FIG. 52B depicts a bar graph showing ASC and caspase-1 containing speck formation for DCs primed with LPS (1 μg/ml) and then activated with ATP (1 mM) or oxPAPC (120 μM). 18 hours later ASC and caspase-1 containing speck formation was assessed. Data represent means and standard deviations of three independent experiments. FIG. 52C depicts bar graphs showing IL-1β and TNFα secretion for DCs of the indicated genotype treated with Pam3CSK (P3C) alone (1 μg/ml), ATP alone (0.5 mM), oxPAPC alone (120 μM) or primed with Pam3CSK for 3 hours and then treated with ATP or oxPAPC. 18 hours after Pam3CSK administration, IL-1β and TNFα secretion was measured by ELISA. Means and standard deviations of two independent experiments are shown. FIG. 52D depicts a bar graph showing IL-1β and TNFα secretion for DCs treated with CpG alone (1p M), oxPAPC alone (120 µM) or primed with CpG for 3 hours and then treated with oxPAPC. 18 hours after CpG administration, IL-1β and TNFα secretion was measured by ELISA. Means and standard deviations of two independent experiments are shown. FIG. 52E depicts bar graphs showing secreted and cell-associated IL-1β levels for DCs derived from C3H/HeSNJ (WT C3H) and C3H/HeJ (TLR4 mutant C3H) mice treated with Pam3CSK (P3C) alone (1 µg/ml), oxPAPC alone (120 µM) or primed with Pam3CSK for 3 hours and then treated with oxPAPC. 18 hours after LPS administration, secreted (left panel) and cell associated (right panel) IL-1β were measured by ELISA. Means and standard deviations of biological duplicates from one experiment representative of two are shown. FIG. 52F depicts a line graph showing amounts of infectious virus in the eye for WT C57BL/6 (WT) or caspase-11 KO mice infected with HSV-1 in the eye. At the indicated times, the amount of infectious virus in the eye was measured by plaque assay. FIG. 52G depicts blots showing Caspase-11 levels in lysates from 293T cells expressing indicated caspase-11 alleles incubated with biotinylated ligands and streptavidin beads. Caspase-11 retained by the biotinylated ligands and inputs were detected by western analysis. Shown is a representative blot out of three independent experiments. Alleles of caspase-11 used were as follows: caspase-11 (WT), the CARD domain (1-92 a.a.) and the delta CARD (ΔCARD) domain (93-373 a.a.). FIGS. 52H-52I depict graphs showing enzymatic activity for recombinant caspase-11 monomers or oligomers mixed with the lipids indicated. Enzymatic activity was monitored over time by spectrofluorimetry.

FIGS. 53A-53D depict images showing that the inflammasome component expression was similar in WT DC and CD14KO DCs (Related to FIGS. 47A-47E). FIG. 53A depicts a bar graph showing IL-18 levels in WT DCs, CD14KO DCs and caspase-11 KO DCs treated with LPS alone (1 µg/ml), oxPAPC alone (120 µM), ATP alone (1 mM) or primed with LPS for 3 hours and then treated with oxPAPC or ATP. IL-18 was measured by ELISA in the supernatant 18 hours later. FIG. 53B depicts flow cytometry data showing MHC class II and CD40 levels for splenic DCs treated with LPS alone (1 g/ml), oxPAPC alone (120 µM), or primed with LPS for 3 hours and then treated with oxPAPC. 18 hours later, MHC class II and CD40 levels were measured by flow cytometry. FIG. 53C depicts bar graphs showing gene expression results for WT DC and CD14 KO DC treated with LPS or Pam3CSK (1p g/ml). Gene expression relative to TBP was analyzed by qPCR at times indicated. Untreated cells were used as a negative control in all experiments. FIG. 53D depicts bar graphs showing Secreted and cell-associated IL-1β for DCs pre-treated or not for 30 min with chloroquine (10 µM) and then stimulated with LPS alone (1 µg/ml), oxPAPC alone (120 µM) or primed with LPS and then treated with oxPAPC. Secreted and cell-associated IL-1β were measured by ELISA 18 hours later.

FIGS. 54A-54C depict images showing that oxPAPC did not induce pyroptosis in DCs and promoted enhanced T-cell activation (see also FIGS. 48A-48G). FIG. 54A depicts a line graph showing pyroptotic cell levels for WT DCs treated with LPS alone (1 µg/ml), or primed with LPS for 3 hours and then treated with oxPAPC (120 µM) or ATP (5 mM). Pyroptosis induction was assessed up to 18 hours after stimuli addition. Pyroptotic cells were identified as Annexin V and 7-AAD double positive cells by flow cytometry. Data are representative of two independent experiments. FIG. 54B depicts a bar graph showing IL-2 secretion for CD4+ T-cells isolated from the draining lymph nodes 40 days after immunization with OVA+LPS in IFA (LPS), OVA+LPS+ oxPAPC in IFA (LPS+oxPAPC) or OVA+oxPAPC in IFA (oxPAPC) of WT, caspase-1/-11 dKO or caspase-11 KO mice. CD4+ T-cells were restimulated or not with OVA in the presence of DC as antigen presenting cells. IL-2 secretion was measured 5 days later by ELISA. Bar graphs represent means and standard errors of two experiments with five animals per group. FIG. 54C depicts bar graphs showing that oxPAPC potentiated effector T cell responses in vivo. CD4+ T-cells were isolated from the draining lymph nodes 7 days after immunization with OVA+LPS in IFA (LPS), OVA+LPS+oxPAPC in IFA (LPS+oxPAPC) or OVA+ox-PAPC in IFA (oxPAPC) of WT, caspase-1/-11 dKO or caspase-11 KO mice. CD4+ T-cells were restimulated or not with OVA in the presence of DC as antigen presenting cells. IFNγ (upper panel) and IL-17 (lower panel) secretion was measured 5 days later by ELISA. Bar graphs represent means and standard errors of four experiments with three mice per group.

DETAILED DESCRIPTION

Figure 1:
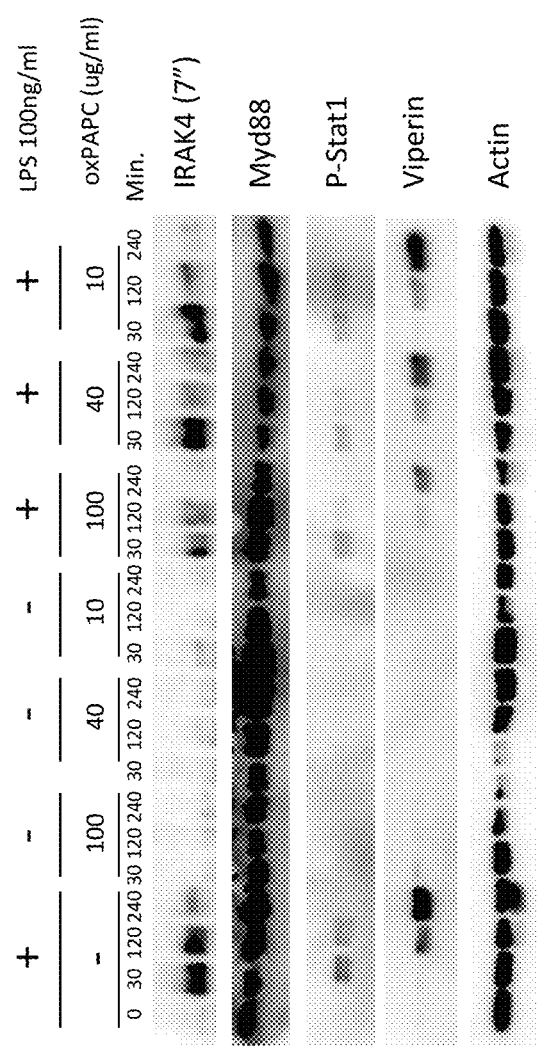
FIG. 1 shows that PAPCs (e.g., oxPAPC) were identified to act as TLR4-antagonists and not as TLR4-agonists.

The present invention relates, at least in part, to the unexpected observation that a PAPC lipid, particularly oxidized PAPC lipids (oxPAPCs), functions as a specific activator of inflammatory responses in dendritic cells (DCs). Specifically, 1-palmitoyl-2-arachidonyl-sn-glycero-3-phosphorylcholine (PAPC) and its oxidized variant (oxPAPC) were identified as the first specific activators of inflammatory responses in dendritic cells (DCs). In the presence of TLR ligands, oxPAPC promoted DC survival and triggered the release of the T-cell activating cytokine, interleukin 1 beta (IL-1β).

Without wishing to be bound by theory, mechanistically, oxPAPC is believed to have engaged the LPS receptor CD14 on the surface of DCs, which promoted its delivery into endosomes and subsequent access to the cytosolic protein caspase-11. Caspase-11 engagement by oxPAPC triggered the inflammasome-mediated release of IL-1β. Remarkably, these oxPAPC triggered responses did not occur in macrophages, indicating that the actions of this lipid were uniquely designed to promote immuno-regulatory activities of DCs, as opposed to general (macrophage-mediated) inflammatory responses. Consequently, oxPAPC synergized with microbial products to induce a more robust activation of antigen specific T-cells than could be elicited by PAMPs alone. oxPAPC was therefore identified as a member of a new class of immuno-modulatory factors (termed "vita-DAMPs"), which function together with PAMPs to promote DC survival and elicit maximal adaptive immune responses.

DCs are the most potent activators of protective (adaptive) immunity, and much current work is focused on designing vaccine adjuvants that selectively promote DC-mediated immunity. All currently FDA-approved vaccine adjuvants are unable to specifically activate DCs. They all promote general inflammatory responses in a variety of immune cells, including macrophages, DCs and others.

The current discovery that PAPCs can specifically activate functions in DCs has identified this molecule as a lead candidate for a next-generation vaccine adjuvant. Of note, PAPCs have been studied in the past by other research groups, but most research in this area has focused on their ability to act as anti-inflammatory molecules. The current discovery that PAPCs act to promote immunity, rather than inhibit immunity, distinguishes the currently described and exemplified uses of PAPCs from previous suggestions regarding the therapeutic value of these molecules.

A key finding in identifying the current invention was the discovery that PAPCs were only capable of promoting DC-mediated immune responses if co-administered with microbial products. This co-administration created a state of the DCs that had not been observed before, and it is foreseen that this novel cellular behavior is of prime therapeutic potential.

Definitions

The term "oxPAPC" or "oxidized PAPC", as used herein, refers to lipids generated by the oxidation of 1-palmitoyl-2-arachidonyl-sn-glycero-3-phosphorylcholine (PAPC), which results in a mixture of oxidized phospholipids containing either fragmented or full length oxygenated sn-2 residues. Well-characterized oxidatively fragmented species contain a five-carbon sn-2 residue bearing omega-aldehyde or omega-carboxyl groups. Oxidation of arachidonic acid residue also produces phospholipids containing esterified isoprostanes. oxPAPC includes HOdiA-PC, KOdiA-PC, HOOA-PC and KOOA-PC species, among other oxidized products present in oxPAPC.

The term "non-canonical inflammasome-activating lipid", as used herein, refers to a lipid capable of eliciting an inflammatory response in a caspase 11-dependent inflammasome of a cell. Exemplary "non-canonical inflammasome-activating lipids" include PAPC, oxPAPC and species of oxPAPC (e.g., HOdiA-PC, KOdiA-PC, HOOA-PC, KOOA-PC), as well as Rhodo LPS (LPS-RS or LPS from *Rhodobacter sphaeroides*).

"Immunogen" and "antigen" are used interchangeably and mean any compound to which a cellular or humoral immune response is to be directed against. Non-living immunogens include, e.g., killed immunogens, subunit vaccines, recombinant proteins or peptides or the like. The adjuvants of the invention can be used with any suitable immunogen. Exemplary immunogens of interest include those constituting or derived from a virus, a *mycoplasma*, a parasite, a protozoan, a prion or the like. Accordingly, an immunogen of interest can be from, without limitation, a human papilloma virus, a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, and/or *Trypanosoma cruzi*. It is further contemplated that adjuvant lipids of the invention can be co-administered with tumor or other cancer antigens, thereby providing an immunostimulatory cancer therapy/cancer vaccine.

"Concurrently administered" as used herein means that two compounds are administered sufficiently close in time to achieve a combined immunological effect. Concurrent administration may thus be carried out by sequential administration or simultaneous administration (e.g., simultaneous administration in a common, or the same, carrier).

The "modulation" of, e.g., a symptom, level or biological activity of a molecule, or the like, refers, for example, to the symptom or activity, or the like that is detectably increased or decreased. Such increase or decrease may be observed in treated subjects as compared to subjects not treated with an adjuvant lipid of the invention (a non-canonical inflammasome-activating lipid), where the untreated subjects (e.g., subjects administered immunogen in the absence of adjuvant lipid) have, or are subject to developing, the same or similar disease or infection as treated subjects. Such increases or decreases may be at least about 2%, 55%, 10%, 15%, 20%, 25%, 30%, 40%, 50%, 60%, 70%, 75%, 80%, 85%, 90%, 95%, 98%, 100%, 150%, 200%, 250%, 300%, 400%, 500%, 1000% or more or within any range between any two of these values. Modulation may be determined subjectively or objectively, e.g., by the subject's self-assessment, by a clinician's assessment or by conducting an appropriate assay or measurement, including, e.g., assessment of the extent and/or quality of immunostimulation in a subject achieved by an administered immunogen in the presence of an adjuvant lipid of the invention (a non-canonical inflammasome-activating lipid). Modulation may be transient, prolonged or permanent or it may be variable at relevant times during or after an adjuvant lipid of the invention is administered to a subject or is used in an assay or other method described herein or a cited reference, e.g., within times described infra, or about 12 hours to 24 or 48 hours after the administration or use of an adjuvant lipid of the invention to about 3, 4, 5, 6, 7, 8, 9, 10, 11, 12, 13, 14, 21, 28 days, or 1, 3, 6, 9 months or more after a subject(s) has received such an immunostimulatory composition/treatment.

As used herein, "subject" includes animals that possess an adaptive immune system, as described herein, such as human (e.g., human subjects) and non-human animals. The term "non-human animals" includes all vertebrates, e.g., mammals, e.g., rodents, e.g., mice, and non-mammals, such as non-human primates, e.g., sheep, dog, cow, chickens, amphibians, reptiles, etc.

A "suitable dosage level" refers to a dosage level that provides a therapeutically reasonable balance between pharmacological effectiveness and deleterious effects (e.g., sufficiently immunostimulatory activity imparted by an administered immunogen in the presence of an adjuvant lipid of the invention, with sufficiently low macrophage stimulation levels). For example, this dosage level can be related to the peak or average serum levels in a subject of, e.g., an anti-immunogen antibody produced following administration of an immunogenic composition (comprising an adjuvant lipid of the invention) at the particular dosage level.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Any compositions or methods provided herein can be combined with one or more of any of the other compositions and methods provided herein.

Regulation of Dendritic Cells (DCs) and Pattern Recognition Receptors (PRRs)

The innate immune system has classically been viewed to operate in an all-or-none fashion, with DCs operating either to mount inflammatory responses that promote adaptive immunity, or not. TLRs expressed by DCs are therefore believed to be of central importance in determining immunogenic potential of these cells. The mammalian immune system is responsible for detecting microorganisms and activating protective responses that restrict infection. Central to this task are the dendritic cells, which sense microbes and subsequently promote T-cell activation. It has been suggested that dendritic cells can gauge the threat of any infection and instruct a proportional response (Blander, J. M. (2014). Nat Rev Immunol 14, 601-618; Vance, R. E. et al., (2009) Cell host & microbe 6, 10-21), but the mechanisms by which these immuno-regulatory activities could occur are unclear.

PRRs act to either directly or indirectly detect molecules that are common to broad classes of microbes. These molecules are classically referred to as pathogen associated molecular patterns (PAMPs), and include factors such as bacterial lipopolysaccharides (LPS), bacterial flagellin or viral double stranded RNA, among others.

An important attribute of PRRs as regulators of immunity is their ability to recognize specific microbial products. As such, PRR-mediated signaling events should provide a definitive indication of infection. It was postulated that a "GO" signal is activated by PRRs expressed on DCs that promote inflammation and T-cell mediated immunity. Interestingly, several groups have recently proposed that DCs may not simply operate in this all-or-none fashion (Blander, J. M., and Sander, L. E. (2012). Nat Rev Immunol 12,215-225; Vance, R. E. et al., (2009) Cell host & microbe 6, 10-21). Rather, DCs may have the ability to gauge the threat (or virulence) that any possible infection poses and mount a proportional response. The most commonly discussed means by which virulence can be gauged is based on the ability of virulent pathogens to activate a greater diversity of PRRs than non-pathogens. However, not all microbes have a common set of PRR activators, and not all PRR activators are of comparable potency. The number of PRRs activated during an infection may therefore not be an ideal gauge of virulence. Moreover, increasing the number of PRRs activated during an infection will lead to a greater inflammatory response in general, which may indirectly promote greater T-cell responses. Conditions previously suggested to heighten the state of DC activation (e.g. through the use of virulent pathogens as stimuli) are also expected to heighten the state of MΦ activation (Vance, R. E. et al., (2009) Cell host & microbe 6, 10-21). Thus, it remains unclear if mechanisms are truly in place for the immune system (i.e. DCs) to gauge the threat of an infection specifically.

One possible means by which the threat of infection could be assessed would be through the well-recognized process of coincidence detection, where independent inputs result in a response that differs from the one elicited by any single input. In the context of PRRs, one such input must be a microbial product as an indicator of infection, regardless of the threat of virulence. In order to gauge the virulence threat, a second input must exist. Without wishing to be bound by theory, it is now thought that this putative second input is a molecule produced at the site of tissue injury, as cellular damage is often a feature associated with highly pathogenic microbes. Candidate molecules that may provide a second stimulus to DCs are the diverse family of molecules called danger associated molecules patterns (DAMPs), which are also known as alarmins (Kono, H., and Rock, K. L. (2008) Nat Rev Immunol 8,279-289; Pradeu, T., and Cooper, E. L. (2012) Front Immunol 3, 287). DAMPs have been found at sites of infectious and non-infectious tissue injury, and have been proposed to modulate inflammatory responses, although their mechanisms of action remain unclear. One such class of DAMPs is represented by oxidized phospholipids derived from 1-palmitoyl-2-arachidonyl-sn-glycero-3-phosphorylcholine (PAPC), which are collectively known as oxPAPC. These lipids are produced at the sites of both infectious and non-infectious tissue injury (Berliner, J. A., and Watson, A. D. (2005). N Engl J Med 353, 9-11; Imai, Y. et al. (2008) Cell 133, 235-249; Shirey, K. A. et al. (2013) Nature 497, 498-502) and are found at very high levels in the membranes of dying cells (Chang, M. K. et al., (2004) J Exp Med 200, 1359-1370). oxPAPC is also an active component of oxidized low density lipoprotein (oxLDL) aggregates that promote inflammation in atherosclerotic tissues (Leitinger, N. (2003) Curr Opin Lipidol 14, 421-430), where local concentrations can be as high as 10-100 μM (Oskolkova, O. V. et al. (2010) J Immunol 185, 7706-7712). The association between oxPAPC and dying cells raised the possibility that these lipids could serve as a generic indicator of tissue health. In the presence of microbial product(s), oxPAPC may therefore indicate an increased infectious threat.

Without wishing to be bound by theory, mechanistically, the receptor CD14 appears to capture lipids such as oxPAPC and PAPC and deliver them to an intracellular location where they activate non-canonical inflammasomes (Caspase 11-dependent inflammasomes). Inflammasome-mediated activities then synergize with independently occurring TLR signaling events to promote more robust T-cell responses than those induced by TLR ligands alone. Thus, oxidized lipids appear to alert dendritic cells to a highly infectious microbial encounter, allowing these cells to promote an adaptive response that is commensurate with the infectious threat.

Toll-Like Receptors

Toll-like receptors (TLRs) are type I transmembrane receptors, evolutionarily conserved between insects and humans. Ten TLRs have so far been established (TLRs 1-10) (Sabroe, I. et al., (2003) Journal of Immunology 171(4): 1630-5). Members of the TLR family have similar extracellular and intracellular domains; their extracellular domains have been shown to have leucine—rich repeating sequences, and their intracellular domains are similar to the intracellular region of the interleukin-1 receptor (IL-1β R). TLR cells are expressed differentially among immune cells and other cells (including vascular epithelial cells, adipocytes, cardiac myocytes and intestinal epithelial cells). The intracellular domain of the TLRs can interact with the adaptor protein Myd88, which also posses the IL-1β R domain in its cytoplasmic region, leading to NF-KB activation of cytokines; this Myd88 pathway is one way by which cytokine release is effected by TLR activation. The main expression of TLRs is in cell types such as antigen presenting cells (e.g. dendritic cells, macrophages etc.). One such TLR is TLR4, which is responsible for activating the innate immune system and recognizes lipopolysaccharide (LPS), a component of gram-negative bacteria. TLR4 has been shown to interact with lymphocyte antigen 96, Myd88 (myeloid differentiation primary response gene 88), and TOLLIP (toll interacting protein).

Activation of dendritic cells by stimulation through the TLRs leads to maturation of dendritic cells, and production of inflammatory cytokines such as IL-12. Research carried out so far has found that TLRs recognize different types of agonists, although some agonists are common to several TLRs. TLR agonists are predominantly derived from bacteria or viruses, and include molecules such as flagellin or bacterial lipopolysaccharide (LPS).

Two States of DC Activation

Two states of DC activation were identified herein. The first activation state was mediated by encounters with microbial products, such as TLR ligands. These ligands activated TLRs to release cytokines, upregulate co-stimulatory molecules and promote MHC-mediated antigen presentation, all of which were important for T-cell activation. However, these TLR ligands were common to pathogens and non-pathogens and cannot be used to gauge threat to the host. The second state of DCs was considered "hyperactive", and was mediated by coincident encounters with microbial products and oxidized phospholipids that were abundant at sites of tissue damage. The coincident detection of TLR ligands and oxidized lipids (e.g. oxPAPC) promoted all the activities elicited by the classical activation state, and induced the inflammasome-mediated release of IL-1β, a potent activator of T-cells. Neither TLR ligands alone nor oxPAPC alone possessed the ability to induce IL-1β release, an observation that provided formal experimental evidence that the innate immune system employed the principle of coincidence detection to induce a hyperactive state in DCs.

An intriguing aspect of the hyperactive DC state was the mechanism by which it was elicited. Whereas the classical activation was elicited by microbial products, the hyperactive state was elicited by microbial products and self-derived products. This self-referential aspect of immune activation was not without precedent, as T-cell maturation and maintenance had been previously shown to rely upon interactions with MHC molecules bearing microbial and self-peptides (Janeway, C. A., Jr. (2002) Annu Rev Immunol 20, 1-28). Mechanistically, the analysis of oxPAPC revealed this molecule to be a selective endogenous mimic of LPS, in that it bound and activated the LPS receptors CD14 and caspase-11. Interestingly, oxPAPC did not induce TLR4 dimerization, endocytosis, myddosome formation or gene expression. In fact, when administered prior to microbial encounters, oxPAPC acted as a TLR4 antagonist (Bochkov, V. N. et al., (2002) Nature 419, 77-81; Erridge, C. et al., (2008) The Journal of biological chemistry 283, 24748-24759; Oskolkova, O. V. et al. (2010) J Immunol 185, 7706-7712). The collective data therefore revealed an intriguing cellular process by which CD14 functions to coordinate the activities of TLR4 and caspase-11, by delivering either PAMPs (LPS) or DAMPs (oxPAPC) to their respective receptors.

Several observations supported the central aspect of this proposed CD14-caspase-11 pathway to DC hyperactivation. First, oxPAPC formed a complex with CD14 and caspase-11 in vitro. Second, genetic deficiencies of CD14 and caspase-11 phenocopied one another, in that the loss of either protein resulted in an inability of DCs to release IL-1β in response to oxPAPC treatment. In contrast, neither CD14 nor caspase-11 was required for ATP-mediated IL-1β release. Third, neither of these proteins was required during the priming phase of inflammasome activation, as assessed by the normal level of expression of various TLR-dependent cytokines. Fourth, binding of oxPAPC to CD14 promoted endocytosis and the delivery of this lipid to intracellular caspase-11. Support for this statement derived from the ability of transfection of oxPAPC into the cytosol to rescue defects in IL-1β release in CD14 KOs. This observation provided definitive evidence that the transport function of CD14 was critical for caspase-11 activation.

Caspase-11 has attracted much attention in recent years, based on its ability to promote IL-1β release and pyroptosis in response to gram-negative cytosolic bacteria (Hagar, J. A. et al., (2013) Science 341, 12501253; Kayagaki, N. et al. (2013) Science 341, 1246-1249). This selectivity of caspase-11 in promoting immune responses to gram-negative bacteria was explained by its newly recognized ability to operate as a bonafide LPS receptor (Shi, J. et al., (2014a) Nature 514, 187-192). oxPAPC bound to caspase-11 and extended the role of caspase-11 beyond its operation as an LPS receptor. Indeed, caspase-11 was required for oxPAPC-mediated IL-1β release when TLR4 ligands were not present, such as when cells were primed with ligands often associated with gram-positive bacteria (i.e. Pam3CSK) or viruses (CpG DNA).

Based on these data, caspase-11 had a general function as a gauge of virulence threat in DCs. The threat was assessed in two ways. First, by virtue of its ability to bind oxPAPC, a self-derived indicator of damage, caspase-11 may become activated during encounters with any pathogen that causes tissue damage and cell death. This activity would therefore provide DCs with a general mechanism to become hyper-activated during infections with virulent microorganisms. Secondly, in the case of bacteria that encode Type III and Type IV secretion systems, which deliver LPS to the cytosol directly (Hagar, J. A., and Miao, E. A. (2014) Curr Opin Microbiol 17, 61-66), caspase-11 likely hyperactivated DCs even before tissue damage occurred. Under these latter conditions, the delivery of LPS to the cytosol by virulence-associated secretion systems should not have involved the transport functions of CD14. Indeed, it was identified herein that the genetic requirement of CD14 for inflammasome activation could be bypassed by transfection of LPS or oxPAPC directly into the cytosol. Natural delivery of oxPAPC from the extracellular media to caspase-11, in contrast, was dependent upon CD14. This critical role of CD14 in mediating caspase-11 activation suggested that this protein possessed a broader function in inducing adaptive immunity than would be predicted by its assignment as an LPS receptor. Rather, CD14 and caspase-11 are general regulators of immunity against a wide range of pathogens. In vivo support for this model came from the finding that HSV-1 replication in the eye was restricted by the actions of caspase-11.

The mechanistic studies also revealed that oxPAPC differed from LPS in its actions towards caspase-11 in several fundamental ways. First, whereas both lipids bound to caspase-11 and induced its oligomerization, LPS bound the CARD, whereas oxPAPC bound the catalytic domain. These differential mechanisms of engagement had functional consequences, as binding to the CARD promoted the caspase-11 enzymatic activity, whereas binding the catalytic domain prevented enzymatic activity. Since the enzymatic activity of caspase-11 was necessary for pyroptosis, it stood to reason that oxPAPC should not kill cells. Indeed, through population-based and single cell analyses, oxPAPC was identified as not killing cells, and it was identified that inflammasomes were present within living DCs that have been exposed to oxPAPC. In contrast, in DCs that were exposed to ATP, inflammasomes were present only within dead cells. In fact, oxPAPC promoted the viability of DCs that were also exposed to LPS. Whereas there were several examples of endogenous molecules that bind to PRRs, most current information suggested the modes of interactions were similar to those that mediate microbial interactions (or are unknown). Caspase-11 therefore represented an unusual PRR in that it contained distinct domains that interact with PAMPs (LPS) and endogenous molecules (oxPAPC). These distinct modes of interaction resulted in different cellular responses, which indicated that like DCs, PRRs also possessed different states of activation.

The dual activities of oxPAPC to promote inflammasome activation and DC survival indicated a role for these activities in the potentiation of adaptive immune responses. Indeed, LPS/oxPAPC was identified herein as a superior adjuvant than LPS alone, in terms of eliciting antigen-specific effector and memory T-cells in vivo. Other instances of inflammasome activation occurring independent of cell death have also been observed (Broz, P. et al., (2010) Cell Host Microbe 8, 471-483; Ceballos-Olvera, I. et al., (2011) PLoS Pathog 7, e1002452; Schmidt, R. L., and Lenz, L. L. (2012) PLoS One 7, e45186). Ongoing studies are exploring the mechanisms by which death and IL-1β release are coordinated. Based on its unusual ability to be both a pro-inflammasome and pro-survival stimulus, it is herein concluded that oxPAPC can be considered a vita-DAMP, that functions to promote DC survival and the initiation of adaptive immunity. vita-DAMPs can be operationally distinguished from traditionally-defined DAMPs, such as ATP, because they promote cell viability, as opposed to promoting pyroptotic cell death. It is also contemplated herein that other known TLR4 antagonists can be selective LPS mimics that possess similar activities as oxPAPC. It was also noted that oxPAPC was released under non-infectious circumstances. Under these conditions, the ability of oxPAPC to promote CD14 endocytosis likely helped limit TLR4-dependent inflammatory responses that could mistakenly have been activated by other DAMPs present at the sites of injury (Mancek-Keber, M., et al. (2015) Science signaling 8, ra60). This context-dependent activity of oxPAPC as either inhibiting or promoting inflammation is identified as critical in helping DCs gauge the source of damage in a given tissue.

In summary, a means by which an endogenous self-molecule can create a hyperactive state of DCs through the ability to engage caspase-11 in an atypical manner was identified herein. The existence of this hyperactive state revealed that the innate immune system operated through a mechanism by which infectious threat was assessed by the coincident detection of PAMPs and vita-DAMPS.

Adjuvants and Vaccines

Immunogenic compositions comprising adjuvants of the invention may be administered to a subject using any known form of vaccine, e.g., attenuated virus, protein, nucleic acid, etc. vaccine, so as to produce in the subject, an amount of the selected immunogen which is effective in inducing a therapeutic or prophylactic immune response against the target antigen in the subject. The subject may be a human or nonhuman subject. Animal subjects include, without limitation, non-human primates, dogs, cats, equines (horses), ruminants (e.g., sheep, goats, cattle, camels, alpacas, llamas, deer), pigs, birds (e.g., chicken, turkey quail), rodents, and chirodoptera. Subjects can be treated for any purpose, including without limitation, eliciting a protective immune response, or producing antibodies (or B cells) for collection and use for other purposes.

In certain embodiments, the invention features an adjuvant-containing microbial vaccine. Microbial vaccines are often comprised of the cell wall components that allow the immune system to recognize the whole organism, or in bacteria that cause disease through toxicity—such as Diphtheria, the toxin or derived toxoid may be used. Antitoxins are being developed for some disease organisms, predominantly for therapeutic use. Bacteria may be cultured in liquid media, or as solid substrate cultures, harvested, purified and used directly as killed or attenuated vaccines.

Optionally, an immunogen of interest is expressed by diseased target cells (e.g., neoplastic cell, infected cells), and expressed in lower amounts or not at all in other tissue. Examples of target cells include cells from a neoplastic disease, including but not limited to sarcoma, lymphoma, leukemia, a carcinoma, melanoma, carcinoma of the breast, carcinoma of the prostate, ovarian carcinoma, carcinoma of the cervix, colon carcinoma, carcinoma of the lung, glioblastoma, and astrocytoma. Alternatively, the target cell can be infected by, for example, a virus, a *mycoplasma*, a parasite, a protozoan, a prion and the like. Accordingly, an immunogen of interest can be from, without limitation, a human papilloma virus (see below), a herpes virus such as herpes simplex or herpes zoster, a retrovirus such as human immunodeficiency virus 1 or 2, a hepatitis virus, an influenza virus, a rhinovirus, respiratory syncytial virus, cytomegalovirus, adenovirus, *Mycoplasma pneumoniae*, a bacterium of the genus *Salmonella, Staphylococcus, Streptococcus, Enterococcus, Clostridium, Escherichia, Klebsiella, Vibrio, Mycobacterium*, amoeba, a malarial parasite, and *Trypanosoma cruzi*.

In addition to tumor antigens and antigens of infectious agents, mutants of tumor suppressor gene products including, but not limited to, p53, BRCA1, BRCA2, retinoblastoma, and TSG101, or oncogene products such as, without limitation, RAS, W T, MYC, ERK, and TRK, may also provide target antigens to be used according to the invention. The target antigen can be a self-antigen, for example one associated with a cancer or neoplastic disease. In an embodiment of the invention, the immunogen is a peptide from a heat shock protein (hsp)-peptide complex of a diseased cell, or the hsp-peptide complex itself.

In certain embodiments, the immunogen may be purified from a natural source, obtained by means of recombinant expression, or synthesized directly. In certain embodiments, the immunogen can be provided by whole cells, microorganisms, or viral particles, which may be live, attenuated, or killed. In other embodiments, the immunogen may comprise a protein fragment comprising one or more immunogenic regions of the molecule.

Immunogens include those that are modified or derivatized, such as by conjugation or coupling to one or more groups to enhance an immune response of the subject. Examples of immunogenic carrier proteins are KLH and BSA. Immunogenic carriers also include polypeptides that are promiscuous Class II activators (see, e.g., Panina-Bordignon et al, Cold Spring Harb Symp Quant Biol 1989). Conjugate linkages are made by methods well known to those of skill in the art.

Immunogenic compositions of the invention comprise an immunogen and an adjuvant lipid, and can be administered for therapeutic and/or prophylactic purposes. In therapeutic applications, an immunogenic composition of the invention is administered in an amount sufficient to elicit an effective immune response to treat a disease or arrest progression and/or symptoms. The dosage of the adjuvants of the invention will vary depending on the nature of the immunogen and the condition of the subject, but should be sufficient to enhance the efficacy of the immunogen in evoking an immunogenic response. For therapeutic or prophylactic treatment, the amount of adjuvant administered may range from 0.05, 0.1, 0.5, or 1 mg per kg body weight, up to about 10, 50, or 100 mg per kg body weight or more. The adjuvants of the invention are generally non-toxic, and generally can be administered in relatively large amount without causing life-threatening side effects.

The term "therapeutic immune response", as used herein, refers to an increase in humoral and/or cellular immunity, as measured by standard techniques, which is directed toward the target antigen. Preferably, the induced level of immunity directed toward the target antigen is at least four times, and preferably at least 16 times the level prior to the administration of the immunogen. The immune response may also be measured qualitatively, wherein by means of a suitable in vitro or in vivo assay, an arrest in progression or a remission of a neoplastic or infectious disease in the subject is considered to indicate the induction of a therapeutic immune response.

In the methods of the present invention, a composition comprising an immunogen and an adjuvant of the invention, combined in therapeutically effective amounts, is administered to a mammal in need thereof. The term "administering" as used herein means delivering the immunogen and adjuvant of the present invention to a mammal by any method that may achieve the result sought. They may be administered, for example, intravenously or intramuscularly. The term "mammal" as used herein is intended to include, but is not limited to, humans, laboratory animals, domestic pets and farm animals. "Therapeutically effective amount" means an amount of the immunogen and adjuvant that, when administered to a mammal, is effective in producing the desired therapeutic effect.

Compositions comprising immunogens and adjuvants of the invention may be administered cutaneously, subcutaneously, intravenously, intramuscularly, parenterally, intrapulmonarily, intravaginally, intrarectally, nasally or topically. The composition may be delivered by injection, orally, by aerosol, or particle bombardment.

Compositions for administration may further include various additional materials, such as a pharmaceutically acceptable carrier. Suitable carriers include any of the standard pharmaceutically accepted carriers, such as phosphate buffered saline solution, water, emulsions such as an oil/water emulsion or a triglyceride emulsion, various types of wetting agents, tablets, coated tablets and capsules. Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients. The composition of the invention may also include suitable diluents, preservatives, solubilizers, emulsifiers, adjuvants and/or carriers. Such compositions may be in the form of liquid or lyophilized or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g. glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexing with metal ions, or incorporation of the material into or onto particulate preparations of polymeric compounds such as polylactic acid, polyglycolic acid, hydrogels, etc. or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance.

Pharmaceutical Compositions

In certain embodiments, the present invention provides for a pharmaceutical composition comprising an immunogen and an adjuvant lipid as identified herein. The immunostimulatory composition can be suitably formulated and introduced into a subject or the environment of a cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The compositions of the invention could also be formulated as nanoparticle formulations.

The compounds of the invention can be administered for immediate-, delayed-, modified-, sustained-, pulsed- or controlled-release applications.

The pharmaceutical compositions of the invention may contain from 0.01 to 99% weight-per volume of the active material.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For a compound used in a method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an adjuvant-containing composition of the invention targeting a disease or disorder (i.e., an effective dosage) depends on the immunogen and target disease or disorder selected. For instance, single dose amounts of an immunogen of an immunogen-adjuvant composition of the invention targeting a disease or disorder in the range of approximately 1 µg to 1000 mg may be administered; in some embodiments, 10, 30, 100, or 1000 µg, or 10, 30, 100, or 1000 ng, or 10, 30, 100, or 1000 µg, or 10, 30, 100, or 1000 mg may be administered. In some embodiments, 1-5 g of the compositions can be administered.

A therapeutically effective amount of the compound of the present invention can be determined by methods known in the art. In addition to depending on the immunogen used, the therapeutically effective quantities of a pharmaceutical composition of the invention will depend on the age and on the general physiological condition of the patient and the route of administration. In certain embodiments, the therapeutic doses will generally be between about 10 and 2000 mg/day and preferably between about 30 and 1500 mg/day. Other ranges may be used, including, for example, 50-500 mg/day, 50-300 mg/day and 100-200 mg/day.

Administration may be a single dose, multiple doses spaced at intervals to allow for an immunogenic response to occur, once a day, twice a day, or more often, and may be decreased during a maintenance phase of a disease or disorder, e.g. once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an immunogenic, adjuvant-containing composition targeting a disease, disorder or infectious agent can include a single treatment or, optionally, can include a series of treatments.

The pharmaceutical compositions can be included in a kit, container, pack, or dispenser together with instructions for administration.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. It is to be understood and expected that variations in the principles of invention herein disclosed may be made by one skilled in the art and it is intended that such modifications are to be included within the scope of the present invention.

INCORPORATION BY REFERENCE

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, either in a Reference List before the claims, or in the text itself; and, each of these documents or references ("herein-cited references"), as well as each document or reference cited in each of the herein-cited references (including any manufacturer's specifications, instructions, etc.), is hereby expressly incorporated herein by reference. In case of conflict, the present specification, including definitions, will control. In addition, the materials, methods, and examples are illustrative only and not intended to be limiting.

EXAMPLES

Example 1: Materials and Methods

Mouse Strains and Cell Culture

C57BL/6J (Jax 000664), C57BL/6NJ (Jax 005304), CD14 KO (Jax 003726), caspase-1/-11 dKO mice (Jax 016621), TLR4-mutant (C3H/HeJ, Jax 000659), and wild-type control for TLR4-mutant (C3H/HeSNJ, Jax 000661) were purchased from Jackson Labs. NLRP3 KO and ASC KO mice were kindly provided by Dr. T. Horng, Harvard School of Public Health. Caspase-11 KO mice were kindly provided by Dr. Junying Yuan, Harvard Medical School. Caspase-1 single KO mice were kindly provided by Thirumala-Devi Kanneganti (St. Judes). DCs were differentiated from bone marrow in IMDM (Gibco), 10% B16-GM-CSF derived supernatant, 2 µM 2-mercaptoethanol and 10% FBS and used after 6 day of culture. DC purity was assessed by flow cytometry and was usually higher than 90%. M were differentiated from bone marrow in DMEM (Gibco), 30% L929 supernatant, and 10% FBS. Immortal MΦs were cultured in DMEM supplemented with 10% L929 supernatant and 10% FBS. Splenic DCs were purified as described previously (Zanoni et al., 2012). Prior to stimulations, cultured cells were washed and re-plated in DMEM supplemented with 10% FBS at a concentration of 1×106 cells/ml in a final volume of 100 µl. For experiments using pan-caspase inhibitor, cells were treated with zVADfmk (20 µM) 30 min before inflammasome activation stimuli addition. Cycloheximide (50 ng/ml) was added at the time of stimuli administration. Transfection with DOTAP was performed following the manufacturer instructions. Briefly, 375 ng of DOTAP were added to 5 µg of LPS or 10 µg of oxPAPC in a final volume of 10 µl of DMEM without FBS. 30 min later, the DOTAP/LPS or DOTAP/oxPAPC complex were added to the culture. FuGENE was used as previously described (Kayagaki, N. et al. (2013) Science 341, 1246-1249) to transfect LPS and oxPAPC at the indicated concentrations.

Gene Expression Analysis and ELISA

RNA was isolated from cell cultures using Qiashedder (Qiagen) and GeneJET RNA Purification Kit (Life Technologies). Purified RNA was analyzed for gene expression on a CFX384 real time cycler (Bio-rad) using TaqMan RNA-to-CT 1-Step Kit (Applied Biosystems) with probes purchased from Life Technologies specific for viperin (Mm00491265_m1), IFNb1 (Mm00439552_s1), IL6 (Mm00446190_m1), caspase-1 (Mm00438023_m1), caspase-11 (Mm00432307_m1), Nlrp3 (Mm00840904_m1), Asc (Mm00445747_g1), TBP (Mm00446971_m1) or GAPDH (Mm99999915_g1). ELISA for IL-1β, IL-2, IL-17, IL-18, TNFα and IFNγ were performed using Mouse Ready-SET-Go ELISA kits (eBioscience). To measure secreted cytokines, supernatant were collected, clarified by centrifugation and stored at −20° C. Cell associated cytokines were measured as follows: 96-well plates were centrifuged and supernatant was discarded. 250 µl of PBS were added to each well. Cells were frozen and thawed two times at −80° C. and then stored at −20° C. for further analysis.

Antibodies and Reagents

*E. coli* LPS (Serotype 055:B5-TLRgrade™) was purchased from Enzo. OxPAPC and Pam3CSK4 were purchased from Invivogen. Oxidized PAPE-N-biotin (biotin-oxPAPC) and oxPAPC enriched in PEIPC were produced as previously described (Springstead, J. R. et al., (2012) J Lipid Res 53,1304-1315). KOdiA-PC and DMPC were from Cayman Chemical and Avanti Polar Lipids, respectively. The following antibodies were used: HA (Roche; 3F10), MyD88 (R&D; AF3109), Actin (Sigma; A 5441), ASC (Millipore, clone 2EI-7), caspase-11 (Biolegend, clone Cas11.17D9), caspase-3 (Santa Cruz, H-277), viperin (Biolegend), phospho-Stat-1 (Cell Signaling, clone 58D6). The IRAK4 antibody was a gift from Shizuo Akira (Osaka University). For flow cytometry based assays, the fluorophore-conjugated antibodies were used as the following: PE anti-TLR4 (Biolegend; clone Sa15-21), PE/Cy7 anti-TLR4/MD2 (Biolegend; clone MTS510), FITC anti-CD14 (eBioscience; clone Sa2-8), APC anti-CD14 (ebioscience; clone Sa-28). PE-anti-MHC class II and APC anti-CD40 antibodies were from eBioscience. Annexin V and 7-AAD viability stain solution was purchased from BioLegend. Incomplete Freund's Adjuvant (F5506) and cycloheximide (C1988) were purchased from Sigma. DOTAP was purchased from Roche. FuGENE 2000 was from Promega. Endotoxin-free OVA was purchased from Hyglos/Biovendor. Recombinant IFN0 was from R&D Systems. Pierce LDH Cytotoxicity Assay Kit was purchased from Life Technologies.

Protein Purification and In Vitro Protein-Lipid Interactions

For studies to measure the direct binding of oxPAPC to caspase-11, proteins and SPR analysis was performed as described (Shi, J., et al., (2014b) Nature). Briefly, the recombinant catalytic mutant caspase-11 full length (C254A) and caspase-11 ΔN59 (C254A) were purified from P3 baculovirus infected SF-21 insect cells that were cultured in Sf-900™ II SFM for 72 h at 28° C. Cells were lysed in lysis buffer containing 1% Triton X-100, 50 mM Tris-HCl (pH 7.6), 300 mM NaCl, 50 mM imidazole and 5 mM 2-mercaptoethanol. Ni-NTA beads (Qiagen) were used to purify His-tagged proteins from lysates. Proteins were released from the beads with elution buffer containing 50 mM Tris-HCl (pH 7.6), 250 mM imidazole and 300 mM NaCl. Imidazole was removed by dialysis. The proteins were further purified with HiTrap Q column and Superdex G200 column (GE Healthcare Life Sciences) to reach high homogeneity.

For surface plasmon resonance (SPR) analysis, BIAcore T100 SPR instrument (GE Healthcare) was used to measure the ligand binding kinetics. The assays were performed in a buffer containing 150 mM NaCl, 3 mM EDTA, 50 mM HEPES (pH 7.5) and 0.005% Tween-20 at 25° C. CM5 sensor chip was first activated with 1:1 mixed 0.1 M N-ethyl-N'-(3-diethylaminopropyl)-carbodiimide and 0.1 M N-hydroxysuccinimide solution at a flow rate of 10 μL/min for 7 min. Catalytic mutant caspase-11 full length (C254A) and caspase-11 ΔN59 (C254A) were diluted to a concentration of 20 μg/mL with 10 mM sodium acetate (pH 5.0) and immobilized to about 3100 response units and 3300 response units respectively. 10 mM sodium acetate diluted rabbit IgG protein (10 μg/ml) was immobilized to 3400 response units and treated as negative control. 1 M ethanolamine (pH 8.5) was flowed over the CM5 chip to block all the remaining protein binding sites for 7 min (flow rate 10 μL/min). The ligands were passed over the flow cell and adjacent control flow cell (activated and blocked as targeting flow cells, but no protein was immobilized) for 1 min at a flow rate of 30 μL/min. A dissociation process was performed for 2 min at a flow rate of 30 μL/min. The bound ligands were removed with 20 mM NaOH washed for 20 seconds. The KD values were calculated by fitting result curves (subtracted the control flow cell value) to a 1:1 Langmuir binding model with the BIAcore T100 evaluation software.

For caspase-11 oligomerization and enzymatic activity assays, full length mouse caspase 11 was cloned into pFastBac™HT A vector (Invitrogen) with a TEV cleavable N-terminal 6× His tag using EcoRI and XhoI restriction sites. The protein was expressed using the Bac-to-Bac baculovirus-insect cell system. After 48 h-infection, the Sf9 cells that expressed His-caspase11 protein were harvested by centrifugation at 2,000 rpm for 20 min. The cell pellets were resuspended in a lysis buffer containing 20 mM HEPES at pH 7.5, 150 mM NaCl, 5 mM tris(2-carboxyethyl)phosphine (TCEP), 20 mM imidazole and a protease inhibitor cocktail, and homogenized by ultrasonication. The cell lysate was clarified by ultracentrifugation at 42,000 rpm at 4° C. for 2 hours. The supernatant containing the target protein was incubated with Ni-NTA resin (Qiagen) that was pre-equilibrated with the lysis buffer for 1 hour at 4° C. After incubation, the resin-supernatant mixture was poured into a column and the resin was washed with the lysis buffer. The proteins were eluted by the lysis buffer supplemented with 500 mM imidazole, and further purified by size exclusion chromatography.

To measure the ability of oxPAPC to oligomerize caspase-11, monomer or oligomer fractions of His-caspase11 were incubated with oxPAPC for 2 hours on ice, and then analyzed with Superdex 200 (10/300).

To characterize the association between biotinylated oxPAPC and HA-tagged caspase-11 in cell lysates, 293T cells were transiently transfected with pcDNA vector expressing indicated caspase-11 alleles (WT, K19E and 3K (K62E K63E K64E)) with the C-terminal fusion of an HA epitope. 48 hours after transfection, cells were collected with cold PBS and lysed in 1 ml lysis buffer containing 50 mM Tris-HCl (pH 7.4), 150 mM NaCl, 10% Glycerol and 1% NP-40 supplemented with complete protease inhibitor (Roche). Cells were lysed on ice for 30 min and the whole cell extracts were collected into a new tube after spinning at 14000×g for 15 minutes in a table-top centrifuge in the cold room. For each of the whole cell lysate containing the indicated caspase 11 alleles, 100 μL was taken out and saved as input. The remaining 900 μl lysates were equally split into 3 tubes with 300 μL each tube. 1 μg of biotinylated LPS and 10 μg of the biotinylated oxPAPC were added to the first and the second tube, respectively. The third tube was left as a mock control (to monitor the extent of non-specific binding between indicated caspase-11 alleles to the streptavidin beads). The biotinylated ligands and lysates were mixed and incubated at 4° C. on a nutator for either 6 hours or overnight. To capture the ligand-caspase-11 complex, streptavidin beads (20 μL bed volume) were then added to all of the tubes (including the mock control that was never treated with any biotinylated ligands). This capturing step was allowed to proceed at 4° C. for another 2 to 3 hours. The beads were then washed with the lysis buffer for 3 times and finally 50 μL of SDS loading buffer was added. The protein complexes were further eluted by heating at 65° C. for 15 minutes. 25 μL of the eluted protein complexes were separated by SDS-PAGE and the proteins retained by biotinylated ligands were detected by western analysis.

Capture of Endogenous Caspases Through Protein-Lipid Interactions

S100 fractions from iMΦs were prepared as follows. Confluent iBMDMs cultured in complete DMEM medium were harvested with ice-cold PBS plus EDTA (0.4 mM). Cells were then washed once with homogenization buffer (HB) (20 mM HEPES/KOH, pH7.9, 250 mM sucrose, 0.5 mM EGTA) supplemented with complete protease inhibitor tablets (Roche). Cells were lysed mechanically by subjecting to 20 strokes of douncing in the Wheaton™ Dounce Dura-Grind™ Tissue Grinder. The extent of cell lysis was monitored by Trypan blue staining to ensure that more than 80% of the cells were lysed. The crude lysates were then spun at 800×g for 10 min at 4° C. to remove unbroken cells and nuclear components. The post-nucleus supernatant were collected and spun at 13,000×g for 10 min at 4° C. to remove large organelles and membranes. Finally, the cleared lysates were transferred to Beckman polycarbonate ultracentrifugation tubes (343778) and spun at 100,000×g for 1 hour at 4° C. to remove residual membrane components. The resultant S100 supernatant (containing soluble cytosolic proteins) were stored at −80° C. with a protein concentration at 2 mg/mL or used as a source of endogenous caspases to be captured by biotinylated lipids. 1 mg of 5100 supernatant was incubated with 15 μg of biotin-oxPAPC for 12-16 hours at 4° C. on a nutator. Streptavidin agarose resin (Pierre, P. et al., (1997) Nature 388, 787-792) was used to capture the endogenous protein complexes associated with Biotinylated oxPAPC (with 20 μL bed volume resin per reaction) for 1 to 2 hours at 4° C. on a nutator. The protein complexes captured by the resin were then washed for 4 times with detergent-containing washing buffer (50 mM Tris-HCl, pH 7.5, 150 mM NaCl, 10% Glycerol, 1% NP-40) and further eluted by incubated with 60 μL of SDS loading buffer at 65° C. for 20 min. One third of the eluate was separated by SDS-PAGE and endogenous caspases retained by biotin-oxPAPC were detected by Western blotting using designated antibodies.

Caspase-11 Activity Assay

5 μM His-Caspase-11 with or without lipid (LPS, oxPAPC and DMPC) were used for caspase activity assay in the reaction buffer containing 50 mM HEPES (pH 7.5); 10% (v/v) glycerol; 10 mM DTT; 1.0 mM EDTA; 0.2% (w/v) BSA in a Corning® 96 Well Half Area Black Flat Bottom Microplate. Reactions were started by adding substrate YEVD-AMC at a final concentration of 10 μM. Data were collected with the SpectraMax M5e Multi-Mode Microplate Reader (Molecular Devices) using excitation at 385 nm and emission at 460 nm with an auto-cutoff filter at 455 nm.

Flow Cytometry iMΦs, primary bone marrow derived MΦs and DCs or splenic DCs (0.5×10$^6$) of the indicated genotypes were treated with E. coli LPS, oxPAPC or chemical inhibitors for the indicated time points at 37° C. Cells were then washed with 1 mL cold PBS and stained for appropriate antibodies on ice for 20 to 30 minutes. 2% mouse serum or rat serum were used as the blocking reagent to reduce non-specific binding of the antibodies. The stained cells were then washed with 1 mL cold PBS and resuspended in 200 μL PBS. Staining of the surface receptors was analyzed with BD FACSCanto II. The mean fluorescence intensity (MFI) of CD14, TLR4 from unstimulated or stimulated cells was recorded. The percentage of surface receptor staining at indicated time points, which is the ratio of the MFI values measured from the stimulated cells to those measured from the unstimulated cells, was plotted to reflect the efficiency of receptor endocytosis. For measuring the extent of TLR4/MD-2 dimerization, the percentage of TLR4/MD2 dimer was calculated by 100%–the percentage of TLR4/MD-2 monomer. The percentage of the TLR4/MD-2 monomer was determined by the ratio of the MFI values (obtained from MTS510 antibody staining) of the stimulated cells to those of the unstimulated cells were indicated. Cells were stained with anti-MHC class II or anti-CD40 antibodies.

Western Blotting and Myddosome Formation

For Western blotting, iMΦs (5×10$^6$) were stimulated with ligands for indicated periods, and subsequently lysed in 700 μL of lysis buffer containing 1% NP-40, 50 mM Tris-HCl (pH 7.4), 150 mM NaCl. Protease inhibitors and phosphatase inhibitors were added just prior to cell lysis. Immunoblotting was performed using standard molecular biology techniques.

For myddosome formation, iMΦs (3×10$^6$) were stimulated with ligands for indicated periods, and subsequently lysed in 700 μL of lysis buffer containing 1% NP-40, 50 mM Tris-HCl (pH 7.4), 150 mM NaCl. Protease inhibitors and phosphatase inhibitors were added just prior to cell lysis. Lysates were spun at top speed for 15 minutes at a table-top centrifuge in the cold room (at 4° C.). The cleared supernatants were collected and 80 μL of the supernatant was saved as total extract. 1 μg of the anti-MyD88 antibody and 15 μL (bed volume) of protein G Sepharose were added to the remaining supernatants and the incubation were allowed to proceed for overnight at 4° C. on a nutator. The beads were then washed for 3 times with lysis buffer, and 60 μL of SDS loading buffer was added. The protein complexes were further eluted by heating at 65° C. for 15 minutes. A portion of eluted protein complexes (20 μL) were separated by SDS-PAGE and visualized by western blotting using indicated antibodies.

Immunofluorescence

BMDCs cells were treated with LPS (1 μg/mL) for 3 hours before inflammasome-inducing stimuli challenge. For live or permeability experiment, MitotTacker CMX-ROS (Life Technologies) or Zombie Red (BioLegend) dyes were used in according to manufacturer's instructions before fixation with 4% paraformaldehyde. After permeabilization step using 0.1% Triton X-100 0.2% BSA-PBS, cells were blocked in 2% BSA-PBS and incubated with rabbit anti-ASC pAb (AL177, Adipogen) and mouse anti-caspase-1 mAb (Casper-1, Adipogen) followed by Alexa Fluor 488-conjugated chicken anti-rabbit IgG (Life Technologies) and Alexa Fluor 568-conjugated goat anti-mouse IgG (Life Technologies) diluted in blocking buffer. Nuclei were counterstained with DAPI (Life Technologies) or DRAQ5 (BioLegend). A Zeiss Axiovert 200M confocal microscope or an Olympus BX41 fluorescence microscope was used to acquire images.

PI Permeabilization Assay

BMDCs or BMMs were seeded into black 96-well tissue culture plates with transparent bottom and treated with priming stimuli for 3 h. After gently wash with PBS, 100 μl of pre-warmed staining solution (5 μM PI, 5% FBS, 20 mM HEPES, no phenol red containing $MgCl_2$ and $CaCl_2$) HBSS) was added to each well and incubated for 5 minutes at 37° C. 5% $CO_2$. Immediately before reading, 100 μL staining solution without PI containing 2× inflammasome-inducing stimuli was added into appropriate wells. 0.1% Triton X-100 was used as positive control for the maximum permeability. The increasing fluorescence intensity was recorded for 3 hours at 37° C. in continuum using a FLUOstar Omega microplate reader (BMG labtech) with 544 nm excitation and 620-10 nm emission filters.

In Vivo Immunization and In Vitro Re-Stimulation

WT C57BL/6NJ and Caspase-1/-11 dKO C57BL/6NJ mice were immunized on the upper back (one injection over each shoulder) with either 150 µg/mouse endotoxin-free OVA plus 7 µg/mouse LPS emulsified in incomplete Freund's adjuvant or with 150 µg/mouse endotoxin-free OVA, plus 65 µg/mouse oxPAPC, plus 7 µg/mouse LPS emulsified in incomplete Freund's adjuvant. CD4+ T cells were isolated from the draining lymph nodes 7 or 40 days after immunization by magnetic cell sorting with anti-CD4 beads (Miltenyi Biotech). The cells were seeded in 96-well plates at a concentration of 100,000 cells per well in the presence of 100,000 DC and of serial dilutions of OVA, starting at 1 mg/ml. Secretion of IFNγ, IL-17 and IL-2 were measured by ELISA 5 days later.

HSV Infections Assay of Viral Replication

Mice were housed in accordance with institutional and NIH guidelines on care and use of animals in research, and all procedures were approved by the Institutional Animal Care and Use Committee of Harvard Medical School. The indicated mouse strains were anesthetized in an isoflurane chamber followed by intraperitoneal injections of ketamine (3.7 mg/mouse) and xylazine hydrochloride (0.5 mg/mouse). The corneas were scarified, and infections were carried as described previously (Cliffe, A. R. et al., (2009) Journal of virology 83, 8182-8190). To measure viral replication in the eye, swabs of tear film were collected using sterile polyester applicators (Puritan) for the first 5 dpi, and virus in the tear films from the eye was titrated on Vero cells as described previously (Coen, D. M. et al., (1989) Proc Natl Acad Sci USA 86, 47364740).

Statistical Analysis

Hypotheses were tested with two-tail t-tests in single pairwise comparisons. p-values, calculated with Excel (Microsoft) are coded by asterisks: <0.05 (*), <0.01 (), <0.001 (*).

Example 2. Identification of oxPAPC as Both a TLR4 Antagonist and a CD14 Agonist Oxidized phospholipids such as oxPAPC have a confusing history, having been reported to act as either activators or inhibitors of inflammation. Some studies have demonstrated that oxPAPC can inhibit TLR4-dependent inflammatory cytokine expression induced by LPS in a concentration dependent manner (Bochkov, V. N. et al., (2002) Nature 419, 77-81; Erridge, C. et al., (2008) The Journal of biological chemistry 283, 24748-24759; Oskolkova, O. V. et al. (2010) J Immunol 185, 7706-7712), whereas others have reported oxPAPC to be an activator of TLR4-dependent inflammatory responses (Imai, Y. et al. (2008) Cell 133, 235-249; Shirey, K. A. et al. (2013) Nature 497, 498-502).

Figure 2:
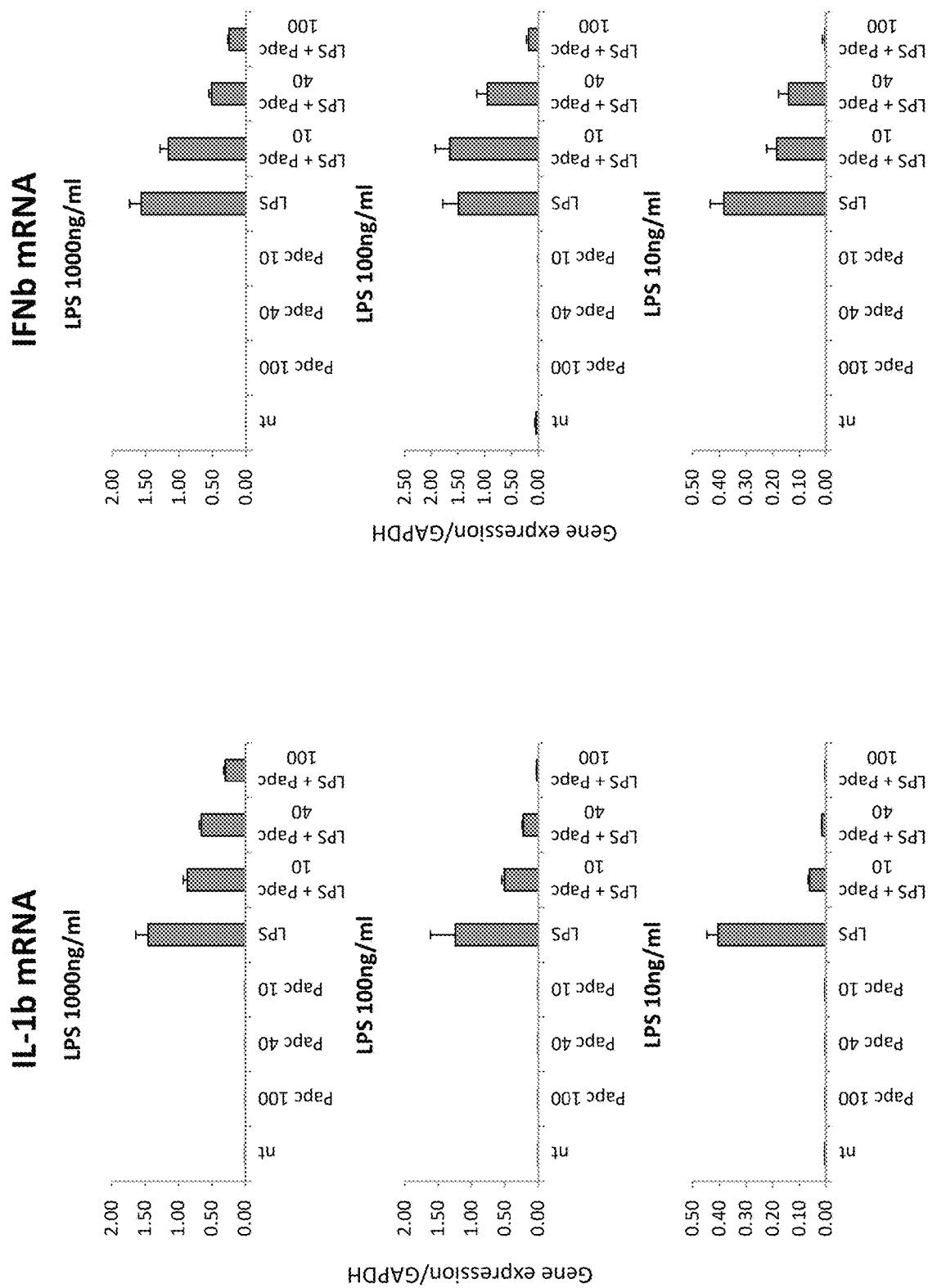
FIG. 2 shows that different doses of PAPCs modulated TLR4 signaling.

To determine the activities of oxPAPC and PAPC, the abilities of these lipids to engage the LPS receptors TLR4 and CD14 was examined in immortal murine bone marrow derived macrophages (BMDM; alternatively iMΦ) from mice. Side-by-side comparisons of LPS- and oxPAPC-stimulated cells were performed to assess the potential of these molecules to induce the expression of known TLR4-dependent genes (FIGS. 1 and 2). As compared to LPS, which induced the robust expression of the cytokines IL-1β and interferon beta (IFNβ) (FIG. 2), and the IFN-stimulated gene viperin, oxPAPC was unable to upregulate these genes (FIG. 43B). It was possible that other TLR4-dependent genes than those assayed were being activated by oxPAPC. Several concentrations of oxPAPC were assessed in these studies, all of which were similar to those reported to be present in inflamed or damaged tissues in vivo (Oskolkova, O. V. et al. (2010) J Immunol 185, 7706-7712). TLR4 dimerization was assessed by flow cytometry, using an antibody that only detects TLR4 monomers. Dimerization was identified to be induced by LPS, but not by oxPAPC treatment (FIG. 43A). To complement these analyses, the inducible interactions between the receptor-proximal proteins MyD88 and IRAK4 were also examined.

These proteins form a supramolecular organizing center (SMOC) called the myddosome (Kagan, J. C. et al., (2014) Nat Rev Immunol 14, 821-826; Lin, S. C. et al., (2010) Nature 465, 885-890; Motshwene, P. G. et al., (2009) J Biol Chem 284, 25404-25411), which was only assembled in response to TLR activation (Bonham et al., 2014). Thus, detection of a myddosome can be used as a general readout of TLR activation. Whereas LPS induced the formation of a MyD88-IRAK4-containing myddosome within 30 minutes of treatment, oxPAPC was unable to elicit any detectable association between these proteins (FIG. 43C, and 49A). Furthermore, oxPAPC-treated cells contained no detectable amounts of phosphorylated STAT1 or the IFN-stimulated gene viperin (FIG. 1, FIG. 43D, and FIG. 49B), both of which were abundant upon LPS treatment. These data indicated that oxPAPC was not a mimic of LPS, and had little or no ability to directly activate TLR4 directly in BMDM.

In cell-free or overexpression systems, oxPAPC acted as an inhibitor of TLR4 signaling events by competing with LPS for access to either CD14 or the LPS-binding protein MD-2 (Bochkov, V. N. et al., (2002) Nature 419, 77-81; Erridge, C. et al., (2008) The Journal of Biological Chemistry 283, 24748-24759), the latter of which was responsible for crosslinking and activating TLR4. However, the ability of oxPAPC to engage the TLR4 regulators has mainly been examined in cell-free systems or epithelial cells. The degree of inhibition by oxPAPC was affected by altering the ratio of LPS and oxPAPC administration (FIGS. 1-5), which indicated that these two factors were likely competing for the same binding site with CD14. Consistent with such competition over a single binding site, a mutant CD14 allele that could not bind LPS was not endocytosed even in the presence of oxPAPC or LPS.

Figure 3:
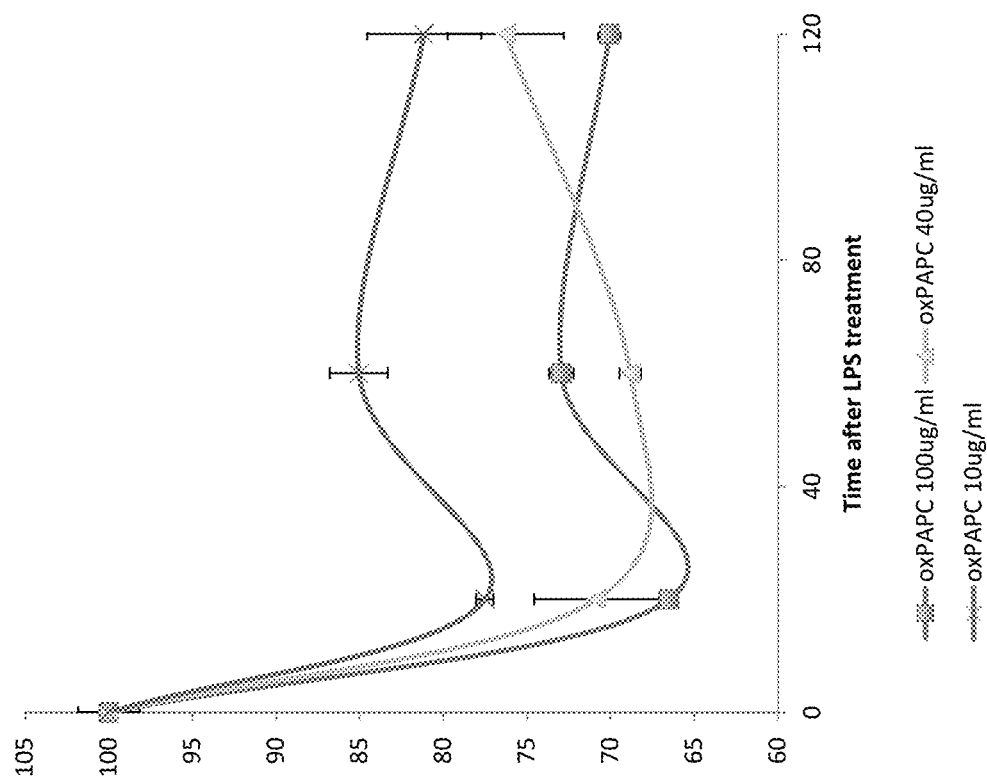
FIG. 3 shows that different doses of PAPCs modulated CD14 levels on the plasma membrane.
Figure 4:
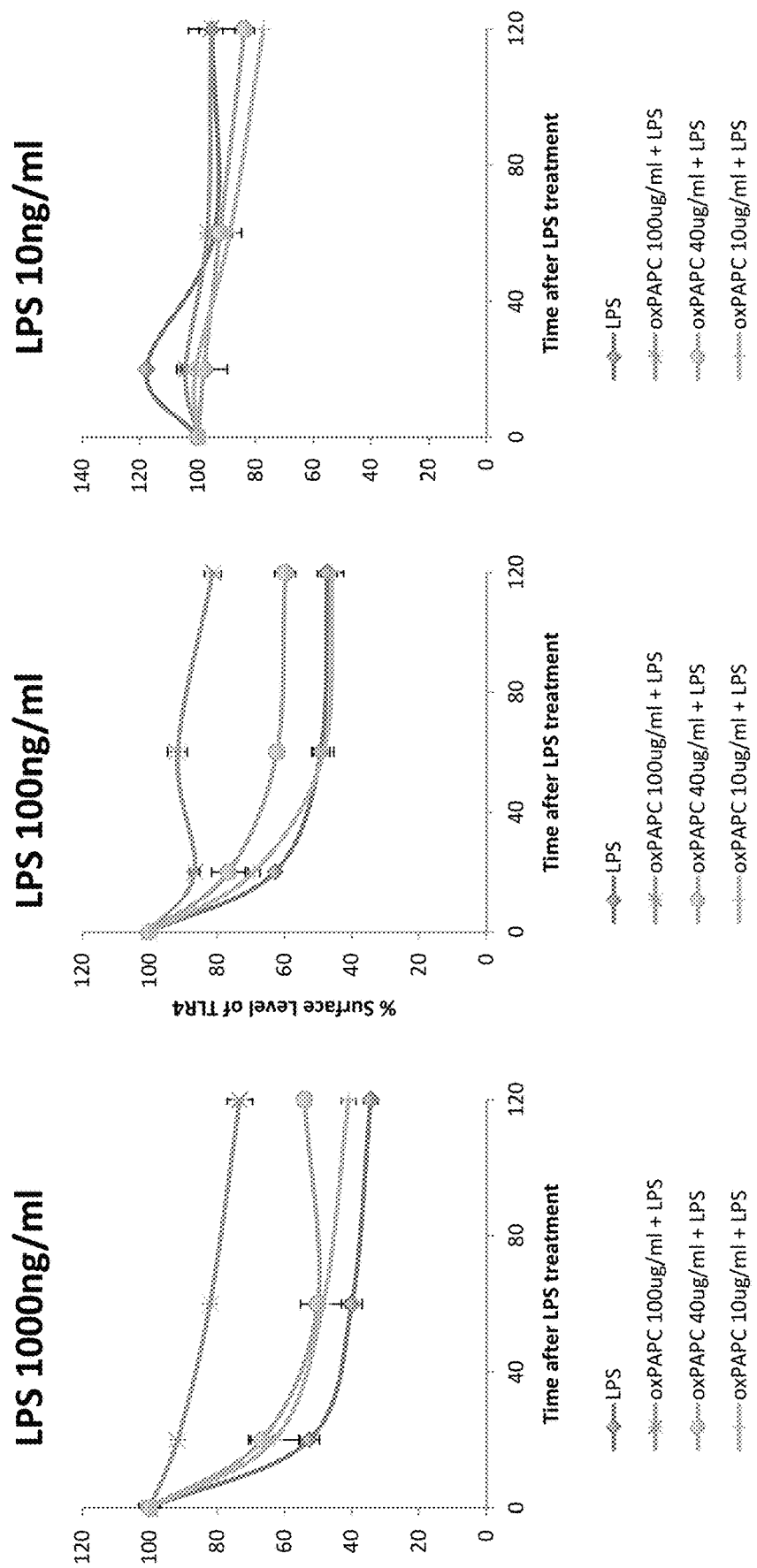
FIG. 4 shows that different doses of PAPCs modulated LPS-dependent TLR4 internalization.
Figure 5:
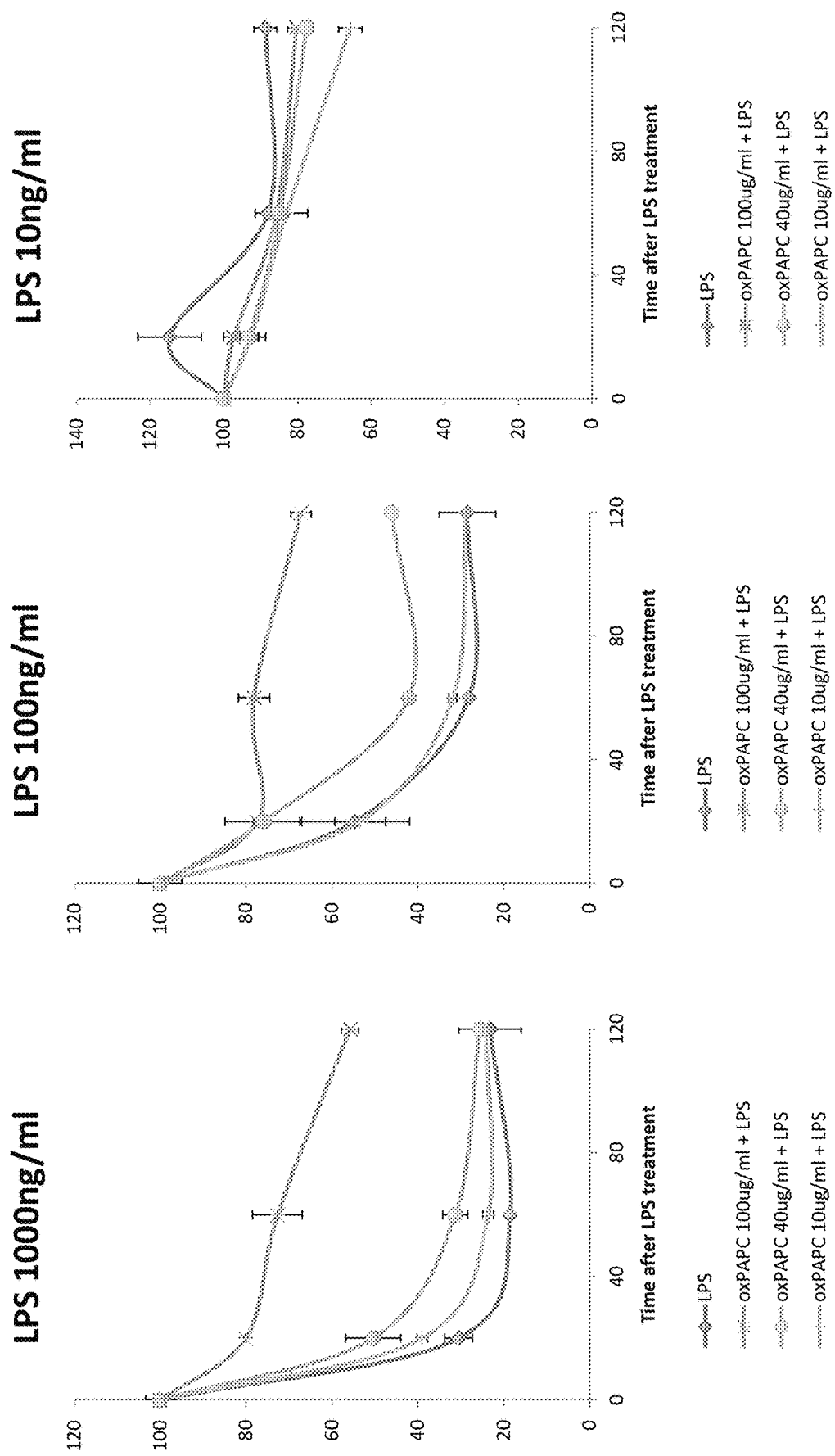
FIG. 5 shows that different doses of PAPCs modulated LPS-dependent TLR4 dimerization.

To determine if oxPAPC engaged CD14 in iMΦs or MD-2 in BMDM, several assays were used to monitor the inducible dimerization or endocytosis of candidate receptors by flow cytometry. As reported previously, LPS treatment caused the endocytosis of CD14 and TLR4, which resulted in the loss of surface staining for these proteins (Zanoni, I. et al., (2011) Cell 147, 868-880). Interestingly, oxPAPC was unable to induce the endocytosis of TLR4 (FIG. 4), but was able to promote rapid endocytosis of CD14 (FIG. 3, FIG. 44A, and FIG. 50A). This rapid internalization of CD14 induced by oxPAPC therefore created a CD14-deficiency at the cell surface. Without wishing to be bound by theory, it is believed that this deficiency of CD14 at the cell surface could explain the ability of this lipid to block TLR4 signaling. Indeed, oxPAPC treated cells that were subsequently treated with LPS exhibited defects in TLR4 endocytosis and TLR4-induced gene expression.

CD14 surface abundance resulted from the antagonistic actions of CD14 endocytosis and resynthesis (Tan, Y. et al., (2015). Immunity 43, 909-922), and was most clearly observed under conditions that prevent the latter. Consequently, the extent of oxPAPC- or LPS-induced CD14 endocytosis was enhanced under conditions where protein synthesis was blocked with cycloheximide (FIG. 50B). Cycloheximide treatment did not affect either TLR4 internalization or dimerization (FIGS. 50C and 50D). Primary bone marrow derived MΦ and bone marrow derived DCs behaved similarly to iMΦ, in that oxPAPC promoted CD14 endocytosis, but not TLR4 dimerization or endocytosis (FIG. 44B). The endocytosis of CD14 (but not TLR4) induced by oxPAPC therefore created a CD14-deficiency at the cell surface, which likely explains the ability of this lipid to block TLR4 signaling. Indeed, oxPAPC-treated cells that were subsequently treated with LPS exhibited defects in TLR4 dimerization, endocytosis, TNFα secretion and STAT1 phosphorylation, with the latter two being classic readouts of TLR4 signaling (FIGS. 44A and 44F).

To address the possibility that CD14 used a similar mechanism to interact with a PAMP (LPS) and a DAMP (oxPAPC), the amino acids within CD14 required for interactions with these lipids were examined. The LPS-binding domain of CD14 was previously identified to be a large hydrophobic pocket that is comprised of four distinct regions of the primary amino acid sequence (Kim, J. I. et al., (2005) J Biol Chem 280, 1134711351). CD14 alleles that contained mutations in either one region (1R) or two regions (2R) retained the ability to form a complex with biotinylated LPS, whereas mutations of all four regions (4R) in CD14 abolished LPS-binding activity (Tan, Y. et al., (2015). Immunity 43, 909-922). Each of these mutant CD14 alleles encoded full-length folded proteins that were transported to the cell surface (Tan, Y. et al., (2015). Immunity 43, 909-922). Notably, the 4R mutant was also defective for interactions with biotinylated oxPAPC (FIG. 44E). Furthermore, when stably introduced into CD14 knockout (KO) iMΦ, the 4R mutant CD14 was not internalized in response to LPS or oxPAPC treatments (FIG. 44F). These data therefore indicated the same amino acids within CD14 promoted interactions with a DAMP (oxPAPC) and a PAMP (LPS), and provided molecular support for the conclusion that oxPAPC can be considered a selective LPS mimic (i.e. in the case of CD14-dependent activities). Overall, these data indicated that oxPAPC was not an activator of TLR4, but was an activator of CD14. This ability to dissociate CD14 and TLR4 endocytosis likely explains how oxPAPC functions as a TLR4 antagonist.

Example 3. oxPAPC Promoted the Activation of the NLRP3 Inflammasome in Dendritic Cells (DCs)

While the above example indicated that oxPAPC was not an activator of inflammation, some studies have demonstrated a pro-inflammatory function of these lipids (Imai, Y. et al. (2008) Cell 133, 235-249; Shirey, K. A. et al. (2013) Nature 497, 498-502). It was considered that some DAMPs could not elicit pro-inflammatory responses from naïve cells, but that they could induce cytokine release from cells previously exposed to microbial products. For example, extracellular ATP was described to have activated inflammasome-dependent release of IL-1β from cells that had been primed with TLR ligands (Petrilli, V. et al., (2007) Current opinion in immunology 19, 615-622).

Figure 7:
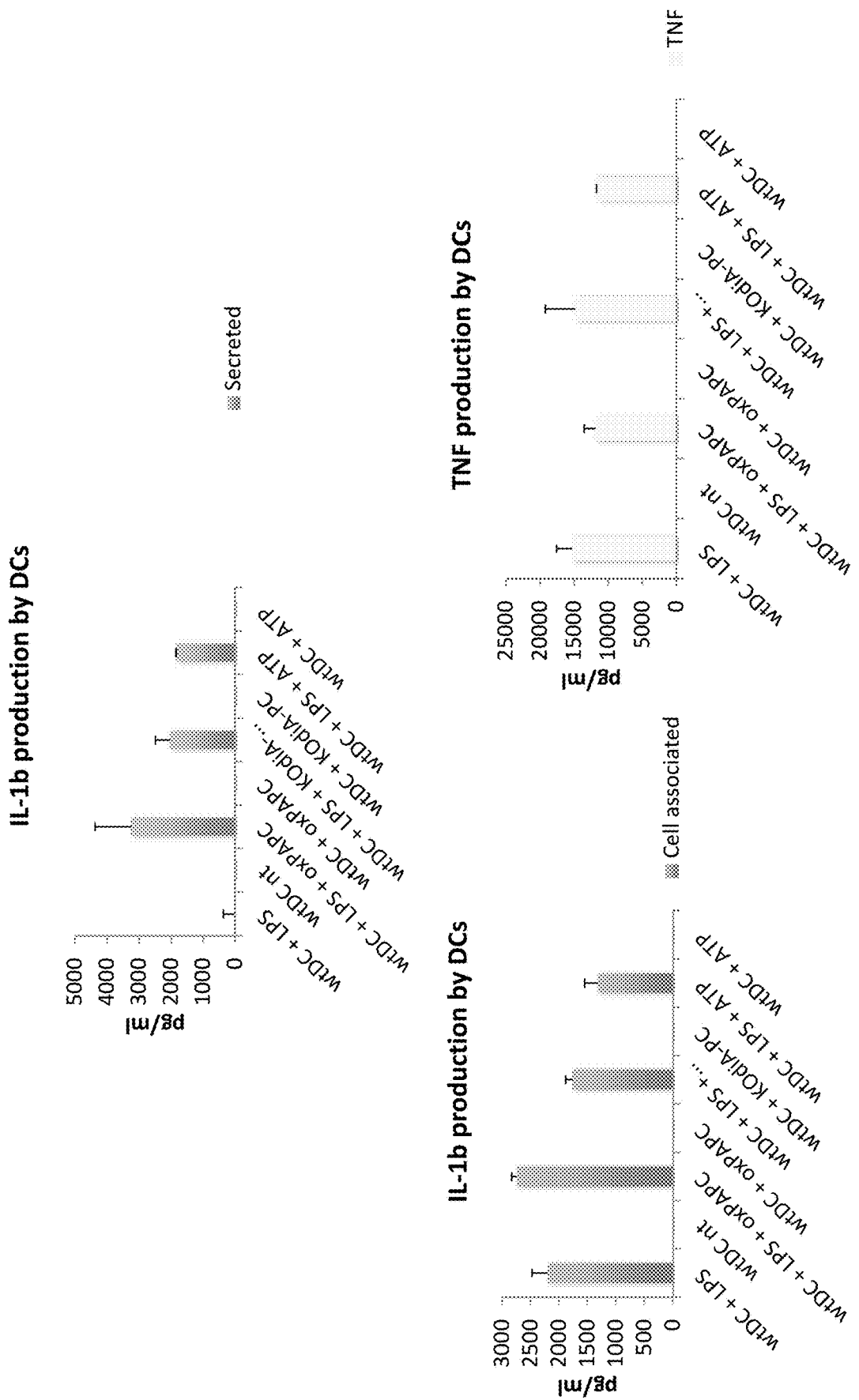
FIG. 7 shows that KOdiA-PC activated the inflammasome.

As shown in FIGS. 6 and 7, PAPCs, including oxPAPC component lipid KOdiA-PC (1-(Palmitoyl)-2-(5-keto-6-octene-dioyl) phosphatidylcholine), activated the inflammasome in DCs.

Figure 9:
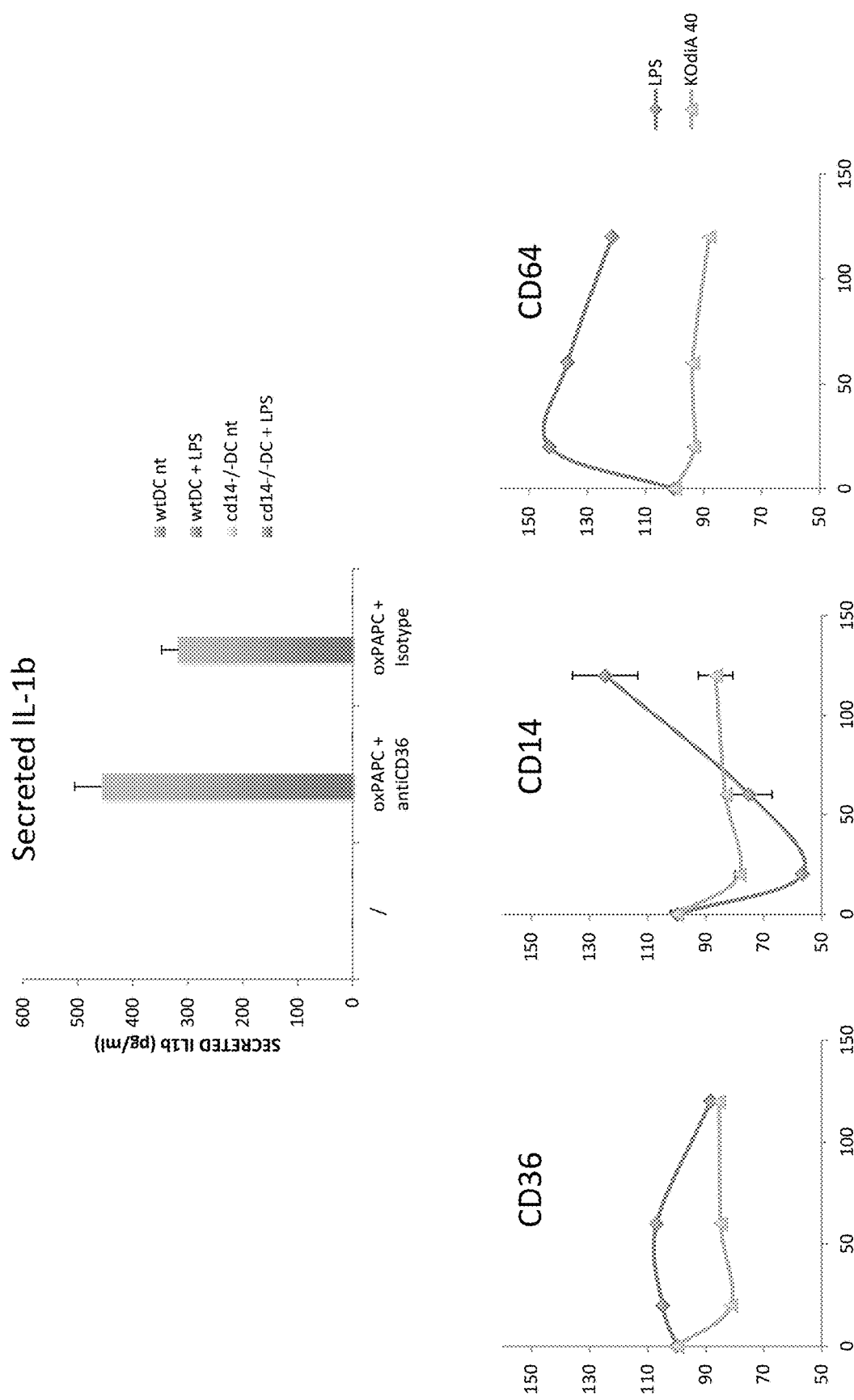
FIG. 9 shows that inflammasome activation in response to PAPCs was CD14 specific, although PAPCs could also induce CD36 internalization.
Figure 10:
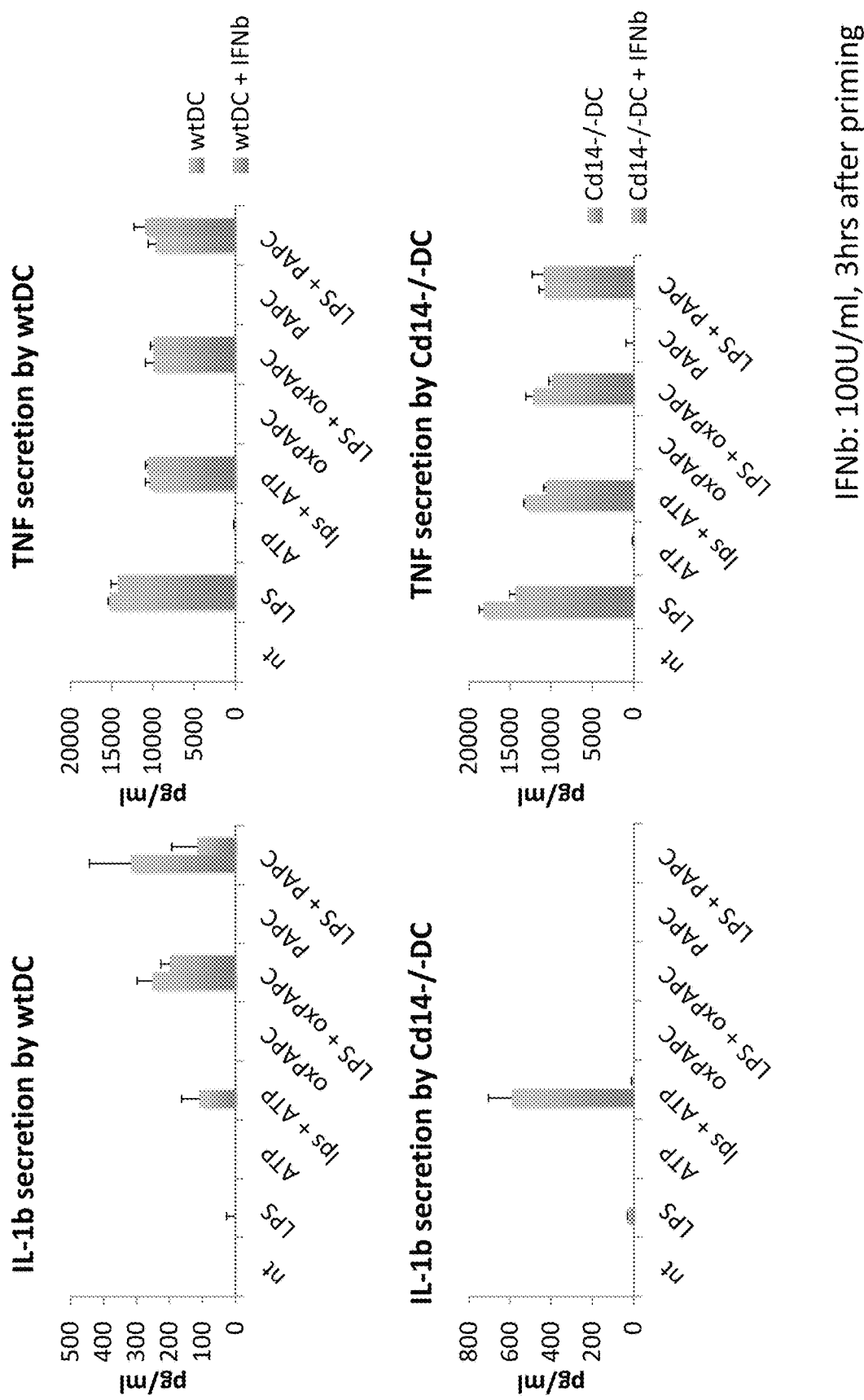
FIG. 10 shows that CD14 regulated PAPCs-mediated inflammasome activation independently of Type I IFNs.

As shown in FIG. 8, CD14 regulated inflammasome activation in response to PAPCs. Inflammasome activation in response to PAPCs was CD14 specific, although PAPCs could also induce CD36 internalization (FIG. 9). CD14 regulated PAPCs-mediated inflammasome activation independently of Type I IFNs (FIG. 10).

Figure 11:
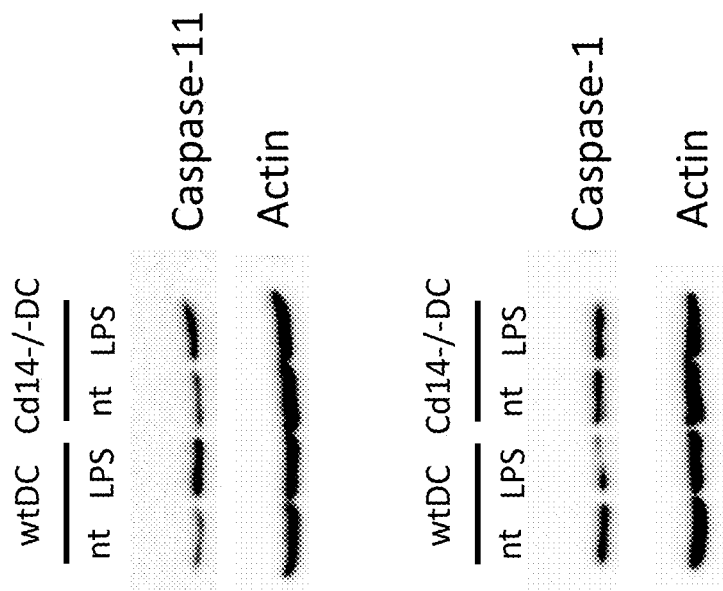
FIG. 11 shows that regulation of Caspase-1 and Caspase-11 expression was similar in wtDCs and Cd14−/−DCs.
Figure 12:
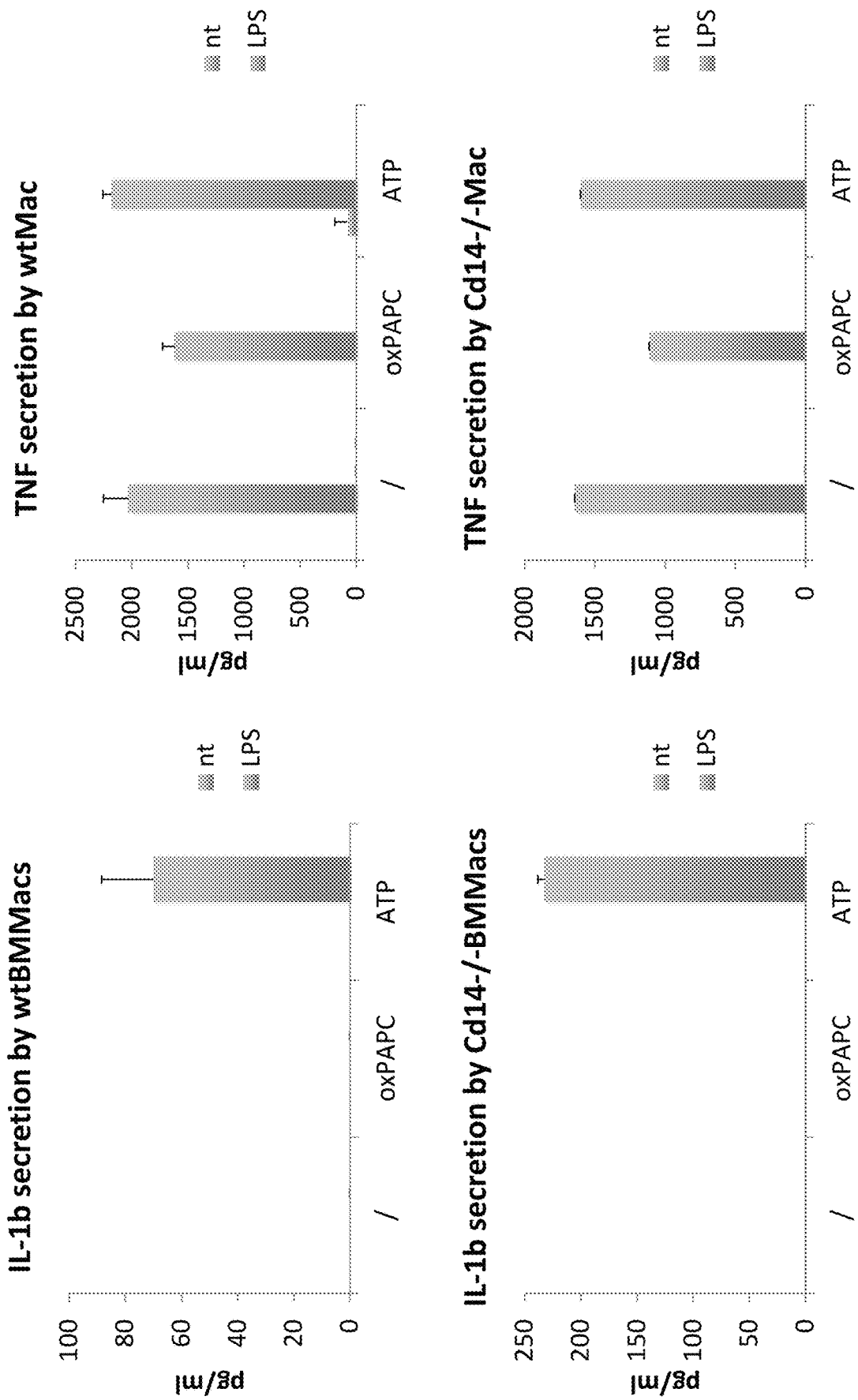
FIG. 12 shows that PAPCs induced inflammasome activation in a cell type specific manner.

Regulation of Caspase-1 and Caspase-11 expression was similar in wt DCs and Cd14−/−DCs (FIG. 11). PAPCs induced inflammasome activation in a cell type specific manner (FIG. 12).

Figure 13:
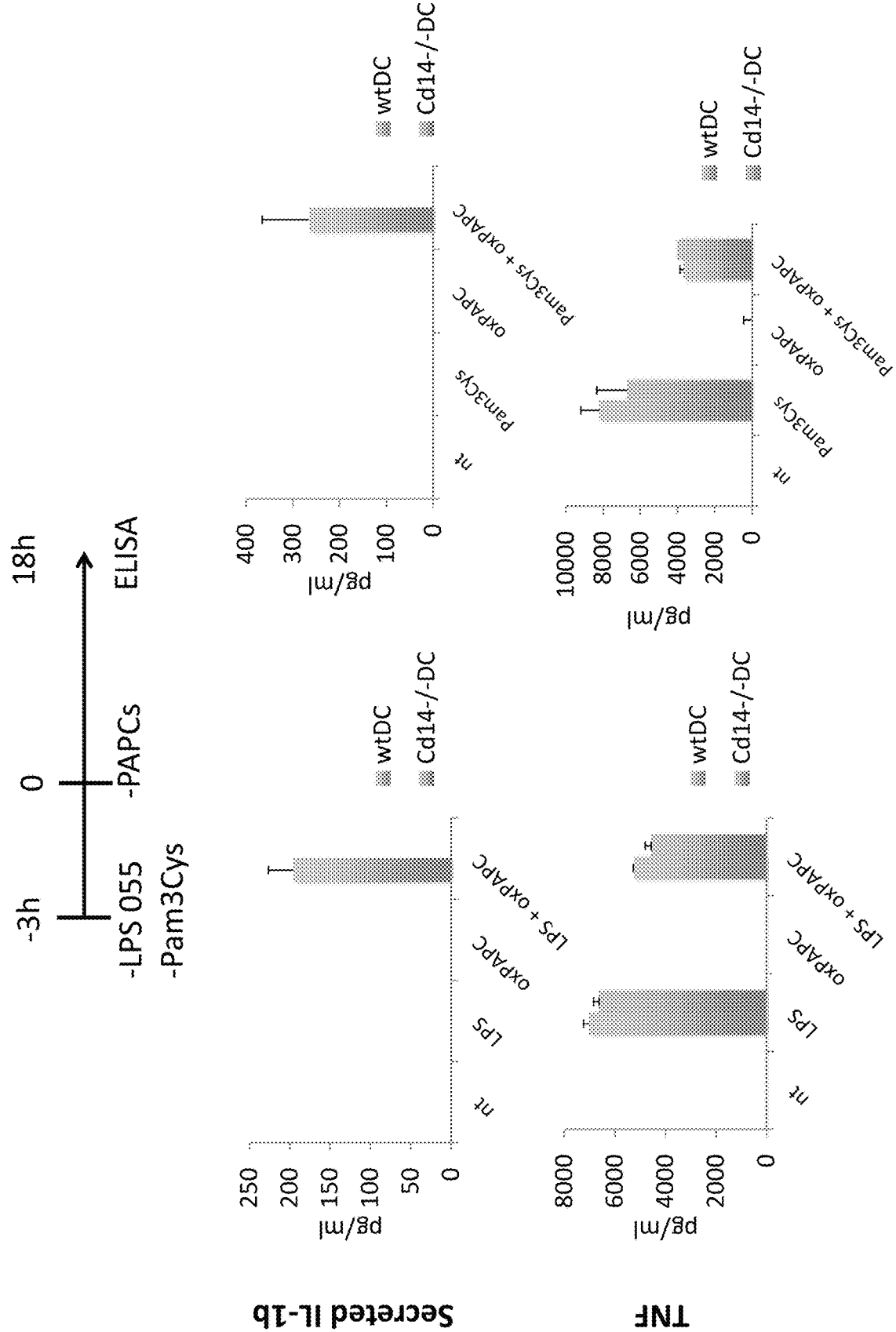
FIG. 13 shows that other PAMPs primed PAPCs-induced inflammasome activation.
Figure 14:
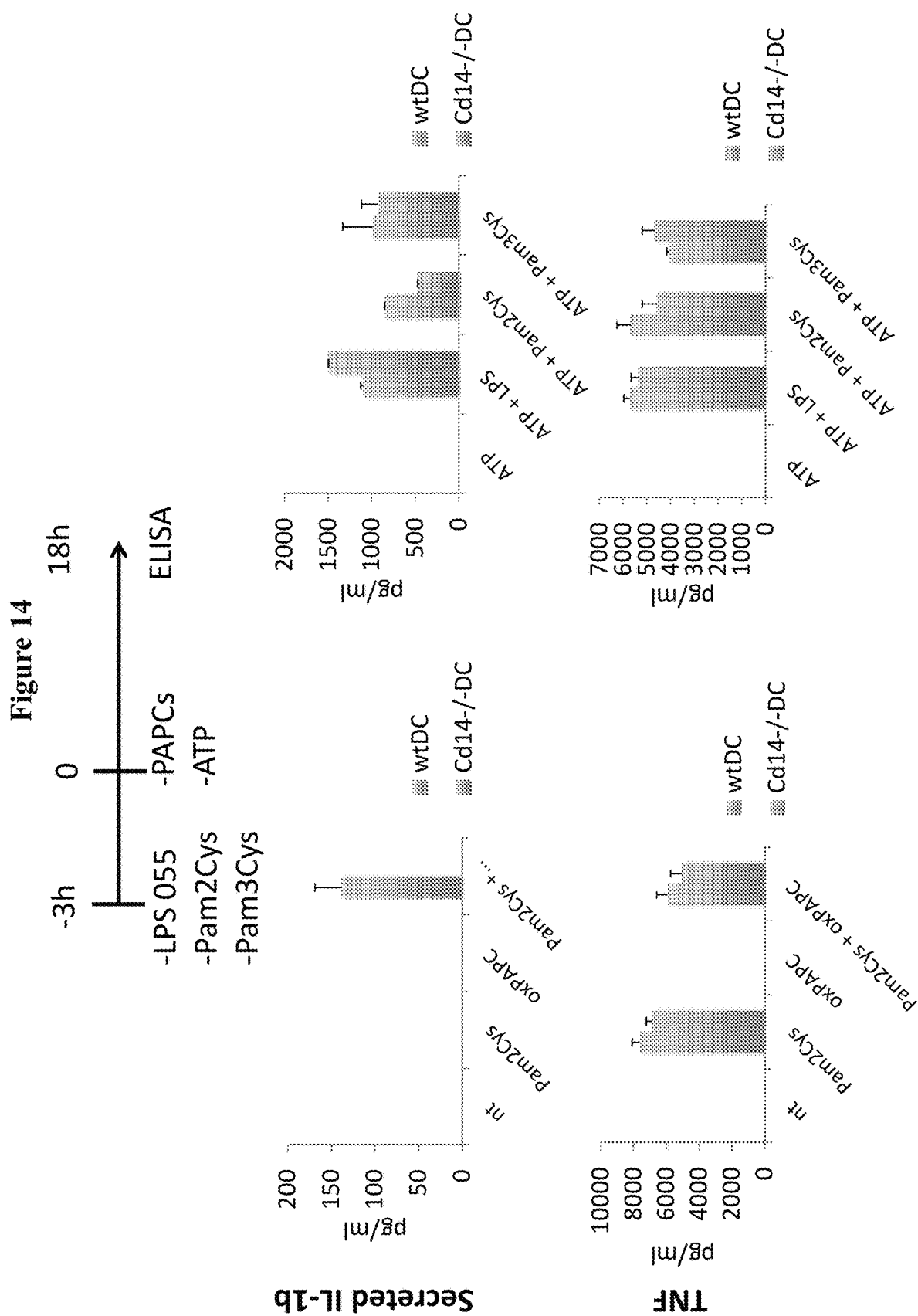
FIG. 14 shows additional results that other PAMPs primed PAPCs-induced inflammasome activation.

It was also identified that other PAMPs primed PAPCs-induced inflammasome activation (FIGS. 13 and 14).

Figure 15:
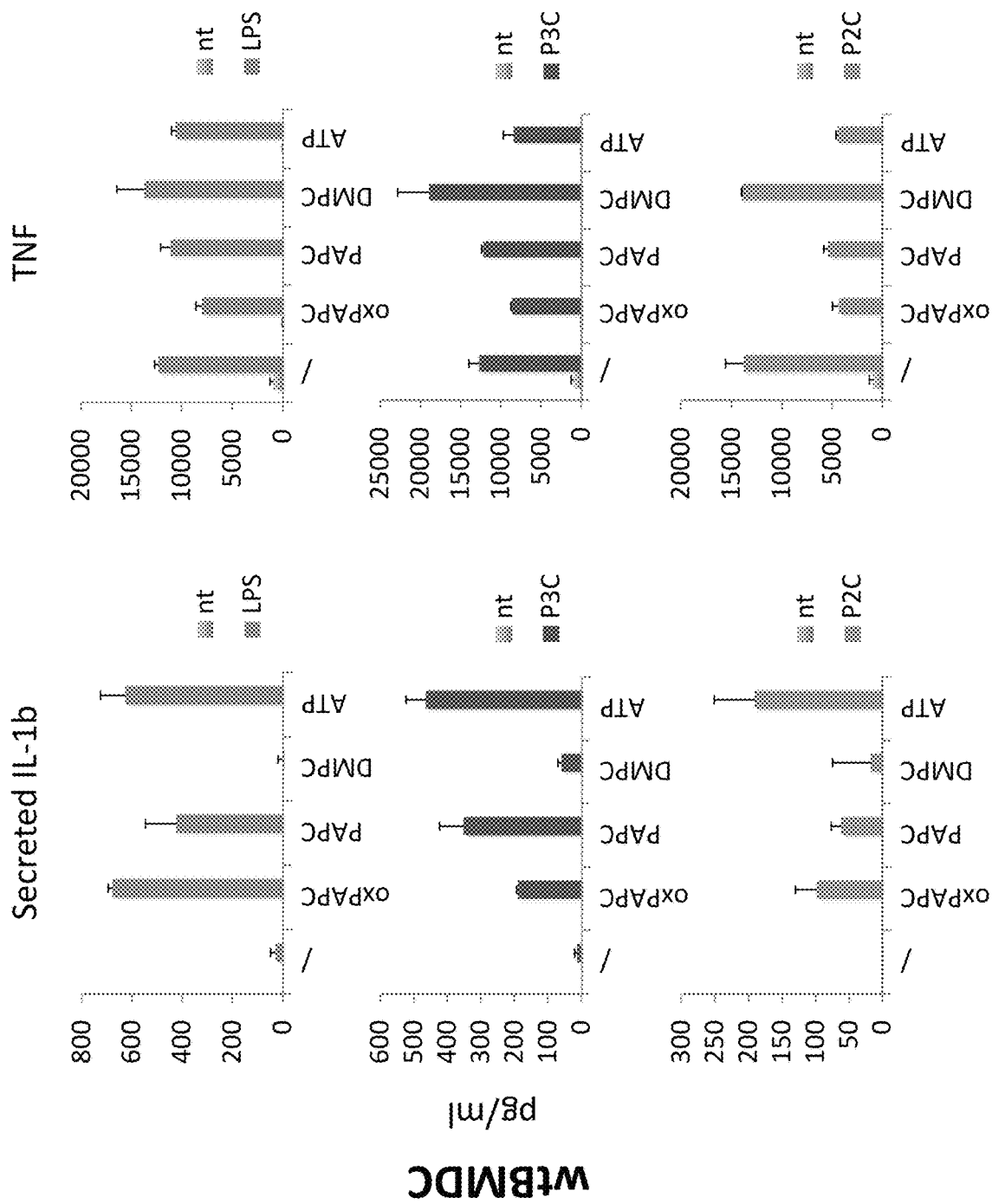
FIG. 15 shows that not all modified PCs induced inflammasome activation.

Notably, not all modified PCs induced inflammasome activation (FIG. 15).

To determine whether oxPAPC had pro-inflammatory functions in a context-dependent way, the release of IL-1β from primary BMDM or BMDC that were pretreated (or not) with LPS was examined. Consistent with previous observations (Petrilli, V. et al., (2007) Current opinion in immunology 19, 615-622), LPS-pretreatment enabled ATP to elicit IL-1β release from DCs in a dose-dependent manner (FIG. 51A). Remarkably, oxPAPC had similar activities, but in a cell-type dependent manner. Interestingly, oxPAPC was also able to induce IL-1β secretion, but only in LPS-primed DCs (FIG. 45A). oxPAPC did not induce IL-1β release from naïve cells, but LPS pretreatment of DCs enabled oxPAPC to promote IL-1β release in a dose-dependent manner (FIG. 45A, and FIG. 51B).

Without wishing to be bound by theory, IL-1β release is typically mediated by inflammasomes, which are cytoplasmic complexes of proteins that trigger the processing and atypical secretion of IL-1β family members (Petrilli, V. et al., (2007) Current opinion in immunology 19,615-622).

Figure 16:
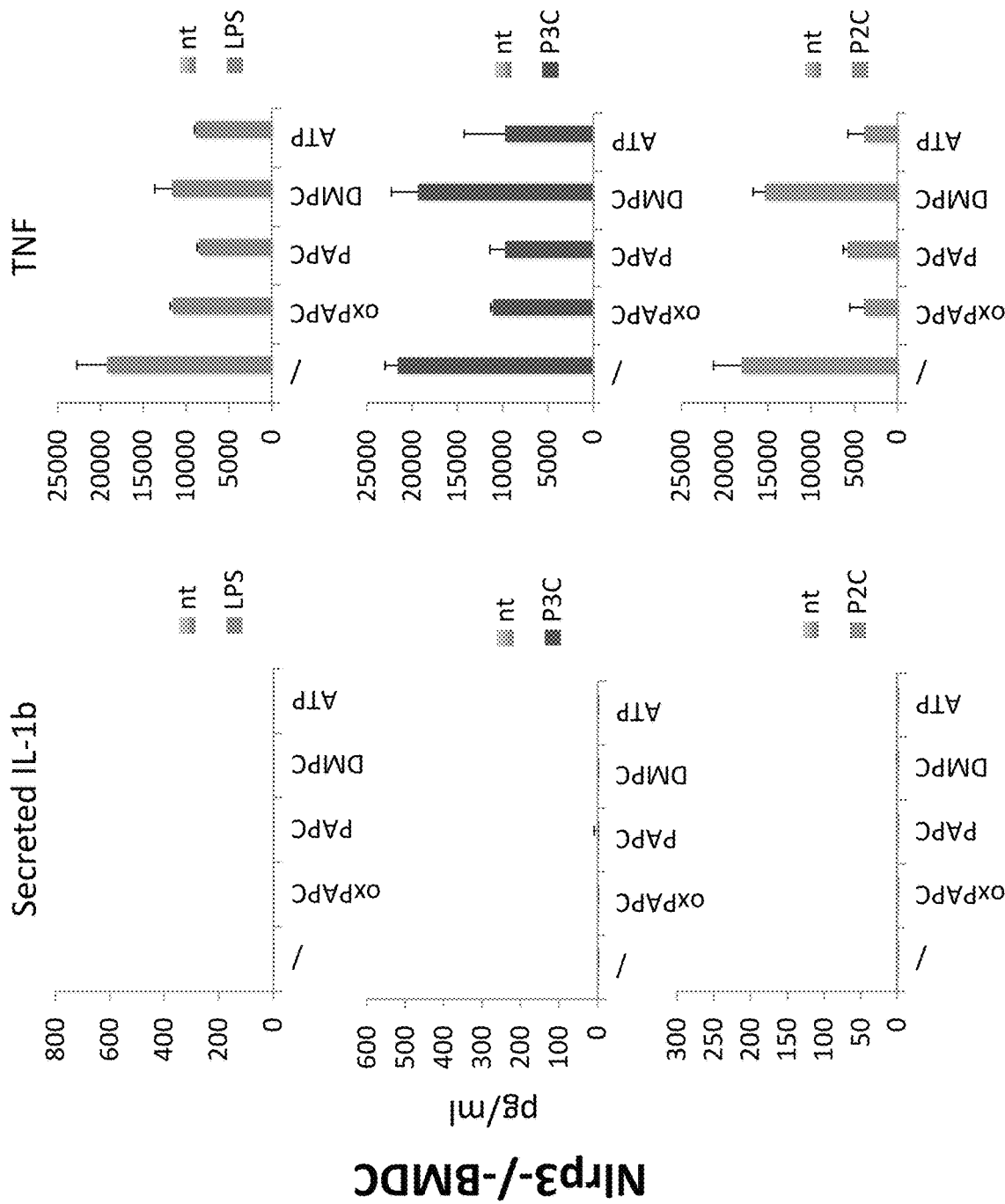
FIG. 16 shows that Nlrp3 was required to induce inflammasome activation.
Figure 17:
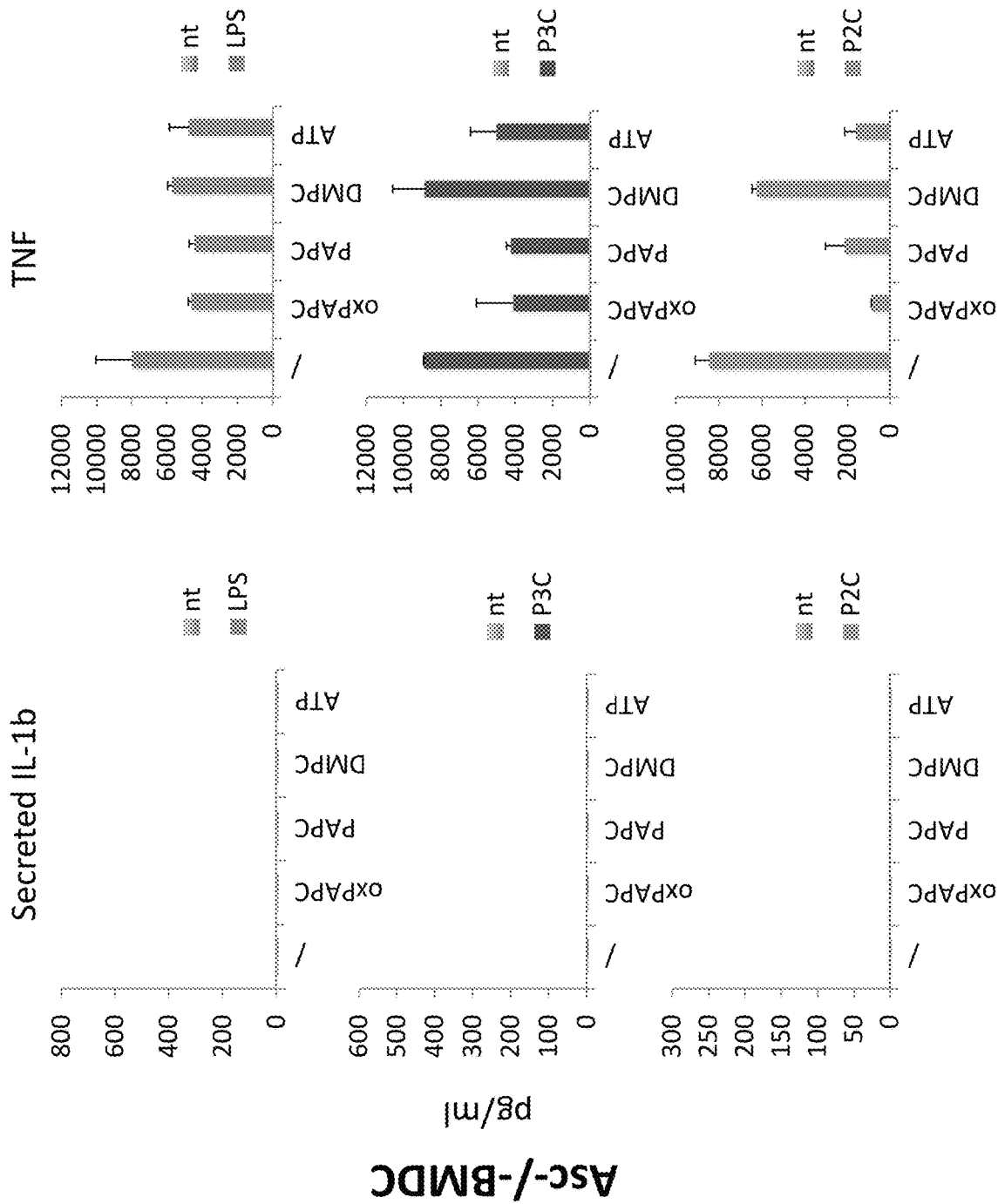
FIG. 17 shows that Asc was required to induce inflammasome activation.
Figure 18:
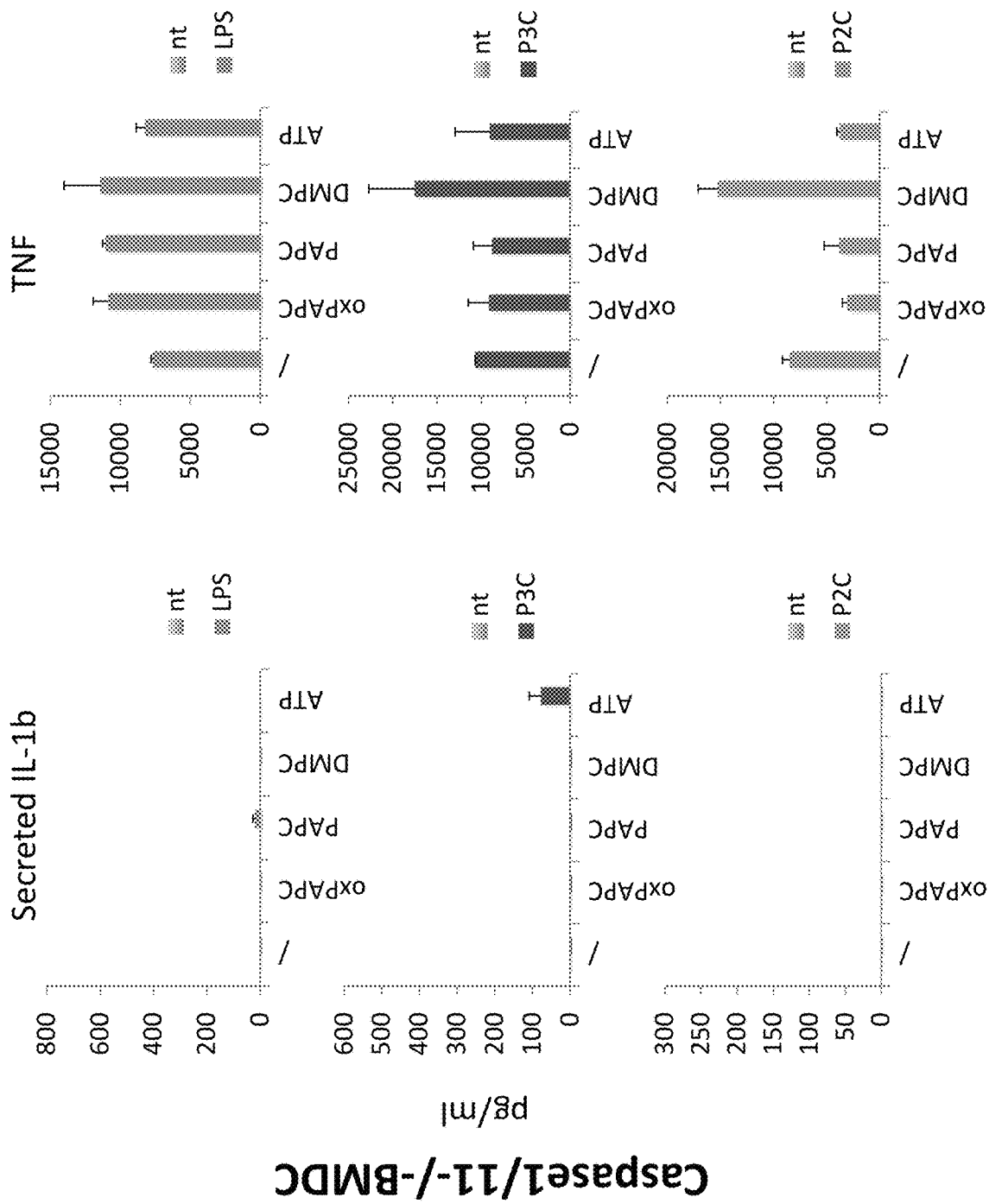
FIG. 18 shows that Casp1/Casp11 were required to induce inflammasome activation.

To determine whether the above-identified oxPAPC-mediated release of IL-1β was an inflammasome-dependent event, the activities of this lipid were examined in BMDCs derived from either caspase-1/caspase-11 double knockout (KO) mice, or mice lacking ASC (also known as Pycard), which was a common adaptor protein involved in inflammasome assembly (Martinon, F. et al., (2002) Molecular cell 10, 417-426). oxPAPC (or ATP) mediated release of IL-1β was completely lost from BMDCs lacking caspase-1/-11 (FIG. 18) or ASC (FIG. 17, and FIGS. 45B-C), an observation that provided definitive genetic proof for the requirement of inflammasome(s) in oxPAPC-induced cellular responses. Noting that NLRP3 was among the most common upstream activators of inflammasomes (Ye, Z., and Ting, J. P. (2008) Current opinion in immunology 20, 3-9), oxPAPC-mediated IL-1β release was also examined in NLRP3-deficient BMDCs. oxPAPC-mediated IL-1β release was thus identified as an NLRP3-dependent process, as oxPAPC was unable to induce IL-1β release from NLRP3-deficient BMDCs (FIG. 16), and from NLRP3 KO DCs (FIG. 45D). ATP-mediated IL-1β was also NLRP3 dependent, as expected. Importantly, no inflammasome regulator was required for TNFα secretion (FIGS. 45B-45D), which indicated that TLR4-induced gene expression occurred independent of inflammasome activation.

Commercially available (and natural) oxPAPC contains a mixture of different oxidized species. To determine whether alternative sources of oxPAPC yielded similar activities, a custom-made oxPAPC identified to be enriched in PEIPC (1-palmitoyl-2-(5,6 epoxyisoprostanoyl)-sn-glycero-3-phosphocholine), the most active component of oxPAPC (Springstead et al., 2012), was used. Side-by-side analysis of the two different oxPAPCs yielded similar results (FIG. 45A), confirming that independent of the source, oxPAPC induced IL-1β release in LPS-primed DCs. In contrast to the effects observed for IL-1β release, cell-associated IL-1β levels were similar when comparing cells stimulated with LPS alone, LPS/oxPAPC or LPS/ATP (FIGS. 45A, 51B, and 51C). This latter observation was consistent with the finding that oxPAPC could only act as an inhibitor of TLR4 signaling if cells were pretreated with this DAMP.

Figure 19:
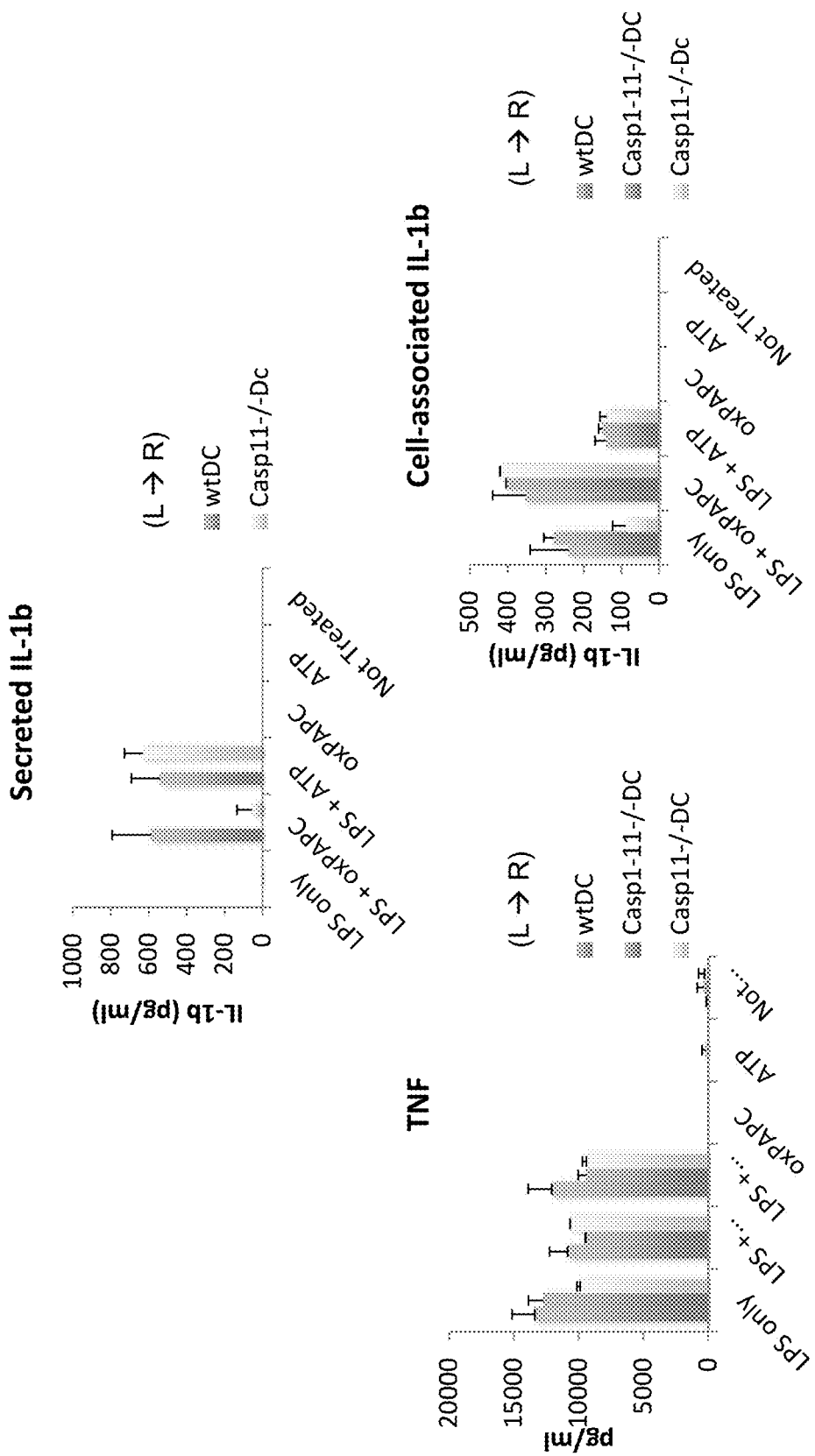
FIG. 19 shows that oxPAPC-induced inflammasome activation, but not ATP-induced inflammasome activation, was Caspase-11 dependent.
Figure 20:
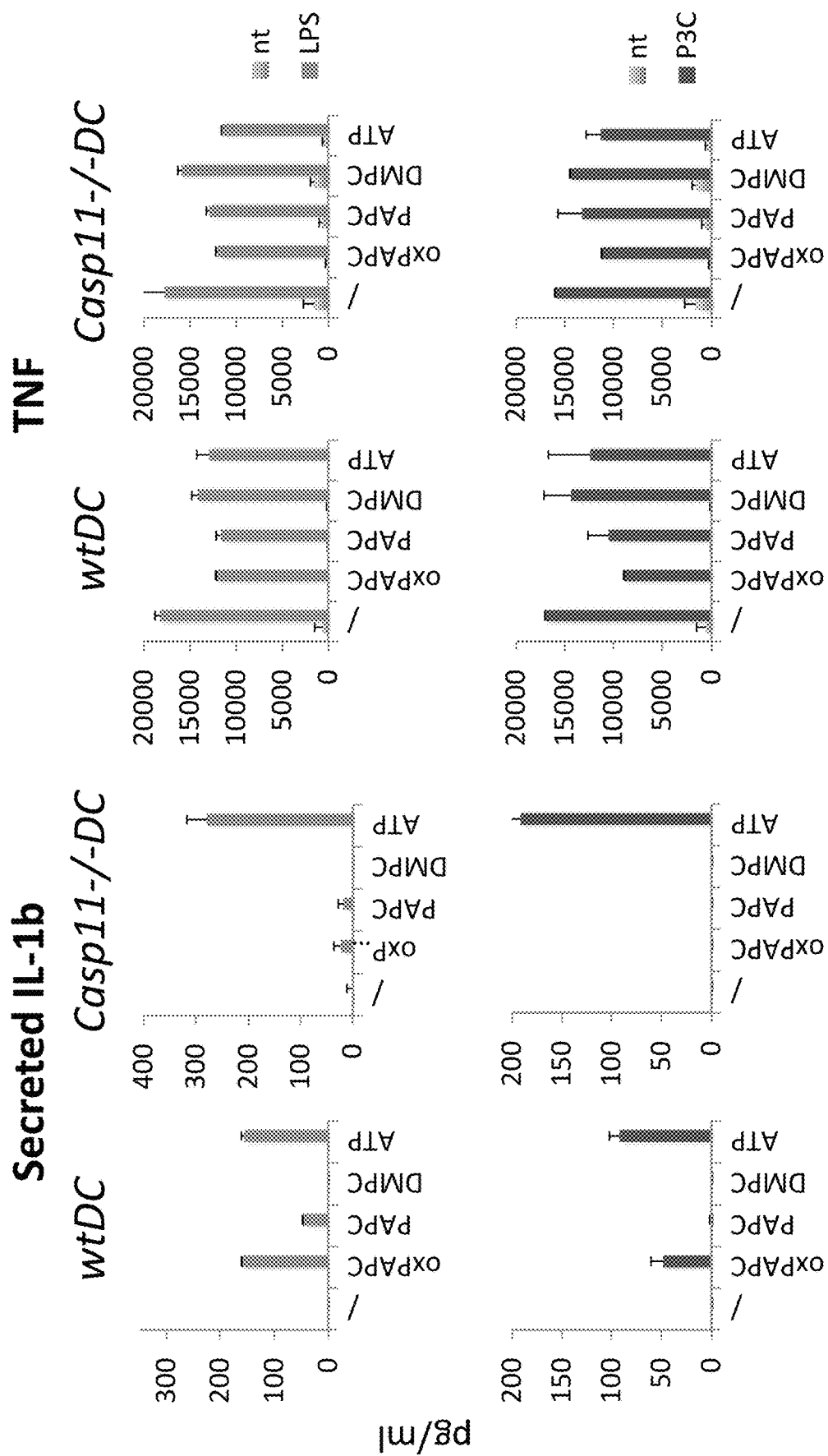
FIG. 20 shows that PAPCs-induced inflammasome activation after priming with both LPS and Pam3 required Caspase-11.

To determine the specificity of the effects of oxPAPC on inflammasome-mediated events (e.g., IL-1β release), the effect of this lipid upon the release of a classic TLR-dependent cytokine, TNFα was examined. oxPAPC neither promoted nor inhibited the release of TNFα from DCs (FIG. 51D). Additionally, when DCs were co-treated at the same time with LPS/ATP or LPS/oxPAPC (i.e. no priming), IL-1β was released only by oxPAPC-treated DCs (FIG. 51E), which indicated differences in the capacity of these two DAMPs to regulate IL-1β secretion. When a different phosphocholine variant, 1,2-dimyristoyl-sn-glycero-3-phosphocholine (DMPC) was used, it was unable to elicit IL-1β release (FIG. 51F). In contrast, a purified component of oxPAPC, 1-(Palmitoyl)-2-(5-keto-6-octene-dioyl) phosphatidylcholine, or KOdiA-PC, was able to elicit IL-1β secretion (FIG. 51F). In all cases, TNF secretion was not affected by phosphocholine treatment (FIG. 51F). These data established the specific ability of oxPAPC to promote IL-1β release, without affecting TLR4 signal transduction in LPS-primed DCs.

oxPAPC-induced inflammasome activation, but not ATP-induced inflammasome activation, was Caspase-11 dependent (FIG. 19). Indeed, PAPCs-induced inflammasome activation after priming with both LPS and Pam3 required Caspase-11 (FIG. 20). Thus, biotinylated forms of PAPCs were contemplated as a tool for study of Caspase-11 activation.

Figure 21:
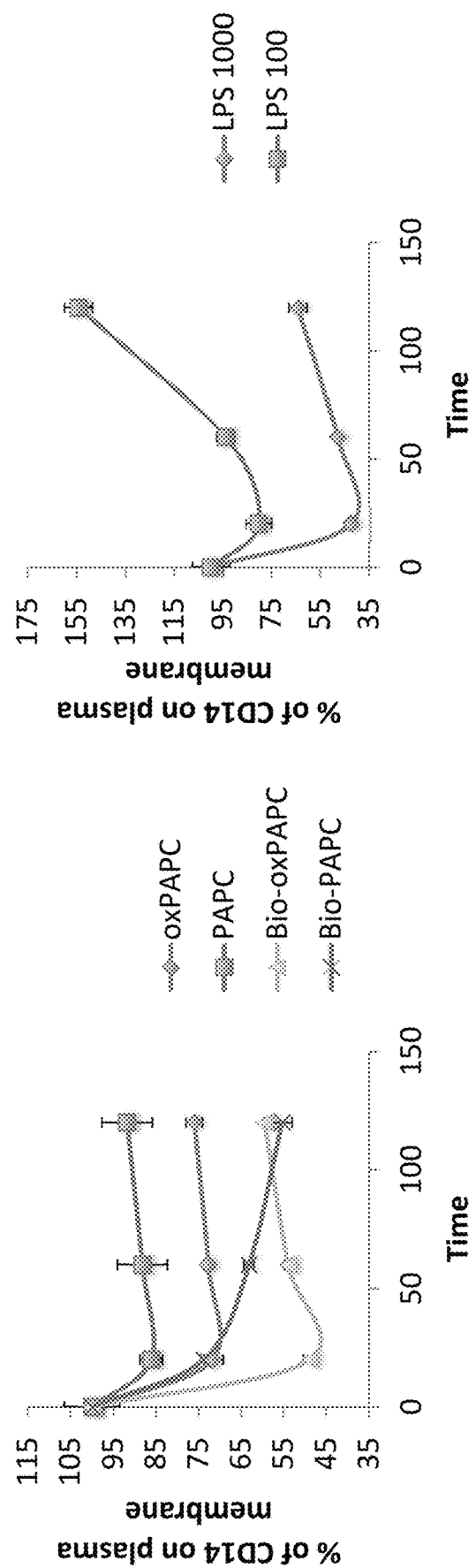
FIG. 21 shows that biotinylated PAPCs potently induced CD14 internalization.
Figure 22:
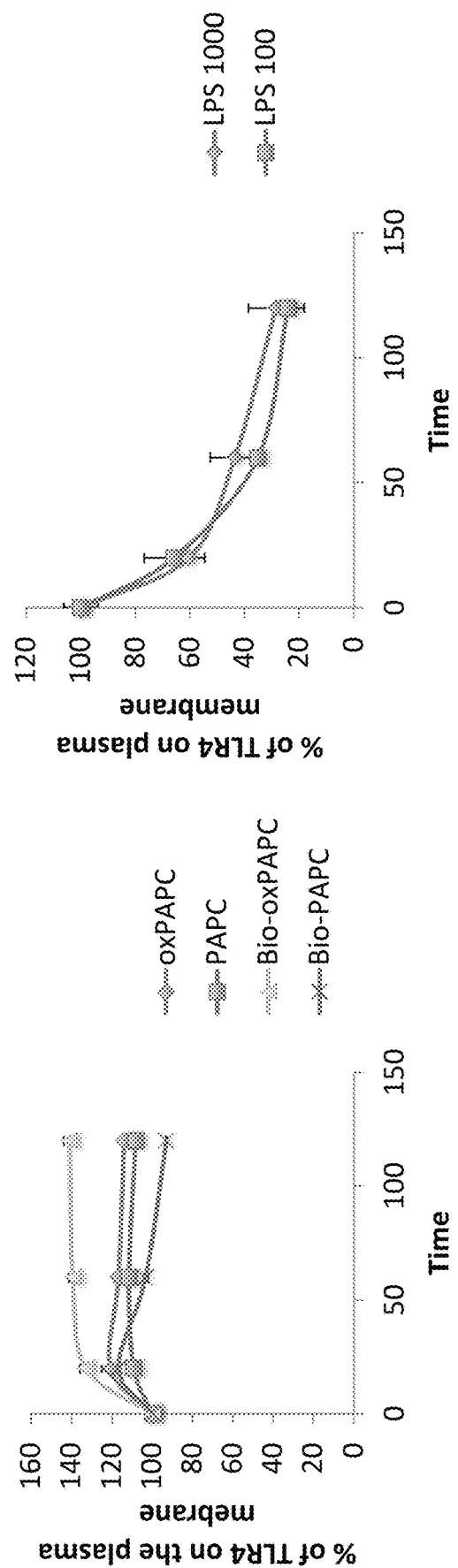
FIG. 22 shows that biotinylated PAPCs did not induce TLR4 internalization.
Figure 23:
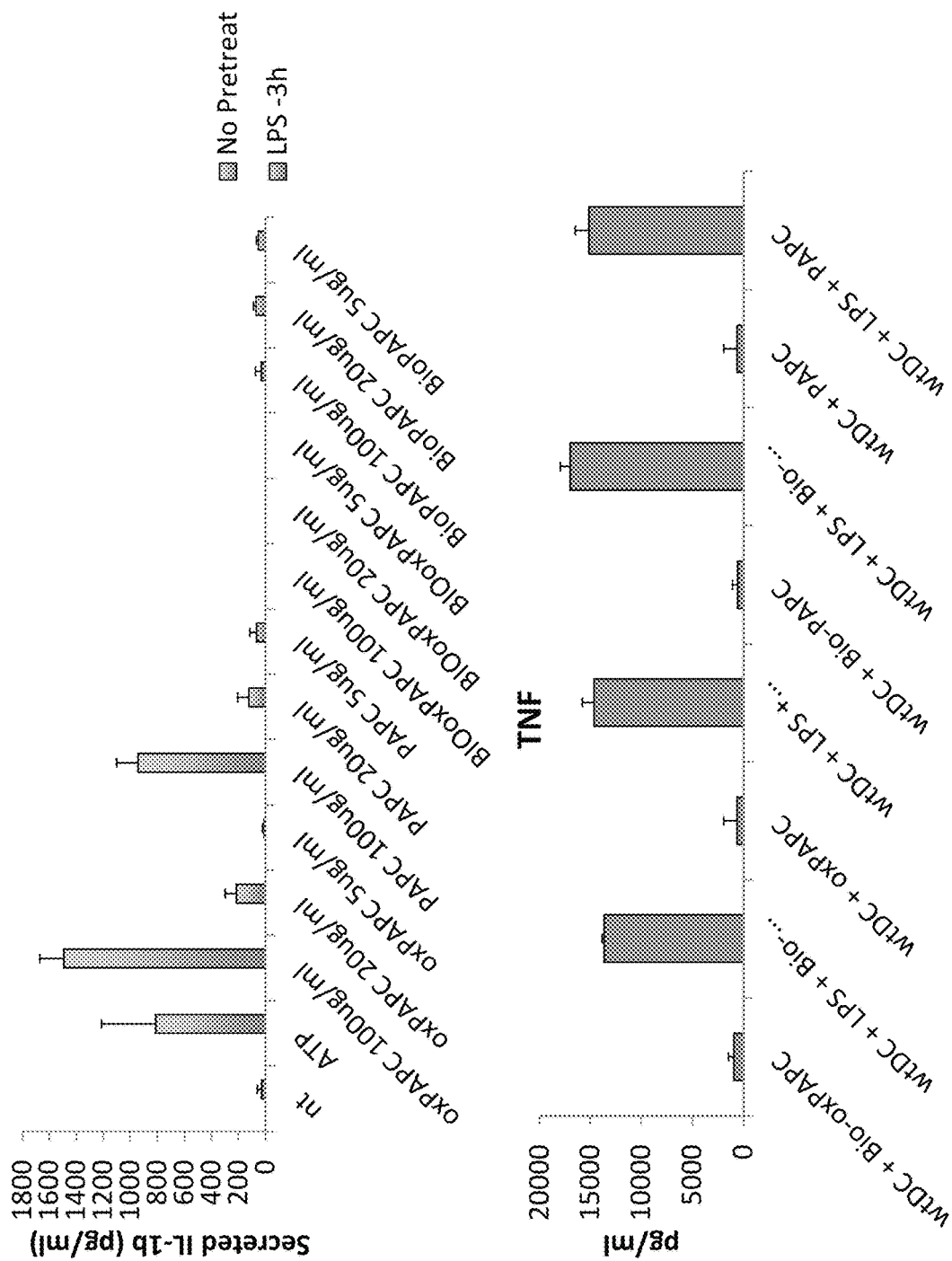
FIG. 23 shows that biotinylated PAPCs did not induce IL-1b secretion.
Figure 24:
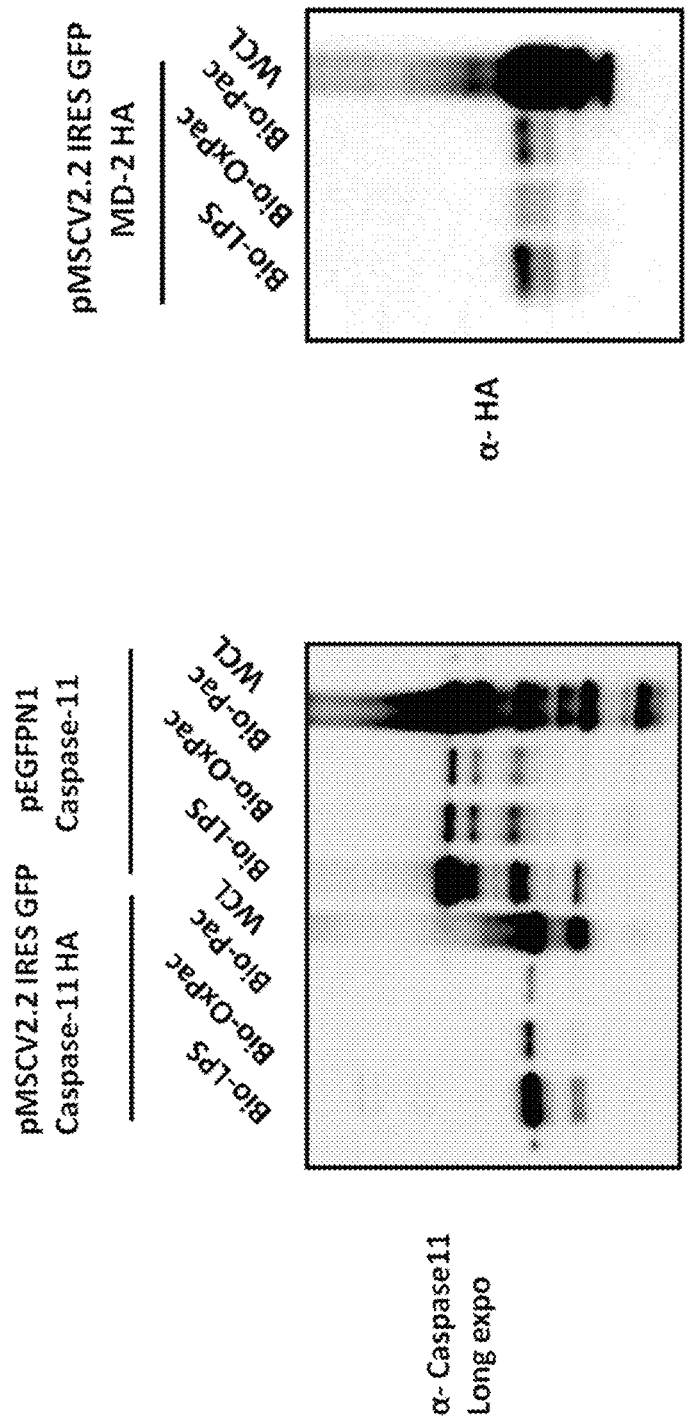
FIG. 24 shows in vitro binding assays for biotinylated LPS, OxPac and Pac to Caspase 11 and MD-2, which appeared to identify complex formation in a caspase 11-dependent manner.
Figure 25:
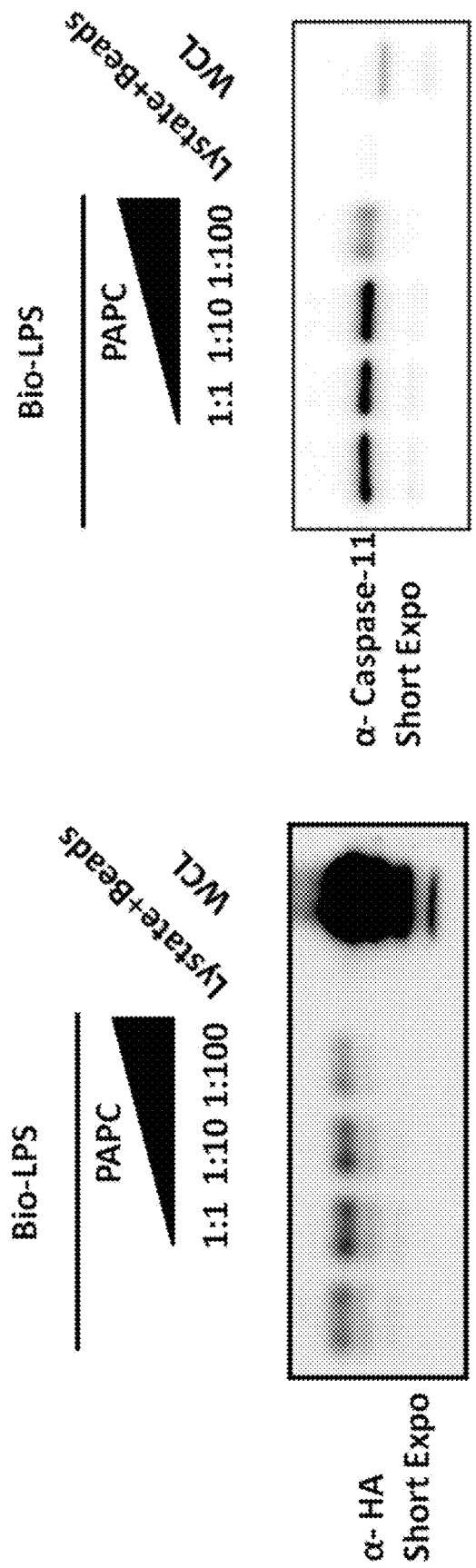
FIG. 25 shows that in a Bio-LPS pull-down, PAPC acted as a dose-dependent competitor. Biotin-LPS was used at 5 μg per pull-down assay. PAPC was used at 5, 50 and 500 μg to compete with LPS binding to MD-2 and Caspase-11, respectively. The competition started to be effective at the ratio of 1:100 (LPS:PAPC).
Figure 26:
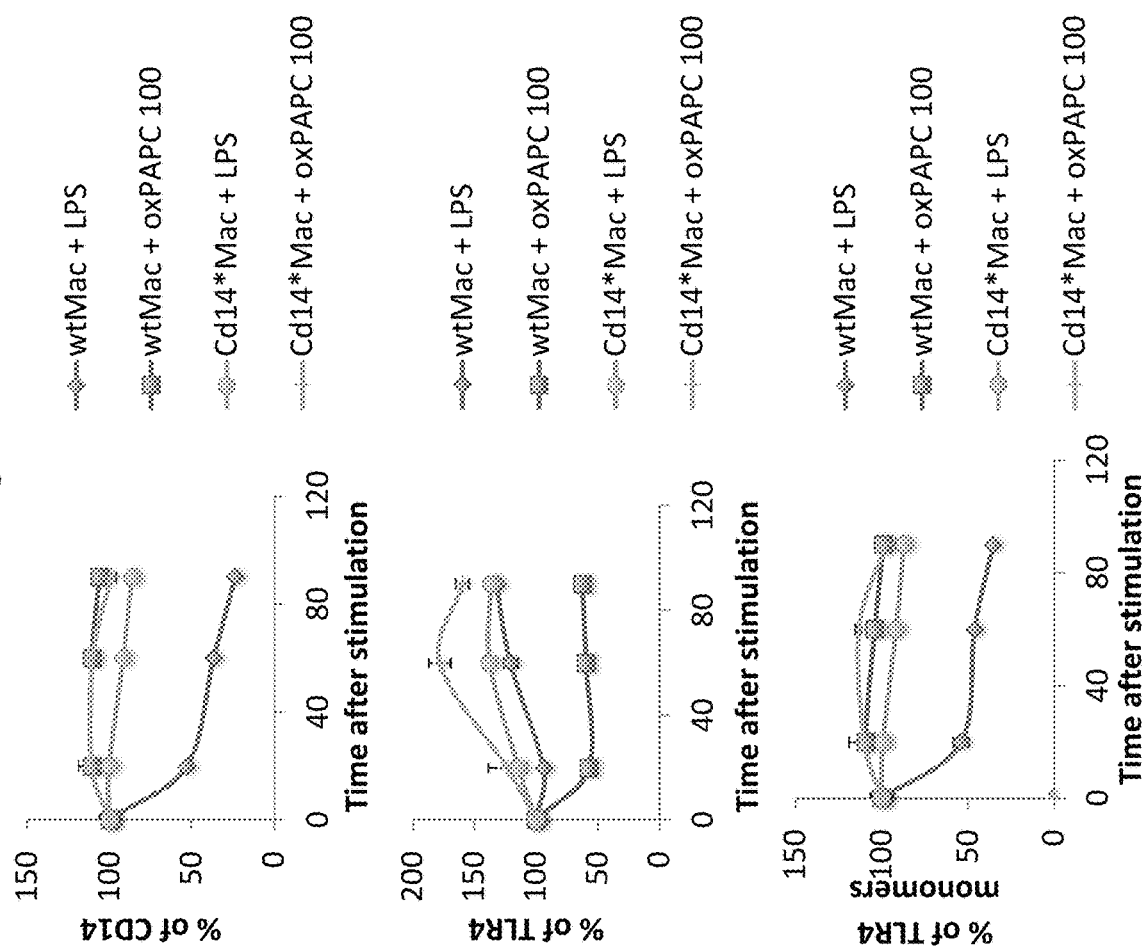
FIG. 26 shows that oxPAPC and LPS likely bound the same domain of CD14.
Figure 27:
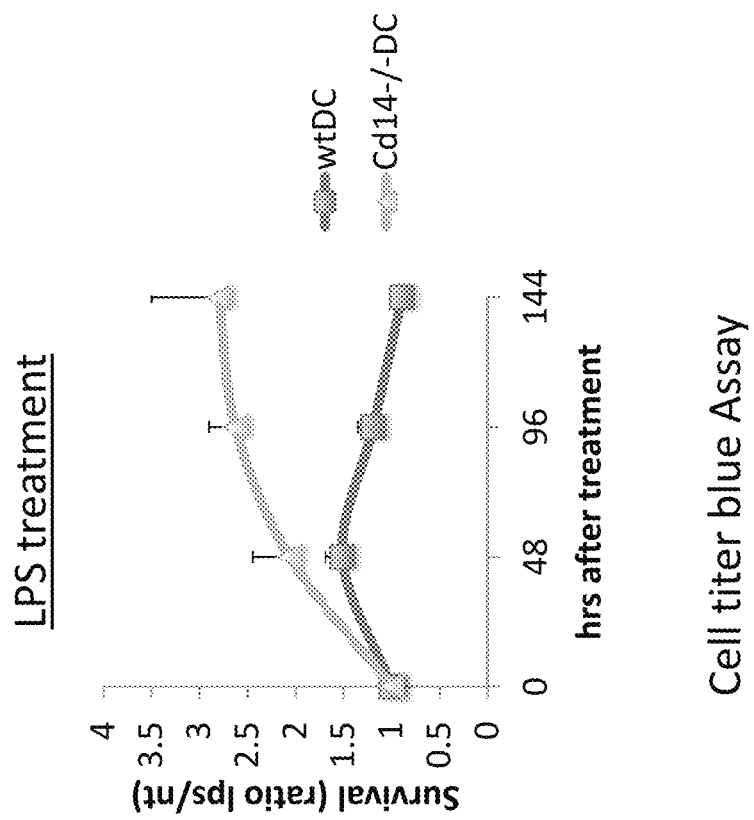
FIG. 27 shows that LPS treatment affected DC survival.
Figure 28:
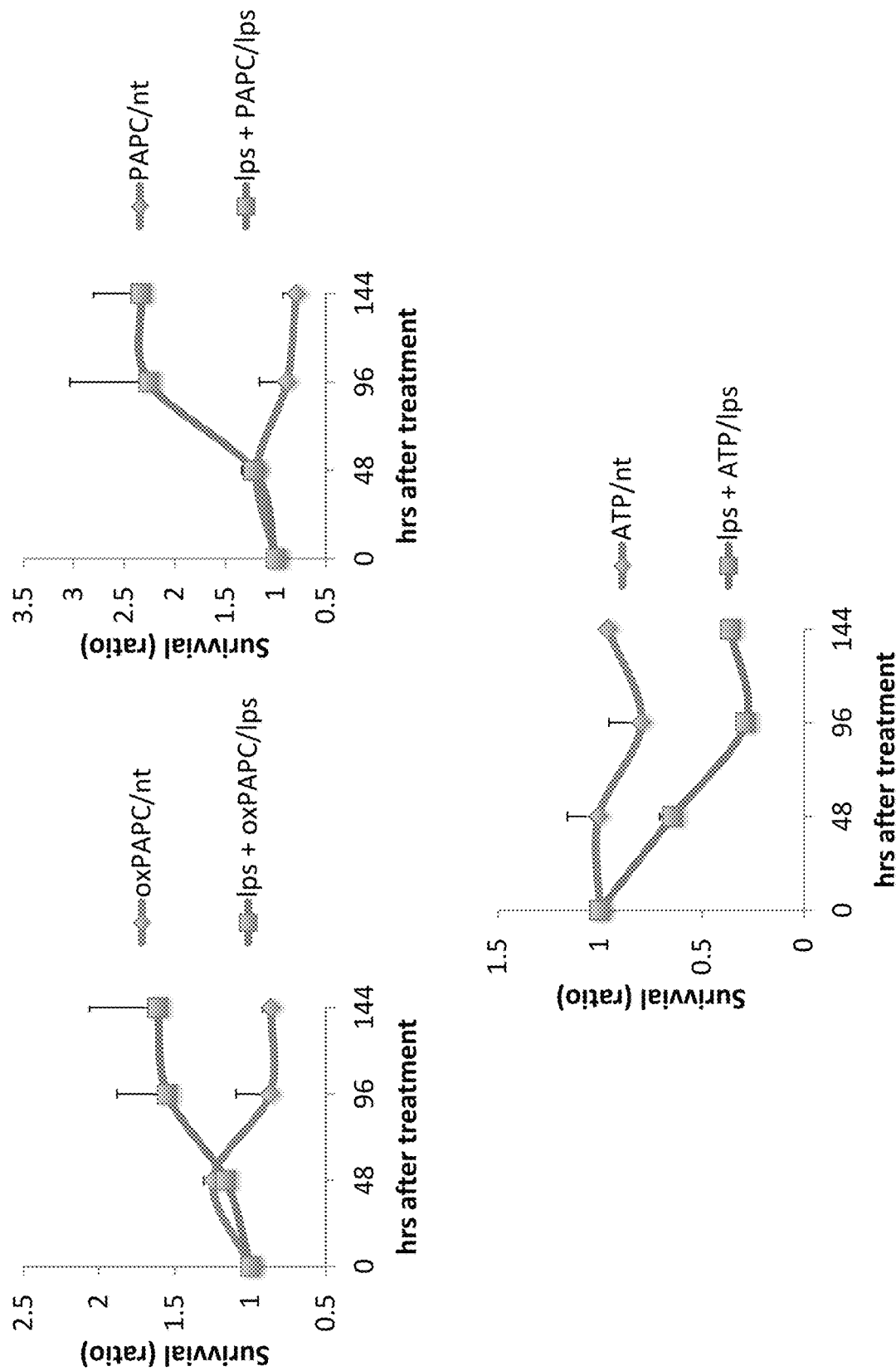
FIG. 28 shows that PAPCs treatment of primed DCs favored DC survival.
Figure 29:
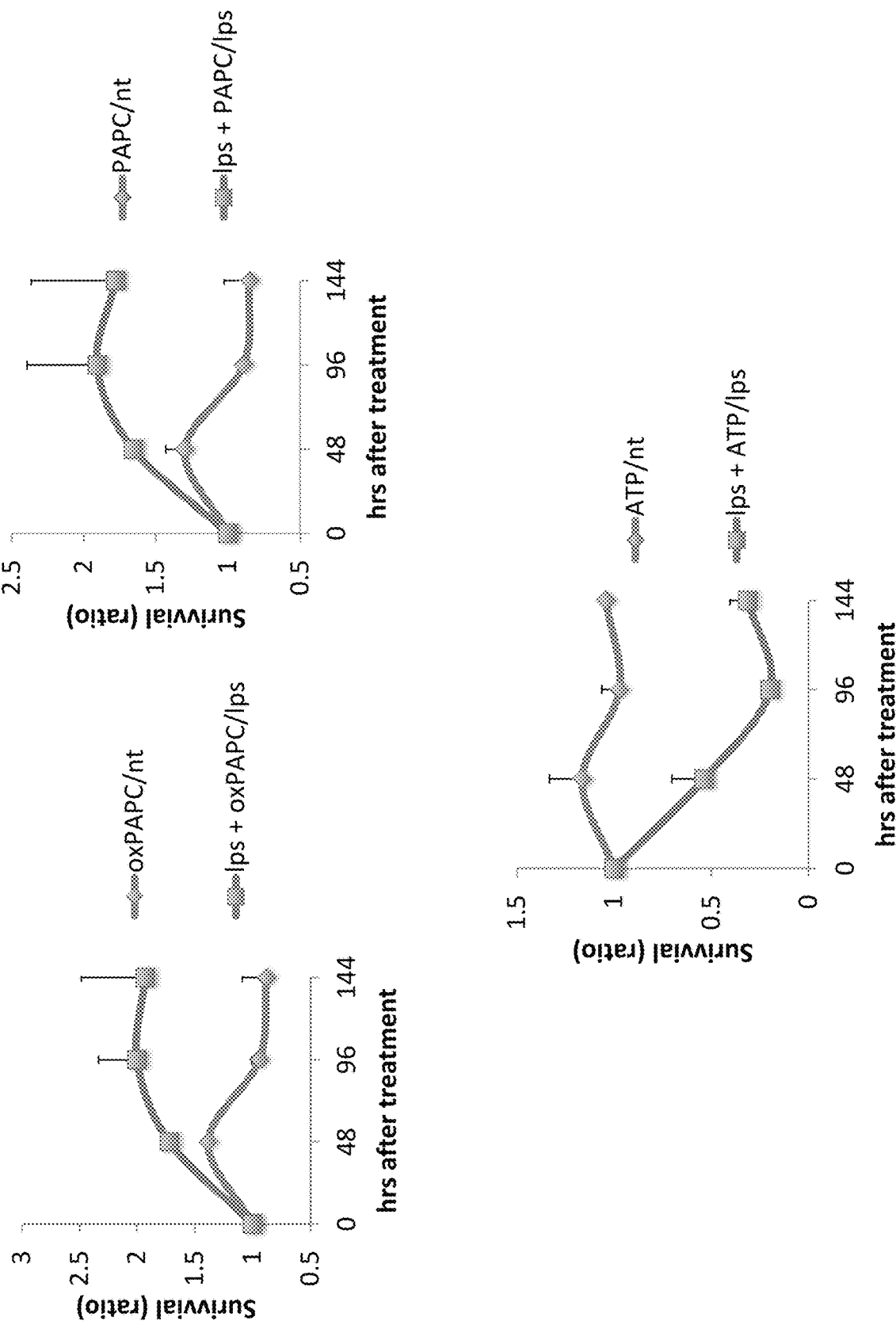
FIG. 29 shows that the observed PAPCs-dependent pro-survival effect was not CD14-dependent.

Biotinylated PAPCs were identified to potently induce CD14 internalization (FIG. 21), yet did not induce TLR4 internalization (FIG. 22) nor IL-1β secretion (FIG. 23). In vitro binding assays for biotinylated LPS, OxPac and Pac to Caspase 11 and MD-2 appeared to identify complex formation in a caspase 11-dependent manner (FIG. 24). Indeed, in a Bio-LPS pull-down assay, PAPC acted as a dose-dependent competitor (FIG. 25). In such assays, Biotin-LPS was used at 5 µg per pull-down assay, while PAPC was used at 5, 50 and 500 µg to compete with LPS binding to MD-2 and Caspase-11, respectively. The competition was effective at the ratio of 1:100 (LPS:PAPC).

oxPAPC and LPS likely bound the same domain of CD14 (FIG. 26). However, while LPS treatment affected DC survival (FIG. 27), PAPCs treatment of primed DCs favored DC survival (FIG. 28). This pro-survival effect of PAPCs was not CD14-dependent (FIG. 29). Inflammasome activation was typically associated with the release of IL-1β and the subsequent death of the activated cell. The absence of oxPAPC killing of BMDCs was a positive result further favoring use of oxPAPC as an adjuvant.

Figure 30:
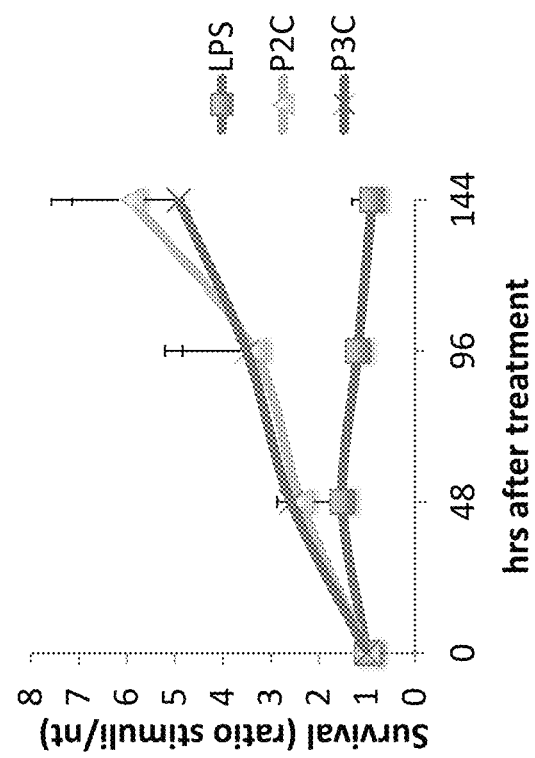
FIG. 30 shows that P2C and P3C alone supported DC survival.
Figure 31:
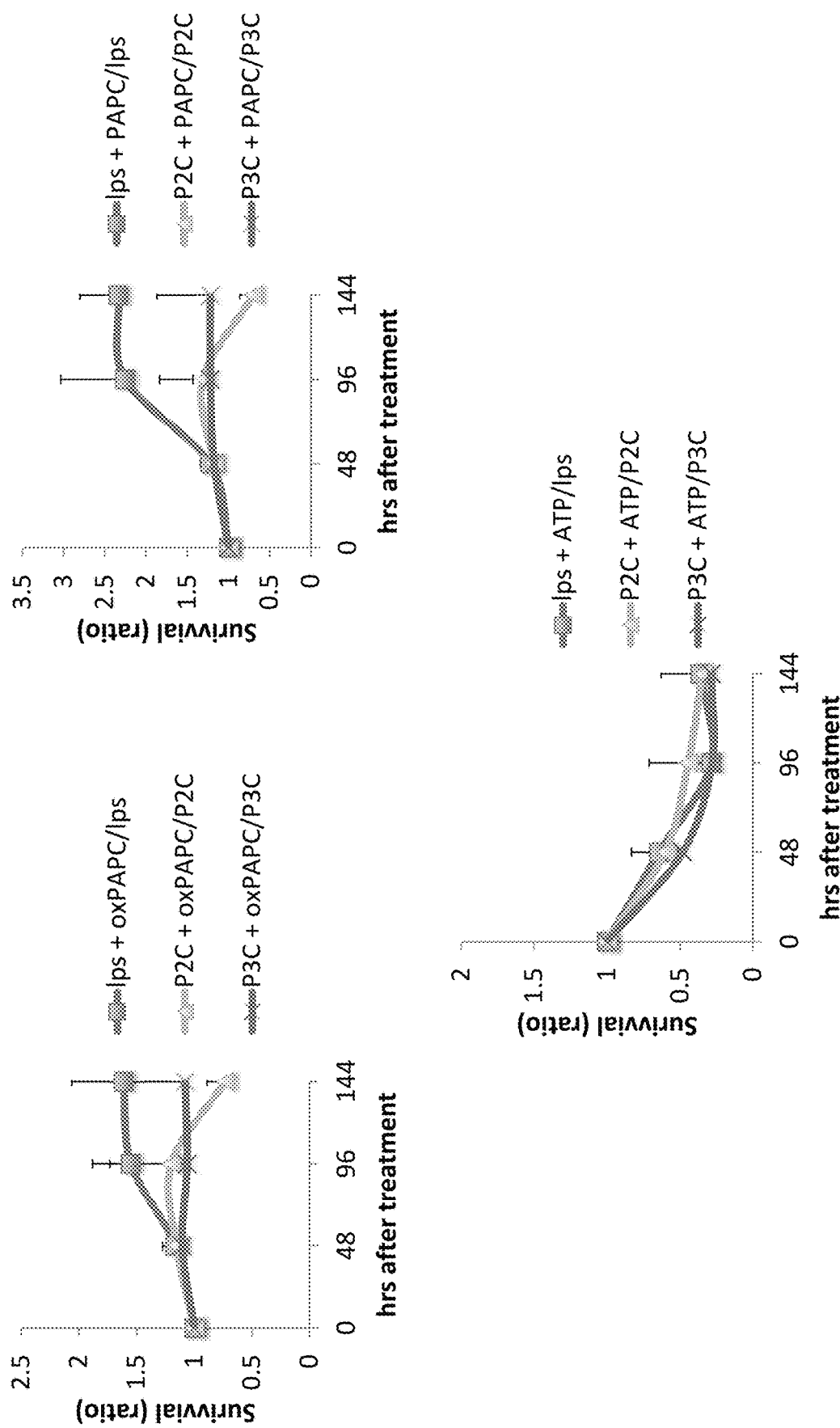
FIG. 31 shows that P2C and P3C primed DC did not increase their survival in response to PAPCs treatment.

As shown in FIG. 30, P2C and P3C alone supported DC survival. P2C and P3C primed DC did not increase their survival in response to PAPCs treatment (FIG. 31).

Figure 32:
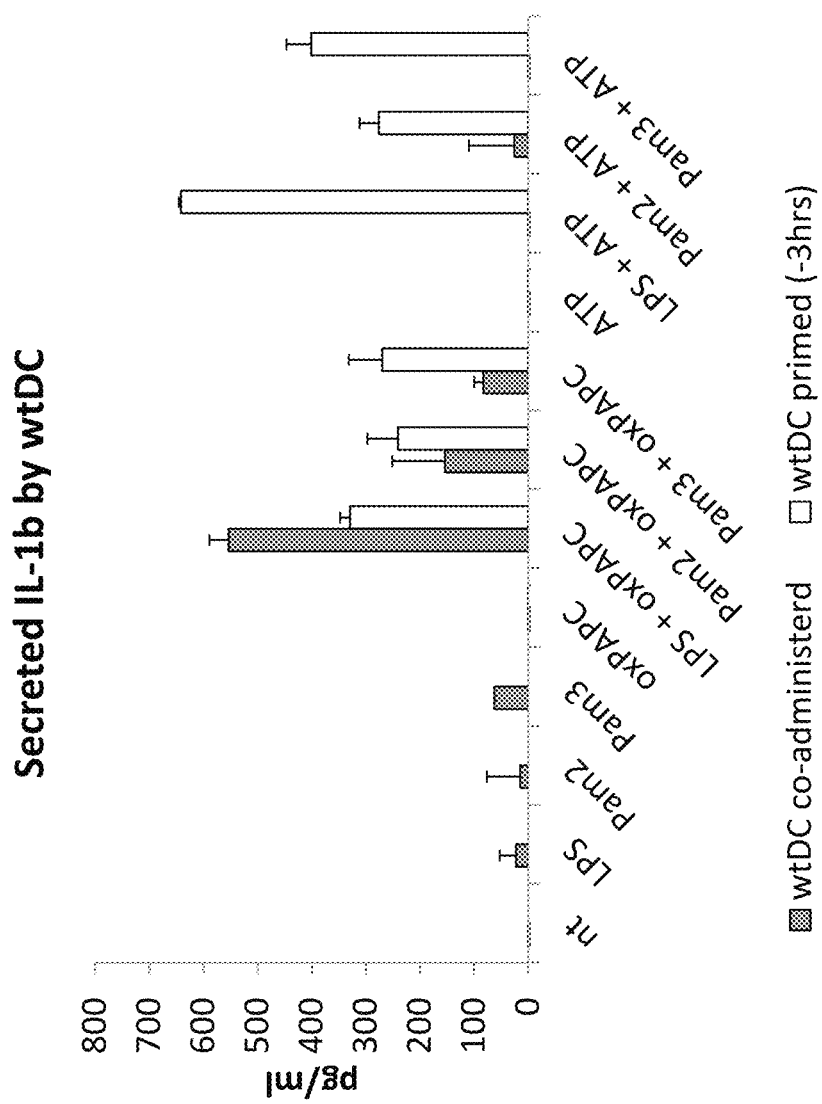
FIG. 32 shows that the inflammasome was efficiently activated by co-administration of priming stimuli and PAPCs but not ATP.
Figure 33:
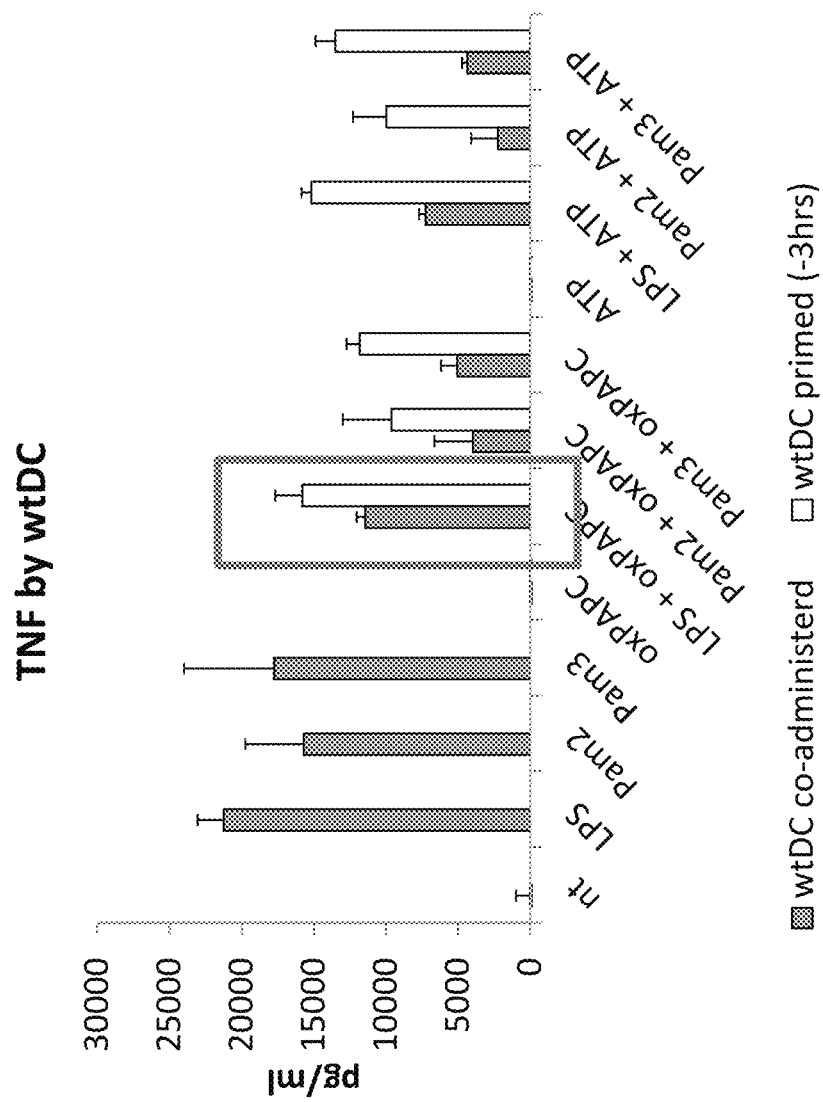
FIG. 33 shows that co-administration of priming stimuli and PAPCs did not alter NF-κB activation in wtDC.

Inflammasome was efficiently activated by co-administration of priming stimuli and PAPCs but not ATP (FIG. 32). Co-administration of priming stimuli and PAPCs did not alter NF-κB activation in wild-type DCs (FIG. 33).

Figure 34:
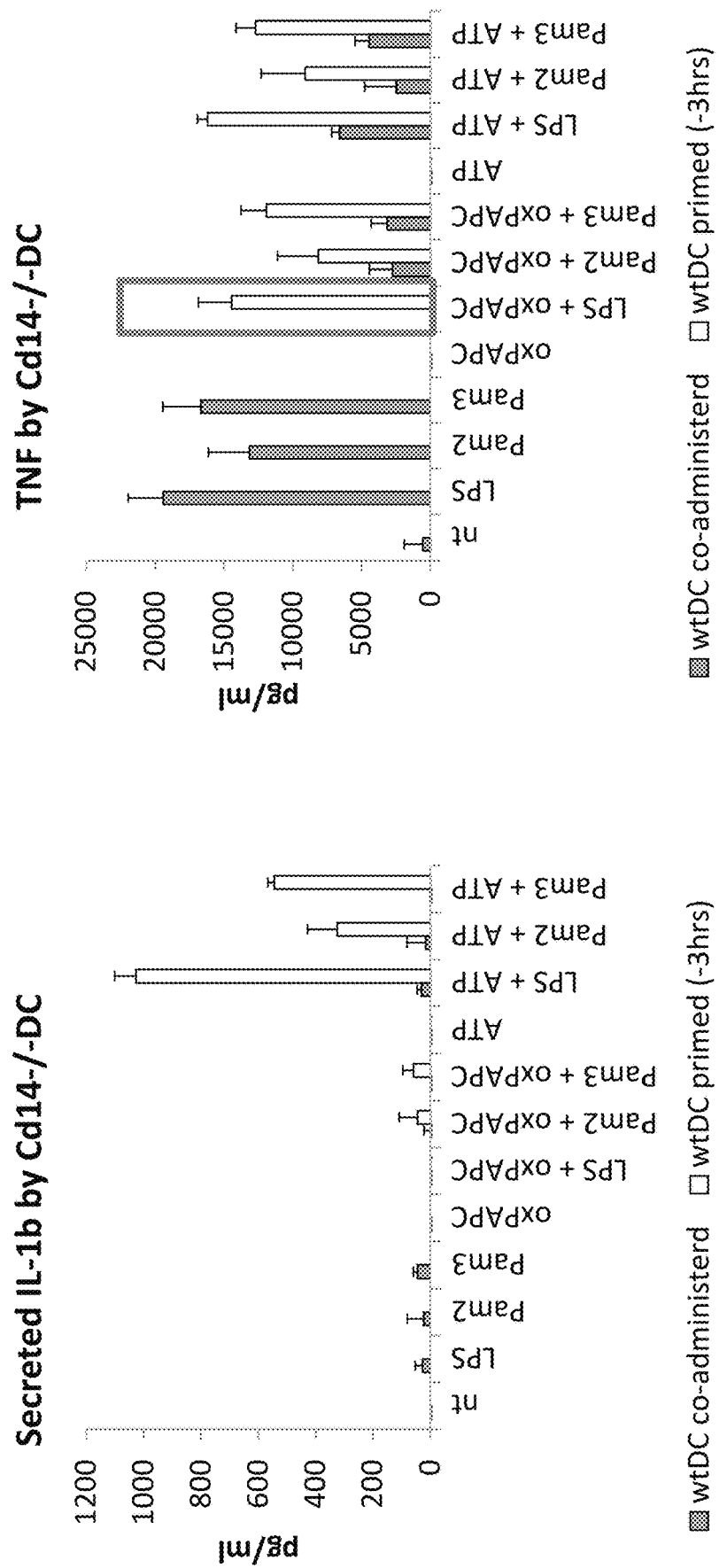
FIG. 34 shows that oxPAPC acted as an antagonist of TLR4 signaling in the absence of CD14.

In the absence of CD14, oxPAPC acted as an antagonist of TLR4 signaling (FIG. 34).

In view of the observed CD14-dependence of the oxPAPC effect, it was possible that CD14 acted as a chaperone to clear ("clean") PAPCs from the extracellular space.

Figure 35:
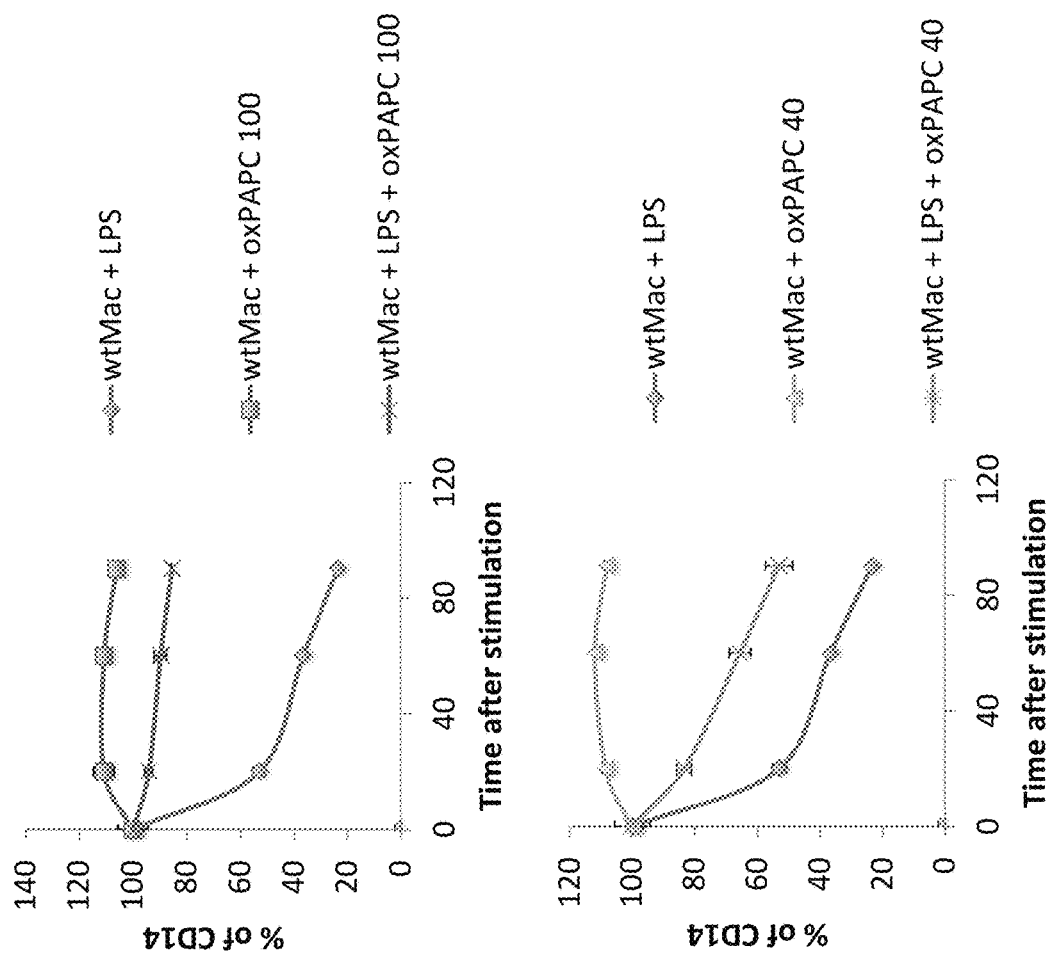
FIG. 35 shows that co-administration of LPS and oxPAPC affected TLR4 internalization.
Figure 36:
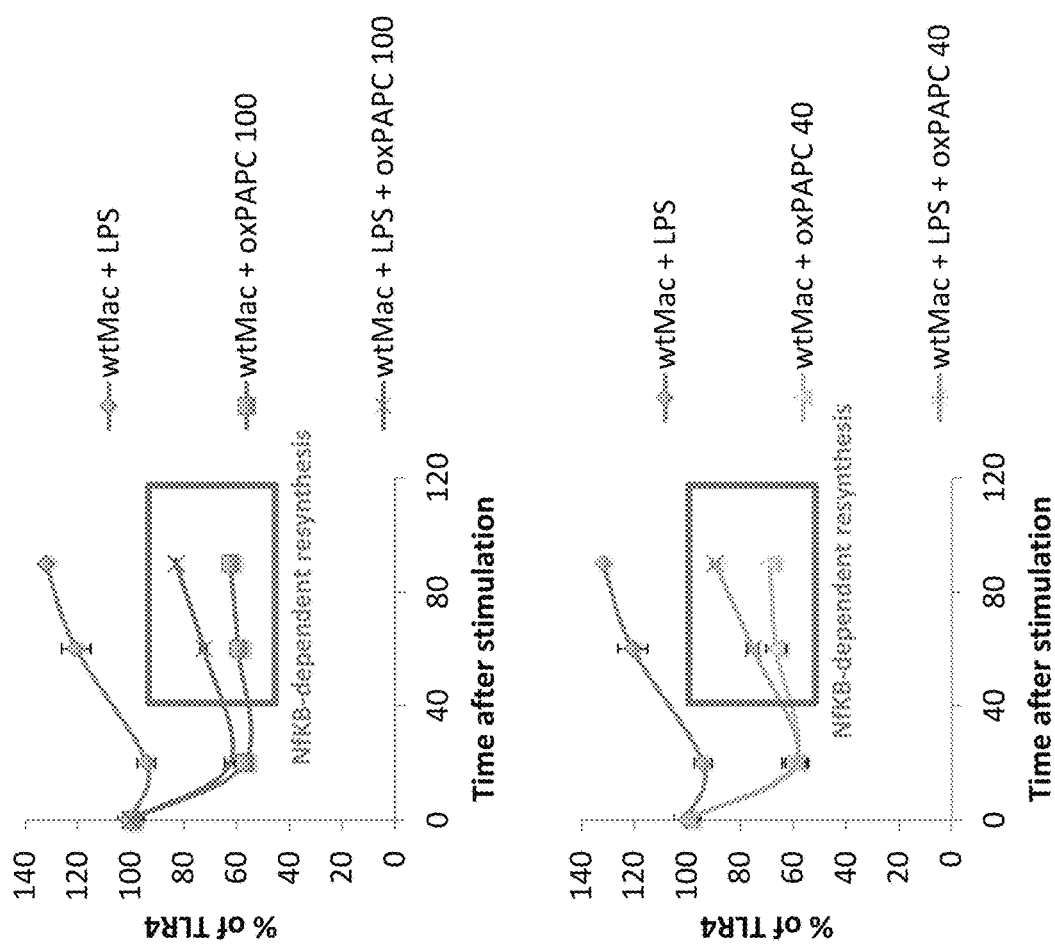
FIG. 36 shows that co-administration of LPS and oxPAPC affected CD14 internalization.
Figure 37:
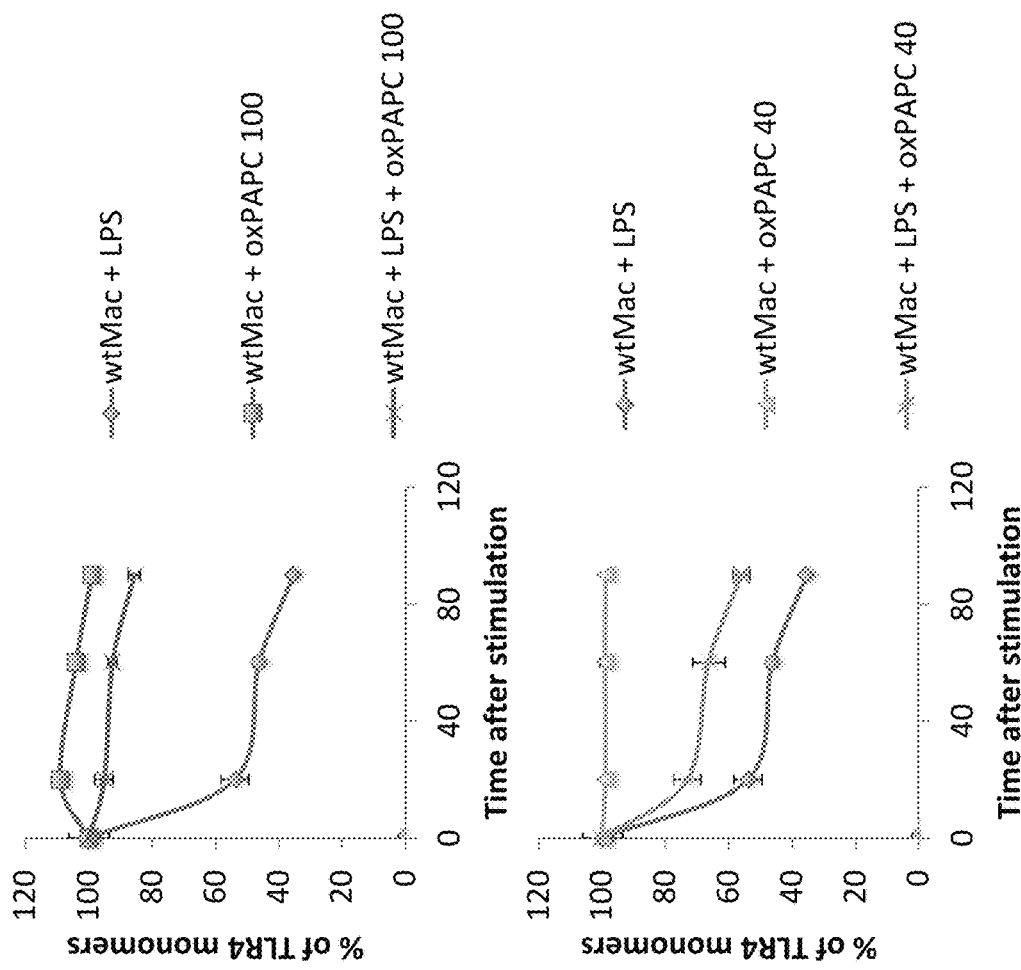
FIG. 37 shows that co-administration of LPS and oxPAPC partially affected TLR4 dimerization.

Co-administration of LPS and oxPAPC affected TLR4 internalization (FIG. 35), CD14 internalization (FIG. 36) and partially affected TLR4 dimerization (FIG. 37).

To summarize certain of the above results:
(1) Specific modified PCs (PAPCs but not DMPC) induced inflammasome activation; (2) PAPCs-dependent but not ATP-dependent inflammasome activation was cell type specific (DCs but not Macs);
(3) Inflammasome activation via PAPCs but not ATP required CD14;
(4) Inflammasome activation via PAPCs but not ATP required Caspase-11;
(5) ATP but not PAPCs induced pyroptosis in DCs;
(6) PAPCs favored DC survival in a CD14-independent way; and
(7) PAPCs, but not ATP, were identified to induce inflammasome activation when co-administered with the priming stimuli.

Thus, PAPCs were identified as a potent, natural adjuvant that could increase adaptive immune responses.

Figure 38:
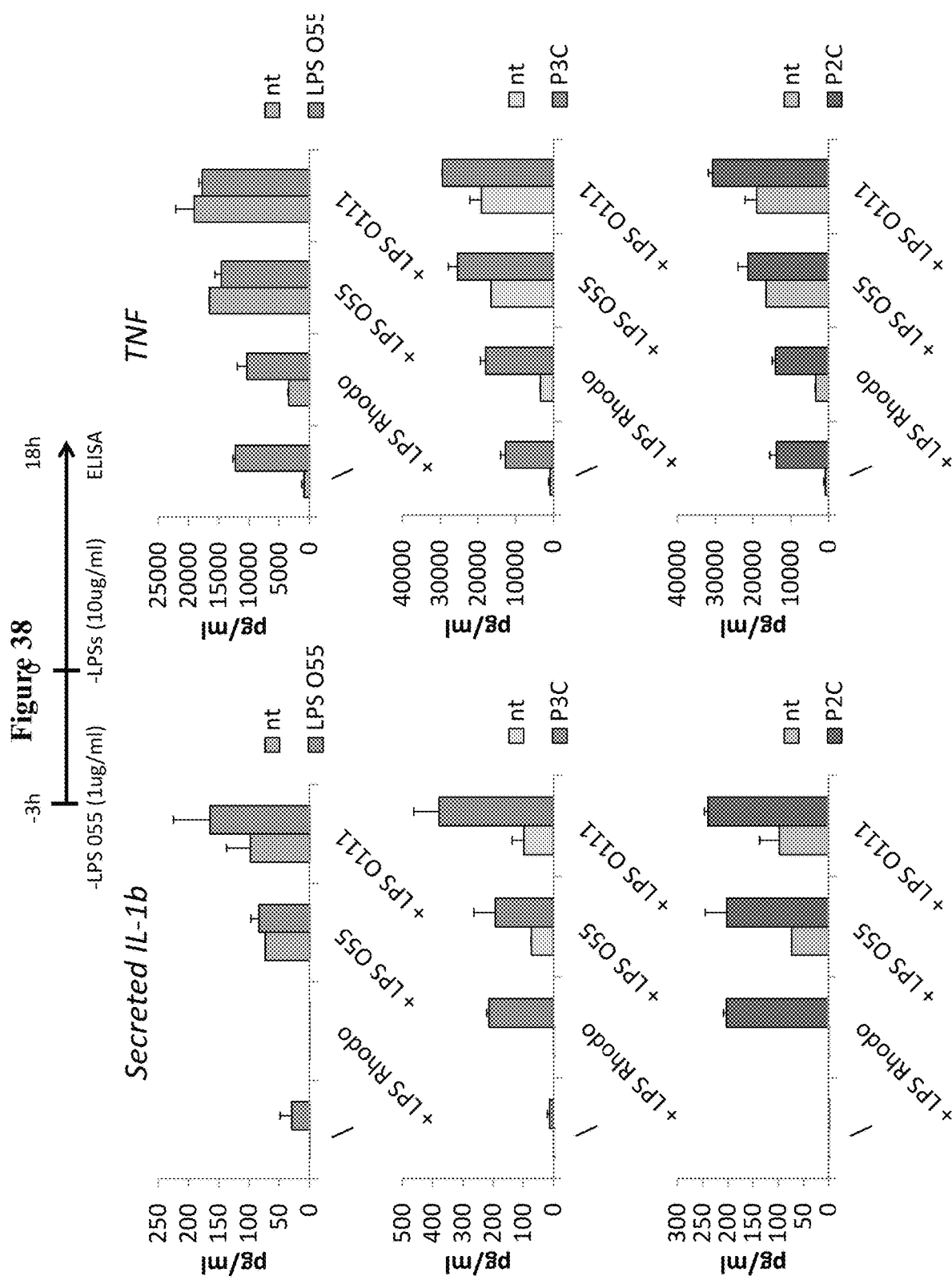
FIG. 38 shows that Rhodo LPS was a potent inducer of inflammasome activation.
Figure 39:
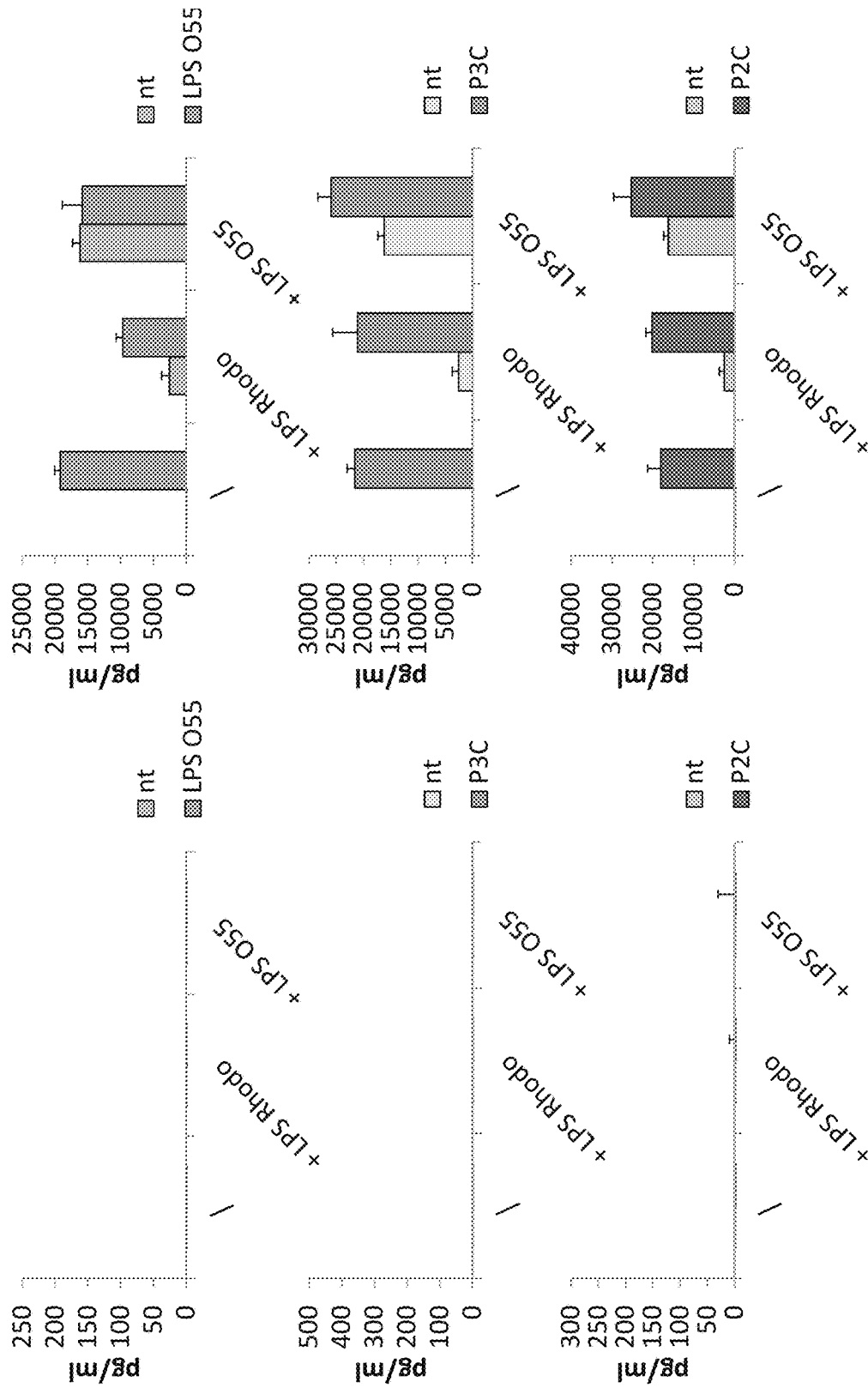
FIG. 39 shows that LPS-induced inflammasome activation was Nlrp3-dependent.
Figure 40:
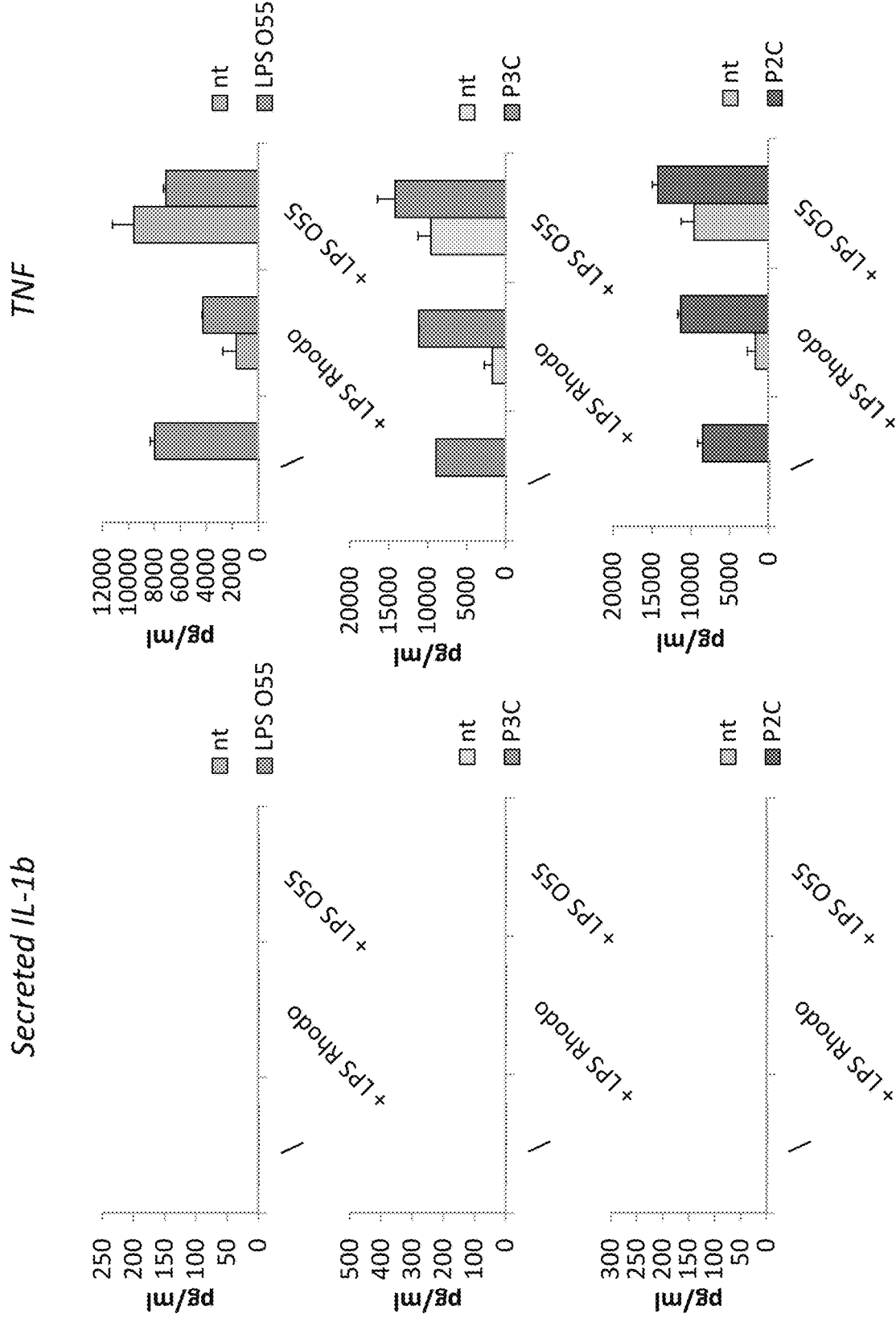
FIG. 40 shows that LPS-induced inflammasome activation was Asc-dependent.
Figure 41:
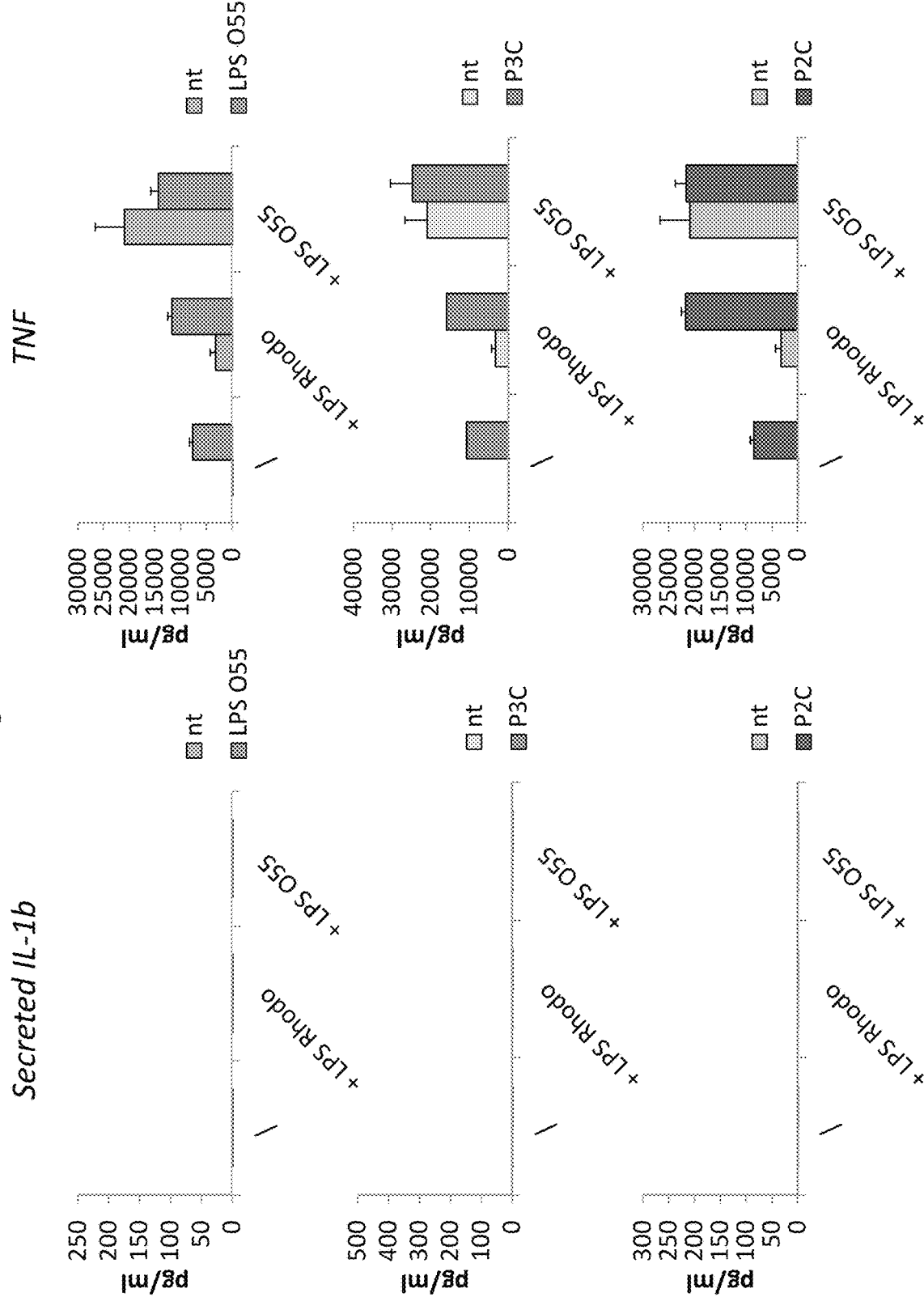
FIG. 41 shows that LPS-induced inflammasome activation was Casp1/11-dependent.
Figure 42:
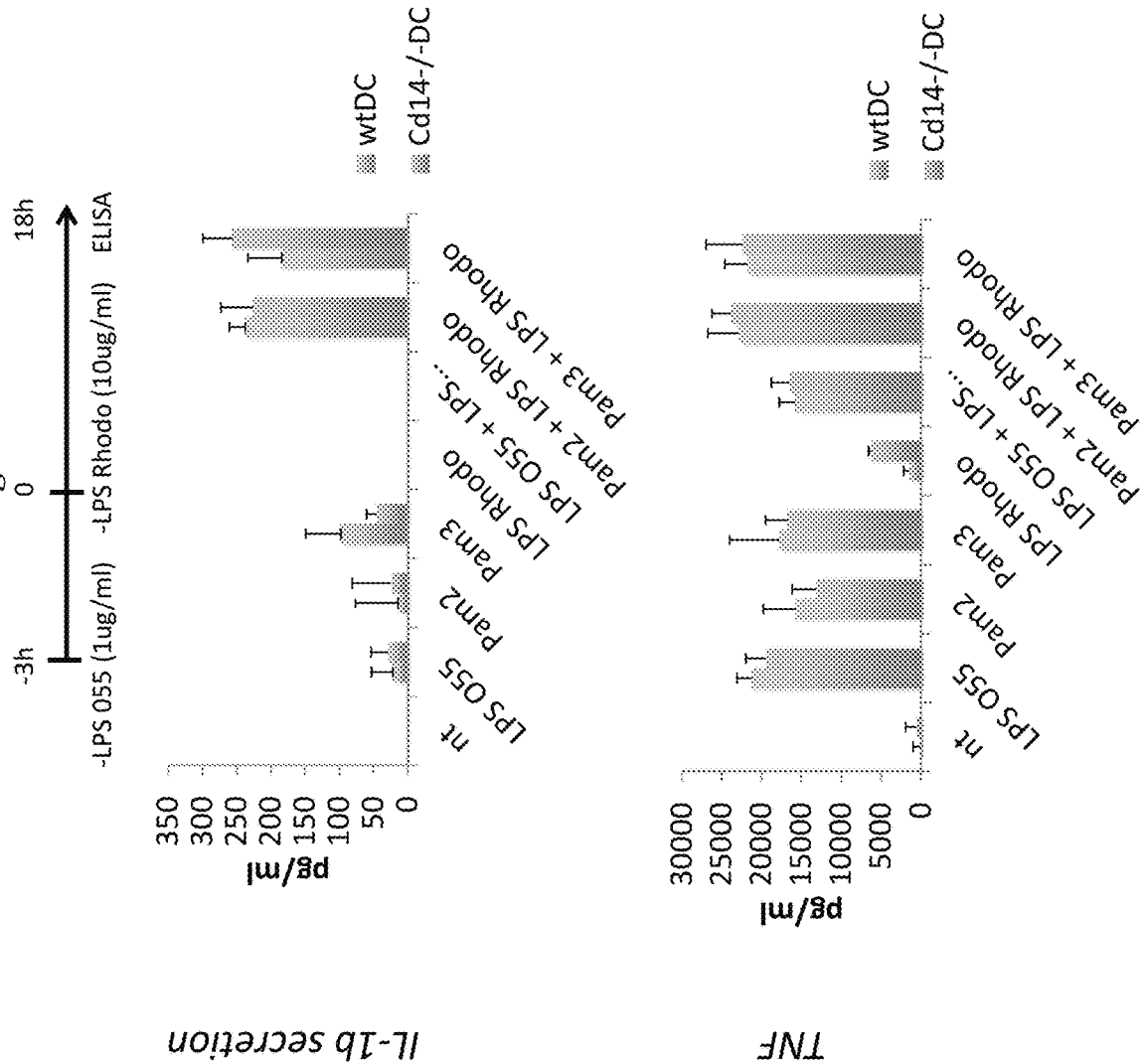
FIG. 42 shows that Rhodo LPS-induced inflammasome activation was CD14-independent.

LPS and Rhodo LPS were also assessed for inflammasome activation. As shown in FIG. 38, Rhodo LPS was a potent inducer of inflammasome activation. LPS-induced inflammasome activation was Nlrp3-dependent (FIG. 39), Asc-dependent (FIG. 40), and Casp1/11-dependent (FIG. 41). Meanwhile, Rhodo LPS-induced inflammasome activation was CD14-independent (FIG. 42). Thus, Rhodo LPS was also identified as a non-canonical inflammasome-activating lipid, though the effect appeared to be independent from CD14 (thereby distinguishing the apparent mechanism for Rhodo LPS from that seen for oxPAPCs).

Example 4: oxPAPC Did not Promote IL-1β Release from Macrophages

All well-defined inflammasome activators tested promoted IL-1β release from MΦs. To examine whether oxPAPC possessed this ability, experiments similar to those described above were performed upon primary bone marrow-derived MΦs. Interestingly, oxPAPC was unable to elicit IL-1β release under any condition examined in MΦs (FIG. 45E), whereas ATP promoted the efficient release of IL-1β from these cells in a dose-dependent manner (FIG. 51A). These data identified oxPAPC as a cell type-specific activator of inflammasome activities.

To better understand how DCs uniquely respond to oxPAPC, the response to the priming stage of inflammasome activation was evaluated. When examined side-by-side, DCs produced more TNFα than MΦs produced in response to LPS (FIG. 51D). These results indicated that DCs were better "primed" than MΦs. However, IFNγ-treated MΦs were primed as well as DCs, yet they still did not release IL-1β in response to oxPAPC (FIG. 51G). The differential responsiveness of DCs and MΦs to oxPAPC was likely manifested after the priming step had occurred, at the stage of inflammasome activation.

It was contemplated that a unique factor in DCs might exist that transports oxPAPC to the cytosol, where oxPAPC then activates inflammasome-mediated IL-1β release. This possibility was examined by transfecting oxPAPC into the M<cytosol directly. While this method promoted IL-1β release from DCs that were primed with the TLR2 ligand Pam3CSK, primed MΦs were still unable to induce such a response (FIG. 45F). LPS transfection in the cytoplasm was used as a positive control (FIG. 45F) (Hagar, J. A. et al., (2013) Science 341, 12501253; Kayagaki, N. et al. (2013) Science 341, 1246-1249). These findings indicated that some factor(s) does exist in the cytosol of MΦs (or DCs) that allows oxPAPC to activate the latter.

To understand inflammasome activities present in MΦs and DCs more generally, another inflammasome activator, ATP, which promoted IL-1β release from both types of cells (FIG. 51A) was examined. Interestingly, DCs and MΦs died in response to LPS+ATP treatments with similar kinetics, but while these cells released very different amounts of IL-1β (FIG. 45G) and expressed very different levels of ASC (FIGS. 51H-51I), none of the other components of the canonical and non-canonical inflammasome (FIG. 51I) were released or expressed. In MΦs, there was a perfect correlation between the extent of cell death and the extent of IL-1β release, an observation consistent with dying cells releasing this cytokine (FIG. 45G). In contrast, maximal amounts of IL-1β were released from DCs when minimal death was observed, an observation that was consistent with living cells releasing this cytokine (FIG. 45G). Collectively, these data highlighted fundamental differences in the activities of inflammasomes in MΦs and DCs, and indicated that oxPAPC was an activator of inflammasomes, specifically in the DCs.

Example 5: oxPAPC Promoted IL-1β Release Via Non-Canonical Inflammasome, Independent of TLR4

Caspase-11 is a known protease that binds to cytosolic LPS and promotes the assembly of non-canonical inflammasomes and the release of IL-1β (Hagar, J. A. et al., (2013) Science 341, 12501253; Kayagaki, N. et al. (2013) Science 341, 1246-1249; Shi, J. et al., (2014a) Nature 514,187-192). Since oxPAPC can mimic LPS and activate CD14 endocytosis, oxPAPC was also evaluated for its ability to activate caspase-11 dependent responses. Remarkably, oxPAPC-mediated IL-1β release was largely abolished in caspase-11 KO DCs (FIG. 46A). As expected, ATP-mediated IL-1β release remained intact in caspase-11 KO cells (FIG. 46A). In all cases, TNFα secretion was not affected (FIG. 46B). This distinction between oxPAPC and ATP, in terms of caspase-11 dependent IL-1β release, eliminated the possibility that the activities of oxPAPC were mediated by the indirect release of ATP from cells.

To complement these functional analyses, microscopic examination of individual DCs revealed that both oxPAPC and ATP induced the formation of ASC and caspase-1-containing "specks" in LPS-pretreated DCs (FIG. 46C). Of note, these experiments were performed using doses of ATP (1 mM) and oxPAPC (120 μM) that induced the release of similar levels of IL-1β (FIG. 51C). Although the kinetics of speck formation in response to oxPAPC was delayed compared to ATP, specks were formed in a similar amount of cells (FIGS. 52A-52B)). These structures were only formed under conditions where IL-1β was released, and were recognized as individual inflammasomes (Stutz, A. et al., (2013) Methods in molecular biology 1040,91-101). Interestingly, caspase-11 was required for the formation of ASC/caspase-1 containing specks in response to oxPAPC, but not ATP (FIGS. 46C and 52B). Without wishing to be bound by theory, Caspase-11 was likely required for oxPAPC-induced IL-1β release because this protein was required for non-inflammasome assembly.

Consistent with the idea that oxPAPC did not require TLR4 to exert its functions, the ability of oxPAPC to activate IL-1β release was not dependent upon TLR4 signaling. Indeed, cells primed with the TLR2 ligand, Pam3CSK, or the TLR9 ligand, CpG, elicited similar responses as those primed with LPS (FIGS. 52C-52D). As was observed for LPS-primed cells, IL-1β release from Pam3CSK-primed DCs required NLRP3, ASC and caspase-11 (FIG. 52C). ATP-mediated IL-1β release after Pam3CSK priming remained intact in caspase-11 KO cells, but not caspase-1/-11 dKO cells (FIG. 52C). All genotypes of DCs permitted comparable levels of TNFα secretion (FIG. 52C). To further dissociate any possible activity of oxPAPC on TLR4, C3H/HeJ DCs (which were naturally unresponsive to LPS due to a mutation in TLR4 TIR domain) (Poltorak, A. et al. (1998) Science 282, 2085-2088) were primed with Pam3CSK, and IL-1β secretion was measured in response to oxPAPC. The absence of a functional TLR4 did not alter the capacity of oxPAPC to induce IL-1β release (FIG. 52E). These data further confirmed that there was no requirement for oxPAPC to signal through TLR4, and that oxPAPC activated DCs upon contact with TLR ligands that were indicative of either bacterial or viral infection. Caspase-11 could therefore be classified as a receptor that controls immune responses to multiple types of pathogens, not just to gram-negative bacteria.

To further examine this possibility in an infectious setting, wild type (WT) or caspase-11 KO mice were infected with herpes simplex virus type 1 (HSV-1). HSV-1 was considered to be a good pathogen to examine, because HSV-1 infections activate NLPR3 inflammasomes in ocular models of infection (Gimenez, F. et al., (2015). Journal of leukocyte biology 2015 Oct. 29. pii: jlb.3HI0715-321R), but this virus does not encode LPS. Whether caspase-11 was involved in HSV-1 infection was previously unknown.

It was identified that caspase-11 KO mice were more susceptible to HSV-1 than WT mice on day 2 after ocular infections. Indeed, an increased abundance of infectious virus was detected in eye swabs from caspase-11, as compared to WT mice, at this time point (FIG. 52F). This difference in viral replication on day 2 was consistent with prior work demonstrating that NLRP3 KO mice yielded higher viral titers at this time point (Gimenez, F. et al., (2015). Journal of leukocyte biology 2015 Oct. 29. pii: jb.3HI0715-321R). Subsequent time points resulted in the clearance of virus from the eye of all mice examined, presumably because of the natural transition of the virus to the nervous system. These findings indicated that caspase-11 contributed to the protection of mice from a non-bacterial pathogen. Without wishing to be bound by theory, the simplest model to explain these findings was that oxPAPC production at the site of infection (the eye) contributed to caspase-11 activation and subsequent restriction of viral replication. Development of reagents that specifically ablate oxPAPC activities in vivo were contemplated as necessary for direct testing of this model.

Example 6: Caspase-11 was Identified as a Receptor for oxPAPC oxPAPC has been shown to have the ability to activate caspase-11-dependent responses, which indicates an interaction between these molecules. As previously described (Shi, J., et al., (2014b) Nature), endogenous caspase-11 can be isolated from cell lysates through interactions with biotinylated-LPS (FIG. 46D). Interestingly, biotin-oxPAPC also formed a complex with endogenous caspase-11 (FIG. 46D). In contrast, neither lipid captured endogenous caspase-3 (FIG. 46D). To determine whether oxPAPC bound directly to caspase-11, in vitro protein-lipid interaction studies were performed. As shown in FIG. 46E, oxPAPC displayed a dose-dependent resonance signal with immobilized catalytically inactive caspase-11(C254A) on surface plasmon resonance (SPR). In contrast, DMPC, which did not promote IL-1β release from DCs (FIG. 46E), did not bind detectably to caspase-11, and oxPAPC displayed no binding to IgG on the SPR (FIG. 46E). The dissociation constants (Kd) between caspase-11 and oxPAPC were calculated at $1.3 \times 10^{-6}$ M. These SPR data indicated that caspase-11 formed a complex with a self-encoded lipid (oxPAPC), in addition to LPS, and promoted IL-1β release in response to both.

Example 7: LPS and oxPAPC Interacted with Caspase-11 Via Distinct Domains and Induced Different Modes of Activation Because the same residues within CD14 were required to bind LPS and oxPAPC, whether the LPS-binding CARD was required for interactions with oxPAPC was examined. As expected (Shi et al., 2014b), mutation of specific lysine residues within the caspase-11 CARD prevented interactions with LPS, as assessed by the ability of biotin-LPS to capture caspase-11 proteins that were produced in 293T cells (FIG. 52G). Interestingly, these lysine residues did not prevent interactions with biotin-oxPAPC (FIG. 52G). Moreover, a mutant caspase-11 that lacked its entire CARD, and only contained its C-terminal catalytic domain, retained the ability to form a complex with biotin-oxPAPC (FIG. 52G). SPR analysis verified these results, as the Kd for interactions between oxPAPC and the catalytic domain of caspase-11 (noted as ΔN59) was nearly identical to that calculated for interactions with full length caspase-11 (FIG. 46E). LPS, as expected, had no ability to bind the catalytic domain of caspase-11. These data therefore established that unlike CD14, distinct domains within caspase-11 form contacts with LPS and oxPAPC.

In addition to forming a complex with caspase-11, oxPAPC induced the oligomerization of this protein, as indicated by gel filtration chromatography. As depicted in FIG. 46F, the elution of caspase-11 monomers occurred at 15.03 mL, whereas caspase-11 exposed to oxPAPC eluted at earlier volumes, which indicated an increase in the size of the protein complex. Dimers of caspase-11 were estimated to elute at 13.82 mL, and higher order oligomers were estimated to elute earlier. The ability of oxPAPC to induce the early elution of caspase-11 therefore indicated its ability to induce dimerization and/or oligomerization of this protein. The degree of oxPAPC-induced caspase-11 oligomerization was less than what was reported for the same activities in response to LPS (Shi, J., et al., (2014b) Nature).

LPS-induced oligomerization has previously been shown to promote the intrinsic protease activity of caspase-11 (Shi, J., et al., (2014b) Nature). Because LPS and oxPAPC oligomerize caspase-11 through interactions with different domains, caspase-11 enzymatic activity in response to each of these lipids was examined. As shown in FIG. 52H, it was identified that the low intrinsic enzymatic activity of caspase-11 monomers was increased upon exposure to LPS or oxPAPC, with LPS as a much more robust activator.

Without wishing to be bound by theory, there were two possible explanations for the minimal ability of oxPAPC to activate caspase-11 enzymatic activity. The first possibility was that because oxPAPC possessed weaker affinity for, and a weaker ability to oligomerize, caspase-11 than LPS, minimal caspase-11 activation occurred. In this regard, oxPAPC would have simply represented a weak version of LPS. However, the differential mechanisms by which oxPAPC and LPS engage caspase-11 indicated that these lipids engaged caspase-11 in fundamentally different manners, and that the interactions between oxPAPC and the catalytic domain were likely designed to obstruct (rather than activate) enzymatic activity. Intrinsic enzymatic activity of pre-existing caspase-11 oligomers was high (FIG. 52H), and this activity increased further upon exposure to LPS, but notably, this activity was diminished upon exposure to oxPAPC (FIG. 52H). Moreover, the ability of LPS to enhance the enzymatic activity of caspase-11 was blocked by oxPAPC, in a dose-dependent manner (FIG. 52I). These data supported the idea that two distinct biochemical interactions occurred between caspase-11 and inflammatory lipids. LPS induced strong oligomerization and enzymatic activity upon binding the CARD of caspase-11. In contrast, oxPAPC bound the catalytic domain of caspase-11, which promoted oligomerization, but limited enzymatic activity. Despite these two distinct modes of interaction, both LPS and oxPAPC assembled inflammasomes in DCs, and both promoted IL-1β release.

These findings raised the question of whether the catalytic activity of caspase-11 was needed for oxPAPC to induce IL-1β release. To address this question, caspase-11-deficient DCs were reconstituted with WT or catalytic mutant (C254A) caspase-11 expression vectors or empty vector (as control). Cells expressing WT caspase-11 regained the ability to release IL-1β in response to either LPS or oxPAPC, whereas cells expressing mutant caspase-11 did not release IL-1β in response to LPS (FIG. 46G). Interestingly, mutant reconstituted DCs produced as much IL-1β in response to oxPAPC as did cells expressing WT caspase-11 (FIG. 46G). TNFα release was used as a control (data not shown). These data established the differential requirement of caspase-11 activity for IL-1β release in response to LPS versus oxPAPC.

The capacity of mutant and WT caspase-11 to induce pyroptosis, another function regulated by the non-canonical inflammasomes was also assessed. The enzymatic activity of caspase-11 was necessary for transfected LPS to induce pyroptosis (FIG. 46G), which further confirmed the correct reconstitution of the cells. Surprisingly, no cell death in response to oxPAPC (FIG. 46G) was measured. These data therefore supported two modes of caspase-11 mediated IL-1β release, with the catalytic activity only being necessary for responses to LPS.

Example 8: CD14 Captured and Delivered oxPAPC to Caspase-11 and Promoted IL-1β Release The above studies indicated that oxPAPC possessed the following two activities: 1) it promoted CD14 endocytosis and 2) it promoted caspase-11 dependent non-canonical inflammasome activation. To determine the relationship between these activities, the requirement of CD14 for oxPAPC-induced IL-1β release was examined. Cells were primed with LPS for 3 hours, which was sufficient to permit the re-population of the plasma membrane with newly synthesized CD14 (Tan, Y. et al., (2015). Immunity 43, 909-922), and stimulated with either ATP or oxPAPC. Interestingly, CD14 was required for oxPAPC-induced IL-1β release, as CD14KO DCs released no IL-1β in response to LPS/oxPAPC or Pam3CSK/oxPAPC treatments (FIG. 47A). IL-18 secretion, another cytokine released via the actions of inflammasomes, followed a similar pattern (FIG. 53A). Similar results were obtained when stimulated DCs that were first isolated from the spleens of WT, CD14 or caspase-11 KO mice were examined. These cells exhibited a CD14 and caspase-11 dependent release of IL-1β in response to LPS/oxPAPC, whereas TNFα secretion and the upregulation of MHC-II and costimulatory molecules were unaffected by CD14 or caspase-11 deficiencies (FIGS. 47B and 53B). All responses of splenic DCs to LPS/ATP treatment were also unaffected by CD14 or caspase-11 deficiencies (FIG. 47B).

Without wishing to be bound by theory, two lines of evidence suggested that the requirement of CD14 for IL-1β release was not due to a defect in the priming phase (i.e. TLR signaling). First, the dose of LPS used (1 µg/ml) bypassed the requirement of CD14 for TLR4-induced cytokine expression, as assessed by analysis of IL-1β transcripts and secretion of TNFα (FIGS. 47A-47C). Second, Pam3CSK-primed DCs also required CD14 for oxPAPC-induced IL-1β release, even though Pam3CSK primes cells via TLR2 and not CD14 (FIGS. 47A and 47C).

In other experimental settings, type I IFNs promoted caspase-11 expression and/or activation (Broz, P. et al., (2012). Nature 490, 288-291; Case, C. L. et al., (2013). Proc Natl Acad Sci USA 110, 1851-1856; Rathinam, V. A. et al., (2012) Cell 150, 606-619). Since CD14 promoted IFN expression in response to LPS treatment, as observed by its requirement for viperin expression (FIG. 47C), the role of type I IFNs was examined. Pam3CSK/oxPAPC treated DCs secreted IL-1β (FIG. 47A) without inducing the expression of functional type I IFNs, as indicated by a lack of viperin expression (FIG. 47C). These data indicated that type I IFNs were not required to regulate IL-1β secretion in response to oxPAPC stimulation. In addition, the defect in IL-1β secretion in CD14 KO cells could not be rescued by exposure to recombinant IFNβ (FIG. 47D). IFN expression was therefore neither necessary nor sufficient for oxPAPC to activate caspase-11 dependent inflammasomes in DCs. Furthermore, caspase-1, caspase-11, NLRP3 and ASC were all expressed at comparable levels in stimulated and unstimulated WT and CD14 KO DCs (FIG. 53C), which suggested that CD14 was not required for the expression of inflammasome regulators. Collectively, these data indicated that the requirement of CD14 for oxPAPC mediated IL-1β release was not due to a requirement for cell priming. CD14 could therefore exert a direct role in promoting the inflammasome-mediated IL-1β release.

To determine the means by which CD14 promoted inflammasome activation, the endocytosis-promoting activities of this LPS receptor were evaluated. CD14 promoted oxPAPC endocytosis, and CD14 transported oxPAPC into the cell to promote IL-1β release. This bypassed the requirement of CD14 by delivering oxPAPC into the cell via alternative means. The transfection reagent DOTAP has previously proven to be a useful tool to deliver inflammatory stimuli directly to endosomes and the cytosol (Honda, K., et al., (2005) Nature 434,1035-1040). WT and CD14 KO DC were therefore primed with Pam3CSK and then exposed to DOTAP, in complex with either LPS or oxPAPC. Consistent with past results, LPS was unable to induce IL-1β release when administered to the extracellular media, but DOTAP-mediated delivery of LPS promoted IL-1β release from WT and CD14 KO DC (FIG. 47E). Interestingly, oxPAPC treatments yielded similar results. Whereas extracellular oxPAPC did not elicit IL-1β release from primed CD14 KO DCs, oxPAPC in complex with DOTAP elicited IL-1β release from CD14 KO cells, in a caspase-dependent manner (FIG. 47E). These data indicated that alternative delivery mechanisms could bypass the requirement of CD14 for oxPAPC-induced IL-1β release. The primary function of CD14 in inflammasome activation was likely therefore to deliver oxPAPC into the cell.

These data suggested that CD14 functioned to deliver LPS to TLR4 at the cell surface, and to deliver oxPAPC to caspase-11 in the cytosol via some endosomal intermediate. Since endolysosomes are highly degradative organelles, it was possible that the delivery of oxPAPC to endosomes would also consume this lipid, and limit its inflammatory activities. Consistent with this idea, treatment of DCs with the acidification inhibitor chloroquine, which blocks endo-lysosomal activity, promoted slightly more release of IL-1β from DCs (FIG. 53D).

Further, LPS promoted IL-1β release from naïve cells when delivered directly to the cytoplasm, whereas DOTAP only permitted oxPAPC to trigger IL-1β release from cells primed with a TLR ligand. This difference in the dependence for priming was likely due to the fact that LPS possessed the ability to prime the cells via TLR4 and activate IL-1β release via caspase-11. In contrast, oxPAPC possessed no ability to prime the cells directly, and therefore depended on a TLR stimulus. These data reinforced the idea that the principle of coincidence detection operates to govern two types of DC activation states. The first activation state was achieved when DCs encountered PAMPs, and resulted in the release of classic TLR-dependent cytokines via conventional protein secretion. The second, hyperactive, state was achieved either when DCs encountered DAMPs in the presence of PAMPs (i.e. coincidence detection), or when virulent bacteria delivered LPS to the cytosol directly (Aachoui, Y., et al. (2013a). Science 339, 975-978; Casson, C. N., et al. (2013). PLoS Pathog 9, e1003400; Hagar, J. A. et al., (2013) Science 341, 12501253).

Example 9: Unlike Other Inflammasome Activators, oxPAPC Did not Kill Cells

In addition to promoting IL-β release, inflammasome activation has been typically associated with the induction of cell death (Aachoui, Y., (2013b). Current opinion in microbiology 16, 319-326). Without wishing to be bound by theory, cell death via non-canonical inflammasomes is believed to depend upon the enzymatic activity of caspase-11, which must cleave at least two proteins, gasdermin d and pannexin-1 (Kayagaki, N. et al., (2015) Nature 526, 666-671; Shi, J. et al., (2015) Nature 526, 660-665; Yang, D. et al., (2015) Immunity 43, 923-932). Since oxPAPC did not require the catalytic activity of caspase-11 to promote IL-11 release, it was contemplated that oxPAPC would not kill cells. To assess this possibility directly, pyroptosis induction after oxPAPC administration or LPS transfection in LPS-primed DCs was measured. Pyroptosis is characterized by a rapid loss of plasma membrane integrity, which should release cytoplasmic proteins (and organelles) from the cell body. LDH release in the supernatant was used to assess membrane permeabilization of the cell population during pyroptosis. LPS/ATP-treated cells released LDH starting 4 hours after treatment (FIG. 48A); this combination was a well-defined activator of inflammasome-mediated cell death (Aachoui, Y., (2013b). Current opinion in microbiology 16, 319-326). Cells transfected with LPS, independently from LPS priming, died at later time points than cells treated with ATP (FIG. 48A). Interestingly, all conditions that activated caspase-11 (e.g. LPS transfection or oxPAPC treatment), yielded similar amounts of IL-11 in the supernatant (FIG. 48B), yet only LPS transfection caused LDH release (FIG. 48A). These data indicated that oxPAPC promoted the release of IL-11 from living cells.

To corroborate these observations, a single cell assay was developed which examined viability of cells that contained assembled inflammasomes, as revealed by the presence of ASC-containing aggregates. It was contemplated that living cells should resist staining with Zombie dye, a stain that labels the cytosol of cells whose plasma membranes have been disrupted. Cells with intact plasma membranes should also retain functional organelles. In contrast, pyroptotic cells should have lost their organelles and should stain strongly for Zombie dye. As shown in FIGS. 48C and 48D, cells treated with LPS/ATP contained ASC specks, and these cells lost mitochondria and stained positive for Zombie dye. In striking contrast, cells treated with LPS/oxPAPC contained ASC specks, but retained functional mitochondria and displayed minimal Zombie dye staining (FIGS. 48C-48D). These collective observations indicated that oxPAPC possessed no capacity to kill cells, and strongly indicated that oxPAPC induced IL-1β release from living cells. Moreover, not only did oxPAPC not induce pyroptosis, this lipid counteracted the slow acting death pathways activated by LPS in DCs (Zanoni, I. et al. (2009) Nature 460, 264-268). For this experiment, the health of individual cells within the population up to 72 hours after treatment was assessed by flow cytometry, using the viability stain 7-AAD, which detected genomic DNA within cells whose membranes had been permeabilized (Paterson, A. M. et al., (2011) J Immunol 187, 1097-1105). Using concentrations of ATP (1 mM) that induced comparable amounts of IL-1β release as those elicited by oxPAPC (FIG. 48B), LPS/ATP treatment diminished DC viability soon after treatment (FIG. 54A). Remarkably, whereas LPS treatment alone decreased cell viability at extended time points (FIGS. 48E-48F), LPS/oxPAPC treatment actually increased viability of the cell population (FIG. 48F). These data indicated that oxPAPC treatment interfered with LPS-induced DC apoptosis to promote viability.

Example 10: oxPAPC was a Potent Adjuvant Supplement that Promoted T-Cell Mediated Adaptive Immunity While caspase-11 contributed to the control of an acute viral infection (FIG. 52F), the dual abilities of oxPAPC to promote DC survival and IL-1β release suggested that oxPAPC might also promote DC-mediated adaptive immune responses. Indeed, the product of caspase-11 activation, IL-1β, has been characterized as possessing several activities that promote T-cell activation (Sims, J. E., and Smith, D. E. (2010) Nat Rev Immunol 10, 89-102), including rendering these cells resistant to regulatory T cell suppression (Schenten, D. et al. (2014). Immunity 40, 78-90). The oxPAPC/LPS mixtures were examined for their ability to display potent adjuvant activity in vivo.

To address this possibility, WT, caspase-11 and caspase-1/-11 dKO mice were injected subcutaneously with LPS, ovalbumin (OVA) and/or oxPAPC that had been emulsified in incomplete Freund's adjuvant (IFA). This exact inoculation route has been used to establish the ability of TLR ligands to promote T-cell differentiation (Pasare, C., and Medzhitov, R. (2004) Immunity 21, 733-741; Schnare, M. et al., (2001) Nat Immunol 2, 947-950). 40 days after injection, CD4+ T-cells were isolated from the draining lymph nodes and exposed ex vivo to DCs that were pulsed (or not) with OVA. T-cell activation was then assessed by measuring the abundance of IL-2, IL-17 and IFNγ by ELISA. Restimulations performed with DC alone (no OVA) did not elicit IL-2, IL-17 or IFNγ, indicating that the cytokines released during restimulations resulted from antigen specific T-cell responses (FIGS. 48G and 54B).

Interestingly, T-cells isolated from mice immunized with LPS/oxPAPC mixtures yielded substantially higher levels of IFNγ and IL-17 release than T-cells isolated from mice immunized with LPS (FIGS. 48G and 54B). The ability of oxPAPC to enhance T-cell activation was lost in caspase-11 or caspase-1/-11 dKO mice (FIGS. 48G and 54B), an observation consistent with all in vitro data presented herein. Similar results were obtained measuring T-cell activation 7 days after immunization, i.e. during the effector phase of T cell activation (FIG. 54C). Thus, oxPAPC possessed the capacity to potentiate LPS-mediated T-cell activation in a caspase-11 dependent manner.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:
1. A method for inducing or enhancing an adaptive immune response to a cancer in a mammalian subject in need thereof, the method comprising:
 subcutaneously administering a therapeutically effective amount of (i) a toll-like receptor (TLR) ligand, wherein the TLR ligand is a TLR4 ligand, a TLR2 ligand, and/or a TLR9 ligand, (ii) an oxidated 1-palmitoyl-2-arachidonyl-sn-glycero-3-phosphorylcholine (oxPAPC) species, and (iii) a cancer immunogen to the mammalian subject in need thereof.
2. The method of claim 1, wherein the TLR4 ligand is LPS or monophosphoryl lipid A (MPLA).
3. The method of claim 1, wherein the TLR2 ligand is Pam3CSK or Pam2CSK.
4. The method of claim 1, wherein the TLR9 ligand is CpG.
5. The method of claim 1, wherein the oxPAPC species is selected from 2-[[(2R)-2-[(E)-7-carboxy-5-hydroxyhept-6-enoyl]oxy3-hexadecanoyloxypropoxy]-hydroxyphosphoryl]oxyethyl-trimethylazanium (HOdiA-PC2-(trimethylazaniumyl) ethyl phosphate (KOdiA-PC2-(5-hydroxy-8-oxo-octenoyl)-sn-glycero-3-phosphorylcholine (HOOA-PC), 2-[[(2R)-2-[(E)-5,8-dioxooct-6-enoyl]oxy-3-hexadecanoyloxypropoxy]-hydroxyphosphoryl]oxyethyl-trimethylazanium (KOOA-PC2-(5,6 epoxyisoprostanoyl)-sn-glycero-3-phosphocholine) (PEIPC).
6. The method of claim 5, wherein the oxPAPC species is KOdiA-PC.
7. The method of claim 1, wherein the (i) a toll-like receptor (TLR) ligand, (ii) oxidated 1-palmitoyl-2-arachidonyl-sn-glycero-3-phosphorylcholine (oxPAPC) species, and (iii) cancer immunogen are administered in an amount effective to induce hyperactivation of the subject's dendritic cells.
8. The method of claim 1, wherein the subject is a human.
9. The method of claim 1, wherein the TLR ligand, oxPAPC species, and cancer immunogen are administered as part of a pharmaceutical composition.
10. The method of claim 1, wherein the immune response is a prophylactic immune response.
11. The method of claim 1, wherein the immune response is a therapeutic immune response.
12. The method of claim 1, wherein the adaptive immune response comprises T-cell activation.
13. The method of claim 1, wherein the cancer immunogen is a tumor antigen.
14. The method of claim 1, wherein the cancer is selected from the group consisting of sarcoma, lymphoma, leukemia, carcinoma, melanoma, and astrocytoma.
15. The method of claim 14, wherein the carcinoma is selected from carcinoma of the breast, carcinoma of the prostate, ovarian carcinoma, carcinoma of the cervix, colon carcinoma, carcinoma of the lung, and combinations thereof.

16. The method of claim 15, wherein the astrocytoma is glioblastoma.

17. A pharmaceutical composition comprising:
(i) a TLR agonist;
(ii) an oxPAPC species; and
(iii) a cancer immunogen.

* * * * *

UNITED STATES PATENT AND TRADEMARK OFFICE
CERTIFICATE OF CORRECTION

PATENT NO. : 11,351,250 B2
APPLICATION NO. : 17/018045
DATED : June 7, 2022
INVENTOR(S) : Jonathan C. Kagan Page 1 of 1

It is certified that error appears in the above-identified patent and that said Letters Patent is hereby corrected as shown below:

On the Title Page

Item [56] Line 37, delete "tire" and insert -- the --;

Item [57] Line 3, delete "arachidonyl" and insert -- arachidonoyl --.

In the Specification

Column 12, Line 31, delete "arachidonyl" and insert -- arachidonoyl --;

Column 13, Line 17, delete "arachidonyl" and insert -- arachidonoyl --;

Column 15, Line 67, delete "arachidonyl" and insert -- arachidonoyl --.

In the Claims

Column 44, Lines 21-22, Claim 1, delete "arachidonyl" and insert -- arachidonoyl --;

Column 44, Line 33, Claim 5, delete "oxy3" and insert -- oxy-3 --;

Column 44, Line 34, Claim 5, delete "PC2-" and insert -- PC), [(2R)-2-[(E)-7-carboxy-5-oxohept-6-enoyl]oxy-3-hexadecanoyloxypropyl] 2- --;

Column 44, Line 35, Claim 5, delete "PC2-" and insert -- PC), 1-palmitoyl-2- --;

Column 44, Line 39, Claim 5, delete "PC2-" and insert -- PC), and (1-palmitoyl-2- --;

Column 44, Lines 44-45, Claim 7, delete "arachidonyl" and insert -- arachidonoyl --.

Signed and Sealed this
First Day of November, 2022

Katherine Kelly Vidal
*Director of the United States Patent and Trademark Office*